United States Patent
Lefrancois et al.

(10) Patent No.: US 8,765,766 B2
(45) Date of Patent: *Jul. 1, 2014

(54) PYRIMIDINE DERIVATIVES WHICH ARE ANTAGONISTS OF THE VITRONECTIN RECEPTOR

(75) Inventors: Jean-Michel Lefrancois, Livry Gargan (FR); Bertrand Heckmann, Bures sur Yvette (FR)

(73) Assignee: Galapagos NV, Mechelen (BE)

(*) Notice: Subject to any disclaimer, the term of this patent is extended or adjusted under 35 U.S.C. 154(b) by 0 days.

This patent is subject to a terminal disclaimer.

(21) Appl. No.: 13/353,287

(22) Filed: Jan. 18, 2012

(65) Prior Publication Data

US 2012/0115883 A1 May 10, 2012

Related U.S. Application Data

(63) Continuation of application No. 12/911,691, filed on Oct. 25, 2010, now Pat. No. 8,133,896, which is a continuation of application No. 12/541,876, filed on Aug. 14, 2009, now Pat. No. 7,846,932, which is a continuation of application No. 11/596,597, filed as application No. PCT/FR2005/001209 on May 13, 2005, now Pat. No. 7,825,119.

(30) Foreign Application Priority Data

May 18, 2004 (FR) .................................. 04 05407

(51) Int. Cl.
*A61K 31/506* (2006.01)
*C07D 239/24* (2006.01)

(52) U.S. Cl.
CPC ............ *A61K 31/506* (2013.01); *C07D 239/24* (2013.01)
USPC .......................................... 514/256; 544/328

(58) Field of Classification Search
CPC .............................. A61K 31/506; C07D 239/24
USPC .......................................... 514/256; 544/328
See application file for complete search history.

(56) References Cited

U.S. PATENT DOCUMENTS

| | | | |
|---|---|---|---|
| 6,723,727 B1 | 4/2004 | Peyman et al. | |
| 6,743,800 B1 | 6/2004 | Peyman et al. | |
| 6,992,187 B2 | 1/2006 | Peyman et al. | |
| 7,582,640 B2 | 9/2009 | Ruxer et al. | |
| 7,763,621 B2 | 7/2010 | Ruxer et al. | |
| 7,825,119 B2 | 11/2010 | Lefrancois et al. | |
| 7,846,932 B2 | 12/2010 | Lefrancois et al. | |
| 8,133,896 B2 | 3/2012 | Lefrancois et al. | |
| 2003/0203896 A1 | 10/2003 | Peyman et al. | |
| 2008/0058348 A1 | 3/2008 | Lefrancois et al. | |

FOREIGN PATENT DOCUMENTS

| | | |
|---|---|---|
| CA | 2225366 | 6/1998 |
| DE | 100 42 655 | 3/2002 |
| EP | 0 528 586 | 2/1995 |
| EP | 0 528 587 | 2/1995 |
| EP | 0 820 991 | 1/1998 |
| EP | 0 933 367 | 8/1999 |
| EP | 1 065 207 | 1/2001 |
| JP | 10-182645 | 7/1998 |
| WO | WO-94/08577 | 4/1994 |
| WO | WO-94/12181 | 6/1994 |
| WO | WO-95/32710 | 12/1995 |
| WO | WO-96/00574 | 1/1996 |
| WO | WO-96/00730 | 1/1996 |
| WO | WO-98/00395 | 1/1998 |
| WO | WO-99/32457 | 7/1999 |
| WO | WO-99/37621 | 7/1999 |
| WO | WO-99/50249 | 10/1999 |
| WO | WO-00/78317 | 12/2000 |
| WO | WO-01/02399 | 1/2001 |
| WO | WO-02/18384 | 3/2002 |
| WO | WO-2004/048375 | 6/2004 |

OTHER PUBLICATIONS

Advisory Action dated Apr. 1, 2009 for U.S. Appl. No. 10/536,028.
Agrez et al., The alpha-v-beta-6 Integrin induces gelatinase B secretion in colon cancer cells, Int. J. Cancer, 81:90-97, 1999.
Angiogenesis and Antiangiogenic Therapy, Curr. Probl. Cancer (2002) 26:1-60.
Antonov et al., Medline Abstract (American Journal of Pathology, 165(1):247-258, Jul. 2004.
Bredereck et al, Liebigs Ann Chem, (1972), 766:73-88.
Brooks et al, Integrin alpha-v-beta-3 antagonists promote tumor regression by inducing apoptosis of angiogenic blood vessels, Cell (1994) 79: 1157-1164.

(Continued)

*Primary Examiner* — Samantha Shterengarts
(74) *Attorney, Agent, or Firm* — Foley & Lardner LLP

(57) ABSTRACT

A subject of the invention is the compounds of formula (I);

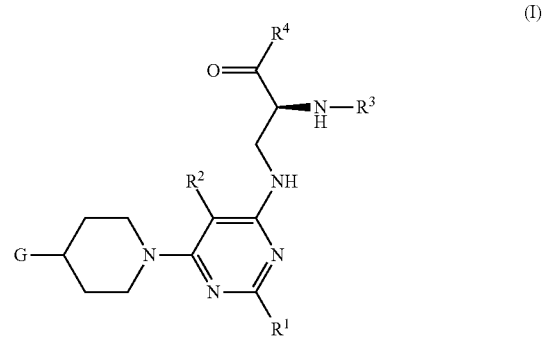

in which $R^1$, $R^2$, $R^3$, $R^4$ and R have the meanings indicated in the description, their preparation process, their use as medicaments having an antagonist activity on the vitronectin receptor and the pharmaceutical compositions containing them.

2 Claims, No Drawings

(56) References Cited

OTHER PUBLICATIONS

Brooks et al., Integrin alpha-v-beta-3: A therapeutic target, DN&P, 10(8):456-461, Oct. 1997.
Brown et al., Stimulation of migration of human aortic smooth muscle cells by vitronectin: implications for atherosclerosis, Cardiovascular Research (1994), 28:1815-1820.
Bundgaard, Novel chemical approaches in pro-drug design, Drugs Future, (1991),16(5):443-458.
Burke et al, Antiangiogenic agents and their promising potential in combined therapy, Critical Reviews in OncologyHematology (2001)39:155-171.
Cherush et al, Definition of Two Angiogenic Pathways by Distinct alpha-v Integrins, Science (1995) 270:1500-2.
English Translation of Japanese Office Action dated Dec. 8, 2009 for Japanese App. No. 2004-554592.
Ettmayer et al, Lessons Learned from Marketed and Investigational Prodrugs, J. of Medicinal Chemistry, 47(10) (2004), pp. 2393-2404.
Evans, Reduction of Aminopyrimidines., Hydropyrimidines: Part III., J. Chem. Soc. (1964), p. 2450-2455.
Fisher et al., Inhibition of osteoclastic bone absorption in vivo by eshistatin, an arginyl-glycyl-aspartyl (RGD)-containing protein, Endocrinology (1993), 132(3):1411-1413.
Fleisher et al., Improved oral drug delivery: solubility limitations overcome by the use produgs, Adv Drug Deliv Rev, (1996), 19:115-130.
Friedlander et al, Definition of two angiogenic pathways by distinct alpha-v integrins, Science (1995), 270:1500-1502.
Gladson et al., Vitronectin Expression in Differentiating Neuroblastic Tumors, American Journal of Pathology, vol. 150, No. 5, pp. 1631-1646, May 1997.
Henry et al, Vitronectin receptor-alpha-v-beta-3 intigren-Antagonists: Chemical and structural requirements for activity and selectivity, Mini Reviews in Medicinal Chemistry, 2:531-542, 2002.
Horton et al., Arg-Gly-Asp (RGD) peptides and the anti-vitronectin receptor antibody 23C6 inhibit dentine resorption and cell spreading by osteoclasts, Exp. Cell. Res. (1991), 195: 368-375.
Interview Summary dated Jan. 22, 2010 for U.S. Appl. No. 12/245,622.
Interview Summary dated Feb. 26, 2009 for U.S. Appl. No. 10/536,028.
Kim et al., Vitronectin-driven Human Keratinocyte Locomotion is Mediated by the alpha-v-beta-5 Integrin Receptor, The Journal of Biological Chemistry, 269(43):26928-26932, Oct. 1994.
Konig et al, Perchloric acid in peptide chemistry, Peptides (1990), p. 143-154.
Kwon, Younggil, Chapter 12—Predicting Pharmacokinetics in Humans, Handbook of Essential Pharmacokinetics, Pharmacodynamics and Drug Metabolism for Industrial Scientists, pp. 208-228, 2001.
Metabolomics, Retrieved online via the Internet [Oct. 16, 2008] URL:www.en.wikipedia.org/wiki/Metabolomics.
Miller et al, Identification and in vivo efficacy of small-molecule antagonists of integrin alpha-v-beta-3 (the vitronectin receptor), DDT vol. 5, No. 9 (2000) 397-408.
Morissette et al, High-throughput crystallization: polymorphs, salts, co-crystals and solvates of pharmeceutical solids, Advanced Drug Delivery Reviews 2004, 56:275-300.
Mousa., Anti-integrin as novel drug-discovery targets: potential therapeutic and diagnostic implications, Current Opinion in Chemical Biology(2002)6:534-541.
Nielsen et al, J Org Chem, (1964), 29:2898-2903.
Nip et al., The role of the Integrin vitronectin receptor, alpha-v-beta-3 in melanoma metastasis, Cancer and Metastasis Reviews, 14:241-252, 1995.
Notice of Allowance dated Mar. 18, 2010 for U.S. Appl. No. 12/245,622.
Notice of Allowance dated Apr. 24, 2009 for U.S. Appl. No. 10/536,028.
Notice of Allowance dated May 6, 2009 for U.S. Appl. No. 11/596,597.
Notice of Allowance dated Aug. 9, 2010 for U.S. Appl. No. 12/541,876.
Notice of Allowance dated Aug. 28, 2009 for U.S. Appl. No. 11/596,597.
Notice of Allowance dated Nov. 3, 2011 for U.S. Appl. No. 12/911,691.
Pytela et al., Arginine-Glycine-Aspartic acid adhesion receptors, Methods in Enzymology (1987) 144:475-489.
Raynal et al., Bone Sialoprotein Stimulates in vitro Bone Resorption, Endocrinology, 137(6):2347-54, 1996.
Safadi et al, Phosphoryloxymethyl carbamates and carbonates—novel water-soluble prodrugs for amines and hindered alcohols, Pharm Res, (1993), 10(9):1350-1355.
Sato et al., Echistatin is a potent inhibitor of bone resorption in culture, J. Cell. Bio. (1990), 111:1713-1723.
Saulnier et al, An efficient method for the synthesis of guanidino prodrugs, Bioorganic & Medicinal Chemistry Letters, (1994), 4(16):1985-1990.
Schvartz et al., Vitronectin, The International Journal of Biochemistry & Cell Biology, 31, pp. 539-544, 1999.
Simone, Oncology: Introduction, Cecil Textbook of Medicine, 20th Edition, 1:1004-1010, 1996.
Stella, V.J., Expert Opinion of Therapeutic Patents, Prodrugs as therapeutics, 14(3):277-280, 2004.
Stilz et al., Discovery of an orally active non-peptide fibrinogen receptor antagonist based on the hydantoin scaffold, J. Med. Chem. (2001), 44:1158-1176.
Testa, B., Prodrug Research: futile or fertile?, Biochemical Pharmacology, (2004) 68:2097-2106.
US Office Action dated Apr. 2, 2008 for U.S. Appl. No. 10/536,028.
US Office Action dated Jun. 5, 2008 for U.S. Appl. No. 11/596,597.
US Office Action dated Oct. 2, 2009 for U.S. Appl. No. 12/245,622.
US Office Action dated Oct. 24, 2008 for U.S. Appl. No. 11/596,597.
US Office Action dated Dec. 8, 2008 for U.S. Appl. No. 10/536,028.
US Office Action dated Dec. 8, 2009 for U.S. Appl. No. 12/541,876.
US Office Action dated Jul. 19, 2011 for U.S. Appl. No. 12/911,691.
US Office Action on dated May 21, 2010 for U.S. Appl. No. 12/541,876.
Varner et al, Integrins and cancer, Current Opinion in Cell Biology, (1996) 8:724-730.
Vippagunta et al, Crystalline Solids, Advance Drug Delivery Reviews (2001), 48:3-26.
Wermuth, C.G., The Practice of Medicinal Chemistry, (1998) 1:274-293—No translation.
Wolff et al, Burger's Medicinal Chemistry and Drug Discovery, vol. 1: Principles and Practice, 5th Ed., pp. 975-977, 1994.
Yasuda et al, An efficient sythesis of an alpha-beta-3 antagonist, J Org Chem, (2004), 69:1959-1966.
Zhao et al, Tumor alpha-v-beta-3 Integrin is a Therapeutic Target for Breast Cancer Bone Metastases, Cancer Res, (2007) 67:5821-5830.

PYRIMIDINE DERIVATIVES WHICH ARE ANTAGONISTS OF THE VITRONECTIN RECEPTOR

RELATED APPLICATIONS

The present application is a continuation of U.S. application Ser. No. 12/911,691, filed Oct. 25, 2010 which is a continuation of U.S. application Ser. No. 12/541,876, filed Aug. 14, 2009 now pending, which is, in turn a continuation of U.S. application Ser. No. 11/596,597, filed Nov. 15, 2006, which, in turn, claims priority from PCT FR2005/001209. filed May 13, 2005, the entire contents of each of which are hereby incorporated by reference herein.

FIELD OF THE INVENTION

A subject of the present invention is new pyrimidine derivatives which are antagonists of the vitronectin receptor, their preparation process, their use as medicaments and the pharmaceutical compositions containing them.

BACKGROUND

Bone is constantly subjected to a dynamic process which includes bone resorption and bone formation. These processes are mediated via specialized cells. Bone formation is the result of the deposit of a mineral matrix by the osteoblasts and bone resorption is the result of the dissolution of this bone matrix by the osteoclasts. The majority of bone disorders are caused by a disturbed equilibrium between bone formation and bone resorption. Osteoporosis is characterized by a dry loss of this bone matrix. An activated mature osteoclast resorbs the bone after adhesion to the bone matrix via the secretion of proteolytic enzyme, and protons inside the adhesion zone, resulting in depressions or hollows in the bone surface which appear when the osteoclast detaches itself from the bone.

Studies have shown that the fixation of the osteoclast on the bone is mediated by receptors: the integrins. Integrins are a superfamily of receptors mediating the cell/cell and more particularly cell/matrix adhesion processes, including in particular $\alpha_{IIb}\beta_3$ as a blood platelet receptor (fibrinogen) and $\alpha_v\beta_3$ as vitronectin receptor. The peptides containing the RGD unit as well as the anti $\alpha_v\beta_3$ antibodies are known for their ability to inhibit resorbtion of dentin and prevention of osteoclast adhesion on the mineralized matrices (Horton et al. Exp. Cell. Res. (1991), 195, 368). The peptide Echistatine, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411).

The $\alpha_v\beta_3$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta_3$ receptors expressed in the membrane of the osteoclasts are the basis of the adhesion/resorption process, contribute to the organization of the cell cytoskeleton, and are involved in osteoporosis. The $\alpha_v\beta_3$ receptors expressed in the smooth muscle cells of the aorta, stimulate their migration towards the neointima, which leads to the formation of arteriosclerosis and the occurrence of post-angioplastic restenosis (Brown et al., cardiovascular Res. (1994), 28, 1815). The endothelial cells secrete growth factors which are mitogens for the endothelium and can contribute to the formation of new blood vessels (Angiogenesis).

The antagonists of $\alpha_v\beta_3$ integrin can therefore lead to a regression of cancerous tumors by inducing apoptosis of the angiogenic blood vessels. (Brook et al. Cell (1994) 79, 1157).

Cheresh et al (Science 1995, 270, 1500) have described anti-$\alpha_v\beta_3$ antibodies or antagonists of the $\alpha_v\beta_3$ receptor which inhibit the process of angiogenesis induced by bFGF in the rat eye, a property which can be used for the treatment of retinopathies, in particular in diabetics.

The Patent Application WO-A-94/12181 describes aromatic or non-aromatic substituted systems and WO-A-94/08577 describes substituted heterocycles as antagonists of the fibrinogen receptor and inhibitors of platelet aggregation. EP-A-528586 and EP-A-528587 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. WO9800395, WO99/32457 and WO99/37621 describe tyrosine derivative antagonists of the vitronectin receptor. EP0820991 claims cycloalkyl derivatives as antagonists of the vitronectin receptor.

BRIEF DESCRIPTION OF THE INVENTION

A subject of the invention is the pyrimidine derivatives of general formula (I):

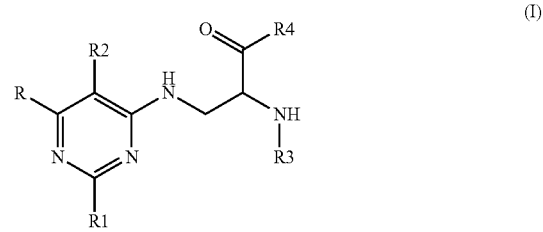

in which R, $R^1$, $R^2$, $R^3$ and $R^4$ have the meanings indicated hereafter, as well as their isomeric forms and their mixtures and their physiologically acceptable salts. The compounds of formula (I) are compounds having a pharmacological activity and therefore can be used as medicaments. They are antagonists of the vitronectin receptor and cell adhesion inhibitors and they inhibit bone resorption mediated by the osteoclasts. They are therefore useful for the therapeutic or prophylactic treatment of diseases which are caused at least in part by an undesirable increase in bone resorption, for example osteoporosis. A subject of the invention is also the processes for preparing the compounds of formula (I), their use, in particular as a medicament, and the pharmaceutical compositions containing them.

Other investigations have made it possible to show that the acylguanidine derivatives of formula (I) show marked activity as antagonists of the vitronectin receptor and of bone resorption mediated via the osteoclasts.

DETAILED DESCRIPTION OF THE INVENTION

A subject of the invention is the compounds of formula (I):

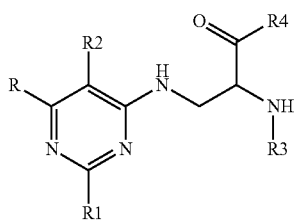

(I)

in all their isomeric forms, alone or in the pure state or in the form of a mixture of these forms, as well as their physiologically acceptable addition salts, in which I)
R represents
an —X-alk-Het radical for which X is an oxygen or sulphur atom or an —NR'— radical for which R' is a hydrogen atom or a linear or branched alkyl radical containing 1 to 4 carbon atoms, alk represents a linear or branched alkyl radical containing 1 to 4 carbon atoms and Het represents a monocyclic or polycyclic system, each ring being constituted by 4 to 10 aromatic or non-aromatic members, and being able to contain 1 to 4 heteroatoms chosen from nitrogen, oxygen or sulphur and being able to be itself substituted by one or more $R^o$ groups defined hereafter, or a radical for which G represents a aromatic or non-aromatic, monocyclic or polycyclic heterocyclyl radical comprising 5 to 10 members and in which at least one of the rings contains 1 to 4 nitrogen atoms said heterocyclyl radical being able to be itself optionally substituted by a $(C_1-C_8)$alkylamino radical the alkyl part of which in linear or branched chain can be substituted by a phenyl or heterocyclyl radical with 5 or 6 members containing 1 to 4 heteroatoms chosen from nitrogen, oxygen or sulphur, and n represents 1 or 2, or

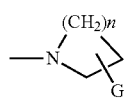

(Ia)

a radical for which G represents a aromatic monocyclic heterocyclyl radical with 5 or 6 members containing 1 to 4 nitrogen atoms and substituted by an alkyl$(C_1-C_6)$amino radical

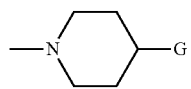

(Ib)

the alkyl radical of which can itself be substituted by a phenyl or aromatic monocyclic heterocyclyl radical with 5 or 6 members, containing a heteroatom chosen from nitrogen, oxygen or sulphur;

—$R^1$ represents a hydrogen atom; a $(C_5-C_{14})$-aryl; $(C_5-C_{14})$-aryl-$(C_1-C_4)$-alkyl- group; an amino radical non-substituted, monosubstituted or disubstituted by an alkyl radical and/or an acyl radical containing 1 to 4 carbon atoms;

—$R^2$ represents a hydrogen atom; a halogen atom; a nitro group; an alkyl radical containing 1 to 4 carbon atoms; an amino radical non-substituted or monosubstituted or disubstituted by an alkyl radical and/or an acyl radical containing 1 to 4 carbon atoms; a —$(CH_2)_{0-2}$—$CO_2R^5$ group; or a —$(CH_2)_{0-2}$—$OR^5$ group;

—$R^3$ represents
a hydrogen atom
a —$CO_2R^5$ radical,
an —$SO_2R^5$ radical or
a monocyclic or polycyclic system, each ring being constituted by 4 to 10 aromatic or non-aromatic members, the ring or at least one of the rings containing 1 to 4 heteroatoms chosen from N, O or S, substituted or non-substituted by one or more $R^o$ radicals, —$R^4$ represents OH; $(C_1-C_8)$-alkoxy-; $(C_5-C_{14})$-aryl-$(C_1-C_4)$-alkyloxy-; $(C_5-C_{14})$-aryloxy-; $(C_3-C_{12})$-cycloalkyloxy; $(C_3-C_{12})$-cycloalkyl-$(C_1-C_4)$-alkyloxy-; $(C_1-C_8)$-alkylcarbonyloxy-$(C_1-C_4)$-alkyloxy-; $(C_5-C_{14})$-aryl-$(C_1-C_4)$-alkylcarbonyloxy-$(C_1-C_4)$alkyloxy-; $(C_1-C_8)$dialkylaminocarbonylmethyloxy-; $(C_5-C_{14})$-aryl-$(C_1-C_4)$-dialkylaminocarbonylmethyloxy-; an amino radical non-substituted or monosubstituted or disubstituted by a $(C_1-C_4)$-alkyl and/or $(C_5-C_{14})$-aryl and/or $(C_5-C_{14})$-aryl-$(C_1-C_4)$-alkyl-radical and/or a $(C_1-C_5)$-acyl radical; or the remainder of a D or L amino acid;

—$R^5$ represents $(C_1-C_8)$-alkyl; $(C_5-C_{14})$-aryl; $(C_5-C_{14})$-aryl-$(C_1-C_4)$-alkyl-; $(C_3-C_{12})$-cycloalkyl or $(C_3-C_{12})$-cycloalkyl-$(C_1-C_4)$-alkyl-, bicycloalkyl-$(C_1-C_4)$-alkyl-, tricycloalkyl-$(C_1-C_4)$-alkyl-, the said aryl, alkyl, cycloalkyl, bicycloalkyl and tricycloalkyl radicals being non-substituted or substituted by one or more $R^o$ groups;

$R^o$ represents halogen; amino; nitro; hydroxyl, $(C_1-C_4)$-alkyloxy-; $(C_1-C_4)$-alkylthio-; $(C_1-C_4)$-alkylsulphonyl-; carboxy; $(C_1-C_4)$-alkyloxycarbonyl-; $(C_1-C_8)$-alkyl non-substituted or substituted by one or more halogen atoms, $(C_5-C_{14})$-aryl, $(C_5-C_{14})$-aryl-$(C_1-C_4)$-alkyl-; $(C_5-C_{14})$-aryl-$(C_1-C_4)$-alkyloxy-; $(C_5-C_{14})$-heterocyclyl;

or
II)
—R represents a

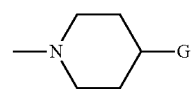

(Ib)

radical
for which G is chosen from the following radicals:
Het-NH—CO—;
Het-NH—CH$_2$—,
Het-, Het represents a monocyclic or polycyclic system, each ring being constituted by 4 to 10 aromatic or non-aromatic members, the ring or at least one of the rings containing 1 to 4 nitrogen atom, and being able to itself be substituted or non-substituted by one or more $R^o$ groups;

—$R^1$ represents an alkyl radical containing 1 to 4 carbon atoms in linear or branched chain; a cycloalkyl radical containing 3 to 6 carbon atoms; or an alkyloxy or alkylthio radical the alkyl part of which contains 1 to 4 carbon atoms in linear or branched chain;

—$R^2$, $R^3$, $R^4$ and $R^5$ are defined as previously in I);
—$R^o$ is defined as previously in I);
or III)
R is defined as previously in II);
$R^1$, $R^3$, $R^4$ and $R^5$ are defined as previously in I);
$R^2$ represents a hydroxymethyl radical, a formyl radical or a disubstituted amino radical the substituents of which form together with the nitrogen atom to which they are attached, a saturated or unsaturated heterocycle containing 4 to 6 members; and
$R^o$ is defined as previously in I);
or IV)
R is defined as previously in II);
$R^1$, $R^2$, and $R^4$ are defined as previously in I);
$R^3$ represents
a linear or branched $(C_1-C_4)$alkyl or $(C_2-C_4)$alkenyl radical, optionally substituted by an aryl or mono or polycyclic heterocyclyl radical with 4 to 10 members, themselves being able to be substituted by one or more radicals chosen from hydroxy, $(C_1-C_4)$alkyloxy, amino, $(C_1-C_4)$alkylamino, $(C_1-C_4)$-dialkylamino, phenyl, cyanophenyl or monocyclic heterocyclyl containing 1 to 4 heteroatoms chosen from nitrogen, oxygen or sulphur;
a —$COR'^5$ radical,
a —$CO_2R^5$ radical for which
$R^5$ represents $(C_1-C_8)$-alkyl; $(C_5-C_{14})$-aryl; $(C_5-C_{14})$-aryl-$(C_1-C_4)$-alkyl-; $(C_3-C_{12})$-cycloalkyl or $(C_3-C_{12})$-cycloalkyl-$(C_1-C_4)$-alkyl-, bicycloalkyl-$(C_1-C_4)$-alkyl-, tricycloalkyl-$(C_1-C_4)$-alkyl-, the said aryl, alkyl, cycloalkyl, bicycloalkyl and tricycloalkyl radicals being non substituted or substituted by one or more $R^o$ groups chosen from $(C_1-C_4)$-alkylsulphonyl-; $(C_5-C_{14})$-aryl-$(C_1-C_4)$-alkyloxy- or $(C_5-C_{14})$-heterocyclyl,
an —$SO_2R'''^5$ radical,
—$R'^5$ represents $(C_1-C_8)$-alkyl substituted by a radical as defined for $R^5$ or by a $(C_5-C_{14})$aryloxy radical, the aryl or cycloalkyl radicals themselves being able to be substituted by one or more $R^o$ radicals; or
$R'^5$ represents a cycloalkyl, aryl or mono or polycyclic heterocyclyl radical optionally substituted by trifluoromethylalkyloxy or $(C_1-C_{10})$-aryl radicals; or
$R'^5$ represents $(C_1-C_4)$alkylamino; $(C_3-C_8)$cycloalkylamino; arylamino or heterocyclylamino the aryl or heterocyclyl part of which are mono or polycyclic, these $R'^5$ radicals being able to themselves be substituted by a halogen atom, a nitro, amino, $(C_1-C_4)$alkyloxy, $(C_1-C_4)$alkyloxycarbonyl, aryl or arylalkyl radical the alkyl part of which contains 1 to 4 carbon atoms in linear or branched chain; and
$R'''^5$ represents a $(C_1-C_4)$alkylamino or di$(C_1-C_4)$alkylamino radical the alkyl parts of which can together form a heterocycle with 5 to 7 members, with the nitrogen atom to which they are linked, an arylamino, aralkyl$(C_1-C_4)$amino or heteroaralkyl$(C_1-C_4)$amino radical the aryl or heteroaryl radical of which is mono or polycyclic and comprises 5 to 10 members, the heteroaryl radical being able to contain 1 to 4 heteroatoms chosen from nitrogen, oxygen or sulphur; and
$R^o$ is defined as previously in I);
or V)
R, $R^2$, $R^3$ and $R^4$ are defined as previously in I);
$R^1$ is defined as previously in II);
or VI)
R, $R^1$, $R^3$ and $R^4$ are defined as previously in II);
$R^2$ is defined as previously in III);
or VII)
R, $R^1$ and $R^2$ are defined as previously in I);
$R^4$ is defined as previously in I); and
$R^3$ is defined as previously in IV);
or VIII)
R, $R^1$ and $R^2$ are defined as previously in II);
$R^4$ is defined as previously in I); and
$R^3$ is defined as previously in IV);
or IX)
R and $R^3$ are defined as previously in I);
$R^4$ is defined as previously in I);
$R^1$ is defined as previously in II); and
$R^2$ is defined as previously in III);
or X)
R and $R^2$ are defined as previously in I);
$R^4$ is defined as previously in I);
$R^1$ is defined as previously in II); and
$R^3$ is defined as previously in IV);
or XI)
R and $R^1$ are defined as previously in II);
$R^4$ is defined as previously in I);
$R^2$ is defined as previously in III); and
$R^3$ is defined as previously in IV);
or XII)
R and $R^4$ are defined as previously in I);
$R^1$ is defined as previously in II);
$R^2$ is defined as previously in III);
$R^3$ is defined as previously in IV);
on condition that the above radicals cannot simultaneously have the meaning
R represents a radical (Ib) in which G is 1,2,3,4-tetrahydro-1,8-naphthyridin-7-yl,
$R^1$ represents methyl,
$R^2$ represents methyl,
$R^3$ represents benzyloxycarbonyl and
$R^4$ represents OH or t.butoxy.

All the radicals which can be found several times in the compounds of formula (I), such as for example the radical $R^o$, are independent of each other and can be identical or different.

It is understood that the alkyl radicals or portions can be linear or branched.

The cycloalkyl radicals can be monocyclic, bicyclic or tricyclic. By way of example the monocyclic radicals can be chosen from cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclooctadecyl which, if appropriate, can be substituted for example by an alkyl containing 1 to 4 carbon atoms in linear or branched chain. As substituted monocyclic cycloalkyl radicals, there can be mentioned in particular 4-methylcyclohexyl and 2,3-dimethylcyclohexyl.

The bicycloalkyl and tricycloalkyl radicals can be non-substituted or substituted in any position, for example by one or more oxo radicals and/or 1 or more identical or different alkyl radicals such as for example methyl, ethyl or isopropyl, preferably methyl. The junction bond of the bi or tricyclic radical can be situated in all positions of the molecule. The bond can be situated at the level of a bridging carbon atom or one of the other carbon atoms. This bond can also be in any position from the point of view of the stereochemistry, for example exo or endo. As an example of bicycloalkyl or tricycloalkyl radicals, there can be mentioned camphanyl, bornyl, adamantyl such as 1-adamantyl or 2-adamantyl, caranyl, epiisobornyl, epibornyl, norbornyl or norpinanyl.

By halogen is meant fluorine, chlorine, bromine or iodine.

By the term $(C_5-C_{14})$-aryl is meant:

either the heterocyclic $(C_5-C_{14})$-aryl (or $(C_5-C_{14})$-heteroaryl) radicals, in which one or more carbon atoms of the ring are replaced by a heteroatom such as nitrogen, oxygen or sulphur, or the carbocyclic $(C_6-C_{14})$-aryl radicals.

Among the carbocyclic $(C_6-C_{14})$-aryl radicals, there can be mentioned phenyl, naphthyl, anthryl or fluorenyl and quite particularly 1-naphthyl, 2-naphthyl and phenyl.

Unless indicated otherwise, the aryl radicals, in particular phenyl, can be non-substituted or substituted by one or more identical or different radicals chosen from $(C_1-C_8)$-alkyl, in particular $(C_1-C_4)$-alkyl, hydroxyl, $(C_1-C_8)$-alkyloxy, $(C_1-C_8)$-alkylthio, halogen chosen from fluorine, chlorine and bromine, nitro, amino, $(C_1-C_4)$-alkylamino, di-$(C_1-C_4)$-alkylamino, trifluoromethyl, methylenedioxy, cyano, carbamoyl, $(C_1-C_4)$-alkylcarbamoyl, di-$(C_1-C_4)$-alkylcarbamoyl, carboxy, $(C_1-C_4)$-alkoxycarbonyl, phenyl, phenoxy, benzyl and benzyloxy.

In the case of a monosubstituted phenyl radical, the position of the substituents is immaterial, preferably it is substituted in position 3 or 4. In the case where the phenyl is di-substituted, the position of the substituents is immaterial. Preferably the 2 substituents are in position 3,4. When the phenyl is tri-substituted the position of the substituents is immaterial. Similarly, the naphthyl radicals or other aryl radicals can be substituted in any position.

When the $(C_5-C_{14})$-aryl group represents a monocyclic or polycyclic aromatic system in which 1 to 4 carbon atoms of the ring are replaced by identical or different heteroatoms chosen from nitrogen, oxygen and sulphur, or when the meaning heteroaryl is used, there can be mentioned by way of example the pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, naphthyridinyl, quinoxalinyl, quinazolinyl, cinnolinyl, β-carbolinyl groups, or also the benzo-condensed, cyclopenta-, cyclohexa-, or cyclohepta-condensed derivatives of these radicals such as for example tetrahydroquinokyl or tetrahydronaphthyridinyl. The heterocyclic system can be substituted by the substituents mentioned previously for the aryl-carbocyclic system.

The heterocyclyl radicals are, unless mentioned particularly, mono, or polycyclic aromatic or not aromatic, and can be in particular chosen, in a non-limitative manner, from pyrrolyl, pyrazolyl, imidazolyl, triazinyl, tetrazolyl, thienyl, furyl, thiazolyl, isothiazolyl, oxazolyl, isoxazolyl, pyridyl, pyrazinyl, pyrimidinyl, pyridazinyl, pyrannyl, thiopyrannyl, indolyl, isoindolyl, benzofurannyl, isobenzofurannyl, benzothienyl, indazolyl, indolizinyl, benzimidazolyl, imidazopyridyl, benzopyrimidinyl, benzoxazolyl, benzothiazolyl, oxazolopyridyl, quinolyl, isoquinolyl, quinalozinyl, quinoxalinyl, naphthyridinyl, naphthooxazolyl, naphthothiazolyl, pyrrolidinyl, pyrrolinyl, imidazolidinyl pyrazolidinyl, pyrazolinyl, piperidinyl, piperazinyl, dihydropyrannyl, tetrahydropyrannyl, dihydrothiopyrannyl, tetrahydrothiopyrannyl, morpholinyl, thiomorpholinyl, indolinyl, chromannyl, tetrahydroquinolyl, tetrahydrobenzimidazolyl, tetrahydrobenzopyrimidinyl, tetrahydronaphthyridinyl, dihydropyrrolopyridine, quinuclidinyl.

The optically active carbon atoms contained in the compounds of formula (I) can independently of each other have the R configuration or the S configuration.

The compounds of formula (I) can be in the form of pure enantiomers or pure diastereoisomers or in the form of a mixture of enantiomers, for example in the form of racemates or mixtures of diastereoisomers.

A subject of the present is therefore the pure enantiomers, the mixtures of these enantiomers, the pure diastereoisomers and the mixtures of these diastereoisomeres.

The invention comprises the mixtures of two or more than two stereoisomers of formula (I) and all the ratios of these stereoisomers within said mixtures.

The compounds of formula (I) can if appropriate be present in the form of E isomers or Z isomers. Therefore a subject of the present invention is the pure E isomers, the pure Z isomers and the E/Z mixtures according to any ratio.

The stereoisomers as well as the E and Z isomers can be separated into pure forms according to known methods, for example by chromatography, chiral phase chromatography or by crystallization.

The physiologically acceptable salts of the compounds of formula (I) are in particular pharmaceutically useable or non-toxic or physiologically useable salts.

When the compounds of formula (I) contain an acid group such as carboxylic acid, the salts can be for example salts of alkali or alkaline-earth metals such as the salts of sodium, potassium, magnesium, calcium, addition salts with physiologically acceptable amines such as for example triethylamine, ethanolamine or tris-(2-hydroxyethyl)amine or with ammonia and also the physiologically acceptable quaternary ammonium salts.

When the compounds of formula (I) contain a basic group, they can form addition salts with acids for example with mineral acids such as hydrochloric, sulphuric, phosphoric acid or with carboxylic acids such as acetic, trifluoracetic, citric, benzoic, maleic, fumaric, tartric, methanesulphonic or p.toluenesulphonic acid.

The compounds of formula (I) which comprise a basic group and an acid group, can be present in the form of zwitterions (betaines), which are also included in the present invention.

If appropriate a physiologically acceptable anion $Q^-$ can be contained in the compounds of formula (I) containing a charged ammonium group. It is preferably a monovalent anion or a polyvalent anion equivalent of a non-toxic, physiologically acceptable organic or mineral acid and in particular pharmaceutically acceptable, for example the anion or an anion equivalent of one of the acids mentioned above which are of use for the formation of addition salts.

$Q^-$ can be for example one of the anions (or anion equivalent) of a group chosen from chlorine, sulphate, phosphate, acetate, trifluoracetate, citrate, benzoate, maleate, fumarate, tartrate, methanesulphonate and p.toluenesulphonate.

The salts of the compounds of formula (I) can be obtained by the ordinary methods known to a person skilled in the art, for example by combining a compound of formula (I) with an organic or inorganic acid or a base in an appropriate solvent or a dispersant or from another salt by cation or anion exchange.

The invention also includes all the salts of the compounds of formula (I) which, due to their low physiological acceptability, cannot be used directly as a medicament, but can be used as intermediate products for the purification, or for implementing subsequent chemical modifications at the level of the compounds of formula (I) or as starting products for the preparation of physiologically acceptable salts.

The present invention also includes all the solvates of the compounds of formula (I) for example the hydrates, the solvates formed with alcohols, and all the derivatives of the compounds of formula (I), for example the esters, prodrugs and other physiologically acceptable derivatives, as well as the metabolites of the compounds of formula (I).

The prodrugs of the compounds of formula (I), namely the chemically modified derivatives of the compounds of formula (I) in order to obtain improved properties in the desired manner, are known to a person skilled in the art.

For more information on the type of prodrug envisaged in the present invention, the following works can be mentioned: Fleicher et al., Advanced Drug Delivery Review 19 (1996) 115-130; Design of prodrugs, H. Bundgaard, Ed., Elsevier, 1985; H. Bungaard, Drugs of the Future 16 (1991) 443; Saulnier et al. Bioorg. Med. Chem. Lett. 4 (1994) 1985; Safadi et al. Pharmaceutical Res. 10 (1993) 1350. Among the suitable prodrugs of the compounds of formula (I) there can be preferably mentioned:

the prodrugs in the form of esters of carboxylic groups, the prodrugs in the form of acyl and carbamate for the groups containing an acylable nitrogen such as the amino groups.

In the acylated prodrugs or in the form of carbamate, one or more times, for example twice, a hydrogen atom situated on the nitrogen atom is replaced by an acyl or carbamate group. Among the preferred acyl or carbamate groups, there can be mentioned the $R^6CO—$, $R^7OCO—$ groups, in which $R^6$ is a hydrogen or a $(C_1-C_{18})$-alkyl, $(C_3-C_{14})$-cycloalkyl, $(C_3-C_{14})$-cycloalkyl-$(C_1-C_8)$-alkyl, $(C_5-C_{14})$-aryl radical, in which 1 to 5 carbon atoms can be remplaced by heteroatoms such as N, O, S or $(C_5-C_{14})$-aryl-$(C_1-C_8)$alkyl, in which 1 to 5 carbon atoms in the aryl part can be remplaced by heteroatoms such as N, O, S and $R^7$ has the same values as $R^6$ with the exception of representing hydrogen.

A more particular subject of the invention is the compounds of formula (I) in which G represents a Het, Het-NHCO—, or Het-NH—CH$_2$— group in which Het represents:

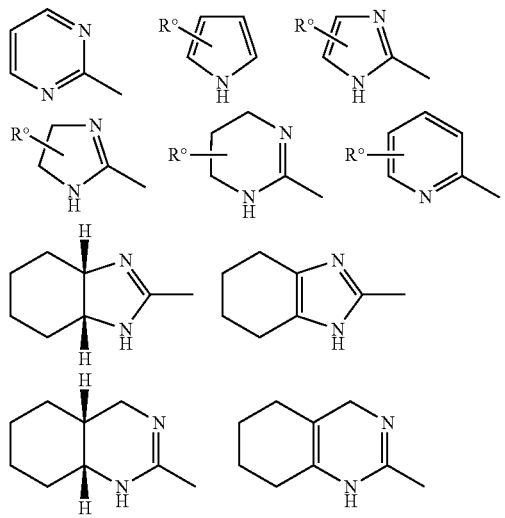

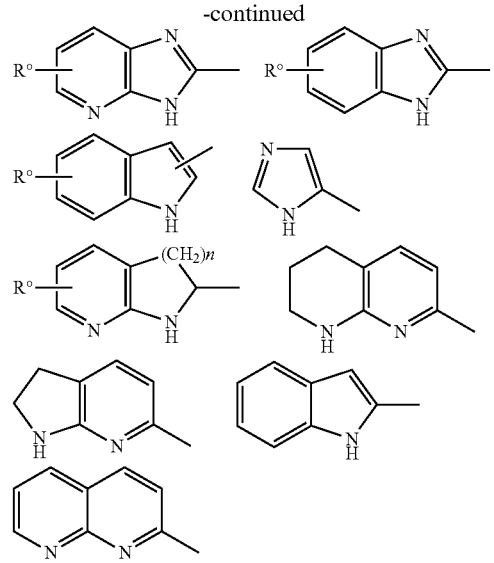

A more particular subject of the invention is the compounds of formula (I) as defined above in which $R^3$ is a benzyloxycarbonyl group, or in which $R^3NH—$ forms an amide or urea function as well as their pharmaceutically acceptable addition salts.

A more particular subject of the invention is the compounds of formula (I) as defined above in which $R^2$ is a hydrogen, an alkyl radical containing 1 to 4 carbon atoms, particularly methyl and ethyl, a hydroxymethyl radical or a fluorine atom as well as their pharmaceutically acceptable addition salts.

A more particular subject of the invention is the compounds of formula (I) as defined above in which $R^1$ is an alkyl radical containing 1 to 4 carbon atoms in linear or branched chain, or cycloalkyl containing 3 to 6 carbon atoms.

A more particular subject of the invention is the compounds of formula (I) as defined above in which:

G represents

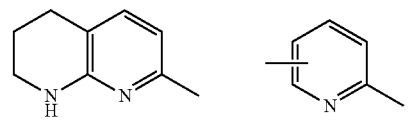

as well as their pharmaceutically acceptable addition salts.

A subject of the present invention is also a process for the preparation of the compounds of formula (I). The compounds can generally be prepared, for example by convergent synthesis by coupling two or more fragments which can be derived by retrosynthesis of the compounds of formula (I). In order to avoid the functional groups leading to undesirable or secondary reactions during each stage of the synthesis, it may be advantageous or necessary beforehand, at certain phases of the synthesis of the compounds of formula (I), to introduce the functional groups in the form of precursors which are subsequently converted to desired functional groups or to temporarily protect these functional groups according to the methods known for putting in place and eliminating protective radicals, which do not alter the remainder of the molecule; in particular according to Greene, Wuts protective Group in Organic Synthesis, Wiley (1991).

According to the invention, the products of general formula (I) can be prepared according to the following diagram:

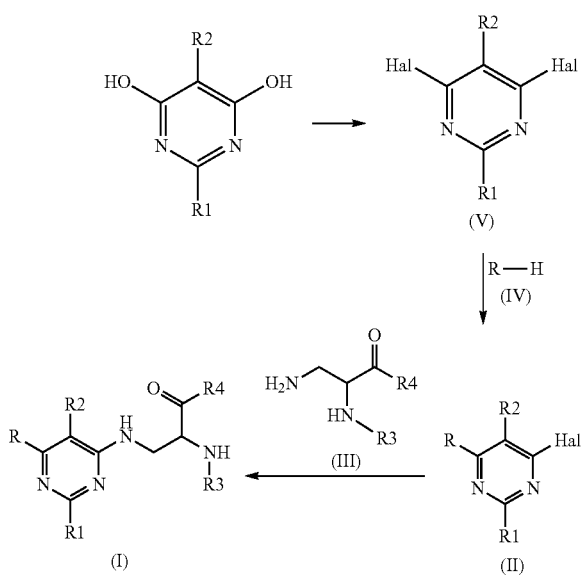

in which $R^1$, $R^2$, $R^3$, $R^4$ and R are defined as previously in I) to XII) and Hal represents a halogen atom, preferably chlorine or bromine.

According to the invention, the process for the preparation of the products of formula (I) consists of a) the action of a pyrimidine derivative of formula (II)

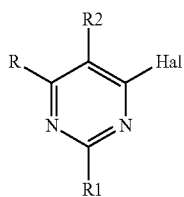

in which $R^1$, $R^2$, R and Hal are as defined previously, on an amine of formula (III)

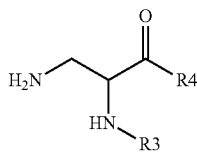

in which $R^3$ and $R^4$ are defined as previously, either in the presence of a strong base, or by catalysis with palladium, b) then when one wishes to obtain a product for which the R radical is saturated or partially saturated, the product of general formula (I) is, if appropriate, subjected to a hydrogenation stage, c) then, if appropriate, when one wishes to obtain a pyrimidine derivative of general formula (I) for which $R^2$ is hydroxymethyl, reduction of the corresponding derivative for which $R^2$ represents a formyl radical, d) and/or if appropriate, when G represents a heterocyclyl radical carrying a substituted amino radical, substitution of the corresponding product carrying a primary amine function on the heterocyclyl radical, e) then, if appropriate, cleavage of the $R^3$—NH— function of the product of general formula (I) in order to regenerate the free amine, and condense an $R^3$ radical of —$CO_2$—$R^5$, —CO—$R'^5$, —$SO_2$—$R^5$ or —$SO_2$—$R''^5$ structure or optionally substituted alkyl, f) and/or optionally hydrolysis and/or esterification or amidification and/or salification of the pyrimidine derivative obtained.

The reaction of the pyrimidine of formula (II) with the amine of formula (III) is generally carried out in the presence of a hindered strong base such as diisopropylethylamine under reaction conditions known to a person skilled in the art in the implementation of nucleophilic substitution. Preferably the operation takes place in the presence of an amide (dimethylacetamide, dimethylformamide for example), at a temperature comprised between 90° C. and the reflux temperature of the reaction mixture. Moreover the $COR^4$ group is preferably chosen from the hindered ester groups such as for example tertbutoxycarbonyl. It is also possible to operate by catalysis with palladium (for example tris(dibenzylideneacetone) dipalladium) in the presence of cesium fluoride, at the reflux temperature of the reaction mixture. It is understood that the functions which could interfere with the reaction are protected. The protection and release of these functions are carried out according to the usual methods which do not alter the remainder of the molecule.

When one wishes to obtain a product for which the R radical is saturated or partially saturated, the hydrogenation reaction is carried out in the presence of platinum oxide, in a solvent such as an alcohol (ethanol, methanol for example), under atmospheric pressure.

When one wishes to obtain a pyrimidine derivative of general formula (I) for which $R^2$ is hydroxymethyl, the reduction of the corresponding derivative for which $R^2$ represents a formyl radical, is advantageously carried out using an alkaline borohydride (sodium borohydride), in a solvent such as an alcohol (ethanol, methanol for example), at a temperature comprised between 10 and 40° C., preferably at ambient temperature.

When one wishes to obtain a pyrimidine derivative of general formula (I) for which G (in R) represents a heterocyclyl radical carrying a substituted amino radical, the substitution of the corresponding product carrying a primary amine function on the heterocyclyl radical is carried out by the action of the corresponding aldehyde, in reducing medium, in particular in the presence of a borohydride such as for example an alkali metal triacetoxyborohydride. The reaction is carried out in an organic solvent such as a chlorinated solvent (dichloromethane, dichlorethane for example), at a temperature comprised between 10 and 40° C., preferably at ambient temperature.

The condensation of $R^3$ radicals of —$CO_2$—$R^5$, —CO—$R'^5$, —$SO_2$—$R^5$ or —$SO_2$—$R''^5$ structure on the free amine, is carried out by the action of a reactive derivative or the chloride of carboxylic acid or sulphonic acid, in the presence of a nitrogenous base (such as for example pyridine), in a chlorinated organic solvent (dichloromethane, dichlorethane, chloroform for example), at a temperature comprised between 10 and 40° C., preferably at ambient temperature. When $R'^5$ is a substituted amino radical, the condensation is carried out using the corresponding isocyanate in an organic solvent such as an ether (tetrahydrofuran for example), at a temperature comprised between 10 and 40° C., preferably at ambient temperature.

The condensation of $R^3$ radicals of optionally substituted alkyl structure is carried out by the action of the corresponding aldehyde, in reducing medium, in particular in the presence of a borohydride such as for example an alkali metal triacetoxyborohydride. The reaction is carried out in an organic solvent such as an ether (tetrahydrofuran for example), at a temperature comprised between 10 and 40° C., preferably at ambient temperature.

The hydrolysis reaction in order to obtain an acid derivative ($COR^4=CO_2H$), the esterification reaction in order to obtain an ester or a prodrug (particularly $COR^4$=alkyloxycarbonyl or aryloxycarbonyl from the corresponding acid) or the amidification reaction ($COR^4$=mono or disubstituted aminocarbonyl from the corresponding acid) are carried out according to the usual methods known to a person skilled in the art.

In particular the hydrolysis is carried out in acid medium, in the presence of trifluoracetic acid for example, in a halogenated organic solvent such as dichloromethane for example.

If necessary, the conversion to physiologically acceptable salts is carried out by processes known to a person skilled in the art.

The pyrimidine derivatives of formula (II) can be prepared by the action of a product of formula (IV) in which R is defined as previously, on a dihalogenated pyrimidine derivative of general formula:

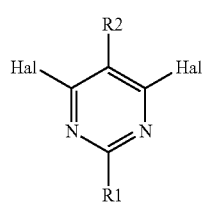

(V)

in which $R^1$, $R^2$ and Hal are defined as previously.

The reaction is advantageously carried out in the presence of a hindered strong base, at the reflux temperature of the reaction mixture. The operation is carried out under the conditions described hereafter in the examples and in particular in the presence of a hindered amine such as diisopropylethylamine, in an amide such as dimethylacetamide for example. It is understood that the functions which could interfere with the reaction are protected. The protection and release of these functions are carried out according to the usual methods which do not alter the remainder of the molecule.

The preparation of the dihalogenated pyrimidines of general formula (V) can be carried out according to or by analogy with the methods described hereafter in the examples.

The compounds of formula (I) are compounds having a pharmacological activity and can thus be used as medicaments in particular in the treatment or prevention of diseases of the bone, tumorous diseases as well as cardiovascular disorders.

Therefore a subject of the present invention is the compounds of formula (I) and/or their physiologically acceptable salts as a medicament.

The compounds of formula (I) as well as their physiologically acceptable salts and their prodrugs can be administered to animals, preferably mammals and in particular human beings as therapeutic or prophylactic medicaments.

They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts as active ingredient as well as current and pharmaceutically inert supports and/or additives.

The pharmaceutical compositions according to the invention allow enteral or parenteral administration; they contain an effective dose of at least one compound of formula (I) and/or its physiologically acceptable salts as active ingredient as well as one or more pharmaceutically inert supports and/or one or more usual additives.

Therefore a subject of the invention is the pharmaceutical compositions containing a compound of formula (I) in the pure state or in the presence of one or more excipients.

The medicaments can be administered orally, for example in the form of pills, tablets, coated tablets, film-encased tablets, granules, gelatin capsules and soft capsules, solutions, syrups, emulsions, suspensions or aerosol mixtures.

The administration can however be carried out by rectal route, for example in the form of suppositories, by parenteral route, for example in the form of injectable solutions, infusions, microcapsules or implants, by percutaneous route, for example in the form of an ointment, solutions, pigments or colorants, by transdermal route in the form of patches, or by other routes such as in the form of an aerosol or nasal spray.

The pharmaceutical preparations according to the invention are prepared according to methods known per se, pharmaceutically inert organic or inorganic supports, being able to be added to the compounds of formula (I) and/or their physiologically acceptable salts.

For the production of pills, tablets, coated tablets and hard gelatin capsules, it is possible to use for example lactose, corn starch or its derivatives, talc, stearic acid or its salts, etc. Suitable supports for soft gelatin capsules or for suppositories are for example fats, waxes, semi-solid or liquid polyols, natural or modified oils, etc. Appropriate vehicles for the preparation of solutions, for example injectable solutions, emulsions or syrups are for example water, alcohols, glycerol, polyols, sucrose, inverted sugars, glucose, vegetable oils, etc. Suitable supports for microcapsules or implants are for example glyoxilic acid and lactic acid copolymers. The pharmaceutical preparations normally contain from 0.5% to 90% by weight of compounds of formula (I) and/or their physiologically acceptable salts.

In addition to the active ingredients and supports, the pharmaceutical preparations can contain additives such as, for example, diluting agents, disintegration agents, binding agents, lubricants, wetting agents, stabilizers, emulsifiers, preservatives, sweetening agents, colouring agents, flavouring or aromatizing agents, thickeners, buffering agents, and also solvents or solubilizing agents or agents to obtain a delayed release effect and also salts for modifying the osmotic pressure, coating agents or antioxidants.

They can also contain two or more compounds of general formula (I) and/or their physiologically acceptable salts. Moreover, in addition to at least one or more compounds of general formula (I) and/or their physiologically acceptable salts, they can contain at least one or more other active ingredients which can be used for therapeutic or prophylactic uses.

The pharmaceutical preparations (pharmaceutical compositions) normally contain 0.2 to 500 mg, and preferably 1 to 200 mg of the compound of formula (I) and/or their physiologically acceptable salts and/or their prodrugs.

The compounds of formula (I) are quite particularly antagonists of the vitronectin receptors and are therefore capable for example of inhibiting the adhesion of osteoclasts on the surface of the bone and thus bone resorption by the osteoclasts.

The action of the compounds of formula (I) can be demonstrated for example in a test in which the inhibition of the binding of vitronectin to the cells which contain the vitronectin receptor is determined. Further information about this test is given below. As antagonists of the vitronectin receptor, the compounds of formula (I) and their physiologically acceptable salts are in general suitable for the treatment or prevention of diseases linked to the interactions between the vitronectin receptors and their ligands, in the cell-cell or cell-matrix interaction processes or which can be influenced by the inhibition of interactions of this type, to relieve or cure when inhibition of interactions of this type is desired. As explained at the beginning, such an interaction plays an important role in bone resorption, in angiogenesis or in proliferation of the vascular smooth muscle cells.

Bone diseases the treatment or prevention of which require the use of the compounds of formula (I) are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments with glucocorticoids, therapies linked to taking steroids or corticosteroids or male or female sex hormone deficiencies.

All these disorders are characterized by bone loss, which is caused by a lack of equilibrium between bone formation and bone destruction and which can be favourably influenced by the inhibition of bone resorption by the osteoclasts. Besides this use as an inhibitor of bone resorption mediated via the osteoclasts, the compounds of formula (I) and their physiologically acceptable salts are used as inhibitors of tumorous growth or of cancerous metastases, in the treatment of inflammatory disorders, for the treatment or prevention of cardiovascular disorders, such as arteriosclerosis or restenosis, or the treatment or prevention of nephropathy or retinopathy such as for example diabetic retinopathy.

The compounds according to the invention can also have an activity with respect to other integrins which interact with their ligands via the tripeptide sequence RGD ($\alpha_v\beta_1$, $\alpha_v\beta_5$, $\alpha_{IIb}\beta_3$), giving them pharmacological properties which can be used to treat pathologies associated with these receptors.

This activity vis-à-vis the integrins therefore makes the compounds of formula (I) of use in the prevention or treatment of numerous diseases such as those mentioned above or in the publication by Dermot Cox DN§P 8(4) May 1995, 197-205 the content of which is incorporated in the present Application by way of reference.

Therefore a more particular subject of the present invention is a compound of formula (I) and/or its physiologically acceptable salts as defined above as a medicament having an antagonist activity on the vitronectin receptor.

Therefore a more particular subject of the present invention is a compound of formula (I) and/or its physiologically acceptable salts and/or its prodrugs as defined above as a medicament having an inhibitory activity on bone resorption or for the treatment or prevention of osteoporosis.

Therefore a more particular subject of the present invention is a compound of formula (I) and/or its physiologically acceptable salts as defined above as a medicament having an inhibitory activity on tumorous growth or cancerous metastases.

Therefore a more particular subject of the present invention is a compound of formula (I) and/or its physiologically acceptable salts as defined above as a medicament having an anti-inflammatory activity or for the treatment or prevention of cardiovascular disorders, restenosis, arteriosclerosis, nephropathies or retinopathies.

A subject of the present invention is also the use of the compounds of formula (I) and/or their physiologically acceptable salts as defined above for the preparation of medicaments intended for the prevention or treatment of osteoporosis.

A subject of the present invention is also the use of the compounds of formula (I) and/or their physiologically acceptable salts as defined above for the preparation of medicaments intended to inhibit tumorous growth or cancerous metastases.

A subject of the present invention is also the use of the compounds of formula (I) and/or their physiologically acceptable salts as defined above for the preparation of medicaments intended for the prevention or the treatment of cardiovascular disorders, restenosis, arteriosclerosis, nephropathies or retinopathies.

When the compounds of formula (I) are used, the doses can vary within broad limits and must be set according to the person treated. This depends for example on the compound used or the nature and severity of the disease to be treated, whether the conditions are serious or chronic or if a prophylactic treatment is used.

In the case of administration by oral route, the daily dose in general varies from 0.01 to 100 mg/kg and preferably from 0.1 to 50 mg/kg.

In the case of administration by intravenous route, the daily dose varies approximately from 0.01 to 100 mg/kg and preferably from 0.1 to 10 mg/kg.

The daily dose can be divided, in particular in the case of the administration of a large quantity of active ingredient, into several, for example 2, 3 or 4 parts. If appropriate, depending on individual behaviour, it may be necessary to administer different increasing or decreasing doses. Apart from the use of the compounds of formula (I) as medicaments, it is also possible to envisage their use as a vehicle or support for active ingredients in order to deliver these active compounds specifically towards the target (Drug targeting, see Targeted Drug Delivery, R. C. Juliano, Handbook of Experimental Pharmacology, Vol 100, Ed. Born, G. V. R. et al, Springer Verlag). The active ingredients which can be delivered are in particular those used for the treatment or prevention of the diseases mentioned above.

The compounds of formula (I) and their salts can also be used as a diagnostic agent, for example for in vitro methods or as auxiliaries in biochemical studies in which blocking the vitronectin receptor or influencing cell-cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrum (MS), infrared (IR) and/or NMR spectrum. The compounds which were purified by chromatography using an eluent which contains for example acetic or trifluoroacetic acid, and which are then dried or in which, during the last synthesis stage, for example trifluoroacetic acid was used in order to eliminate a tert-butyl protective group, sometimes contain, depending on the manner in which the product was dried, the acid originating from the eluent or the last synthesis stage and are therefore found partially or completely in the form of the salt of the acid used, for example in the form of an acetic or trifluoroacetic acid salt. They can also be more or less hydrated.

Abbreviations/Chemical Names Optionally Used:

AcOEt: ethyl acetate; EDCI: 1-(3-dimethylaminopropyl)-3-ethyl-carbodiimide hydrochloride; DMF: dimethylformamide; DIPEA: Diisopropylethylamine; MeOH: methanol; TEA: triethylamine; TFA: trifluoroacetic acid; THF: tetrahydrofuran; MCPBA: meta-chloroperoxybenzoic acid; DBU: 1,8-diazabicyclo[5.4.0]undec-7-ene; PTSA: paratoluenesulphonic acid; DPPA: diphenylphosphorylazide; DMSO: dimethylsulphoxide; Pd/C Palladium on carbon; Boc: terbutoxycarbonyl; CBz: benzyloxycarbonyl; DCC 1,3-dicyclohexylcarbodiimide; BrTMS: bromotrimethylsilane; TMSI: trimethylsilane iodide.

IR: Infrared; NMR: Nuclear Magnetic Resonance; MS: Mass Spectrum; PES: Positive mode electrospray; sh.: shoulder; S: strong; s: singlet; d: doublet; t: triplet; quad: quadruplet; quint: quintuplet; b: broad; m: multiplet; J: coupling constant; Rf: retention factor (chromatography).

Example 1

Synthesis of (6-bromo-5-ethyl-pyrimidin-4-yl)-[3-(5,6,7,8-tetrahydro-[1,8]-naphthyridin-2-yl)-propyl]-amine A mixture of 0.20 g (1 mmole) of 3-(5,6,7,8-tetrahydro-[1,8]-naphthyridin-2-ylpropylamine [prepared according to J. Org. Chem. 2004, 69, (1959-1966)] and 0.30 g (1.1 mmoles) of 4,6-dibromo-5-ethyl-pyrimidine in 20 ml of dimethylacetamide and 1 ml of diisopropylethylamine is taken to 120° C. for 6 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent evaporated off under reduced pressure (2 kPa). The residue is chromatographed on silica gel eluting with a gradient of 100% heptane to 100% ethyl acetate. 0.21 g of expected product is obtained in the form of a yellow oil.

TLC: Rf=0.25 (silica gel, eluent: ethyl acetate)

1H-NMR (CDCl3): δ 1.13 (t, 3H, $CH_2$—$CH_3$); 1.93 and 2.03 (2m, 2×2H, $CH_2$—$CH_2$—$CH_2$); 2.57 (q, 2H, $CH_2$—$CH_3$); 2.71 (m, 4H, $CH_2$—$CH_2$—$CH_2$—NH); 3.44 and 3.55 (2m, 2×2H, $CH_2$—$CH_2$—$CH_2$—NH); 6.39 and 7.11 (2d, 2H, H naphthyridine); 8.17 ppm (s, N=CH—N); 5.01 and 5.67 (2m, 2×1H, mobile H's).

MS: 378.379 (MH+).

Synthesis of tert-butyl 2-benzyloxycarbonylamino-3-[5-ethyl-6-[3-(5,6,7,8-tetrahydro-[1,8]-naphthyridin-2-yl)propylamino]-pyrimidin-4-ylamino]-propionate A mixture of 105 mg (0.28 mmole) of (6-bromo-5-ethyl-pyrimidin-4-yl)-[3-(5,6,7,8-tetrahydro-[1,8]-naphthyridin-2-yl)-propyl]-amine, 150 mg (0.5 mmole) of tert-butyl 3-amino-2-benzyloxycarbonylamino propionate) (prepared according to J. Med. Chem. (2001), 44 (8), 1158-1176), 140 mg (0.92 mmole) of cesium fluoride, 40 mg (0.044 mmole) of tris(dibenzylideneacetone) dipalladium (0), and 60 mg (0.097 mmole) of 2,2'-bis(diphenyl-phosphino)-1,1'-binaphthyl in 20 ml of dioxane is heated under reflux for 4 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent evaporated off under reduced pressure (2 kPa). The residue is chromatographed on alumina eluting with a gradient of heptane-ethyl acetate 100-0 to 0-100. 70 mg of expected product is obtained in the form of yellow oil.

TLC: Rf=0.66 (silica gel, eluent: dichloromethane-methanol-water-acetic acid 85-15-2-2)

1H-NMR (CDCl$_3$): δ 1.11 (t, 3H, $CH_2$—$CH_3$); 1.47 (s, 9H, tBu); 1.96 and 2.16 (2m, 2×2H, $CH_2$—$CH_2$—$CH_2$); 2.41 (q, 2H, $CH_2$—$CH_3$); 2.77 and 2.84 (2t, 2×2H, $CH_2$—$CH_2$—$CH_2$—NH); 3.44 and 3.52 (2m, 2×2H, $CH_2$—$CH_2$—$CH_2$—NH); 3.86 (m, 2H, NH—$CH_2$—CH—NH); 4.39 (m, 1H, NH—$CH_2$—CH—NH); 5.16 (s, 2H, $CH_2$-Ph); 6.43 and 7.35 (masked) (2d, 2H, H naphthyridine); 7.35 (m, 5H, Ph) 8.15 ppm (s, N=CH—N)

MS: 590 (MH+); 534 (MH-tBu+); 400 (MH-COOCH2Ph+).

Synthesis of 2-benzyloxycarbonylamino-3-[5-ethyl-6-[3-(5,6,7,8-tetrahydro-[1,8]-naphthyridin-2-yl)propylamino]-pyrimidin-4-ylamino]-propionic acid bis(trifluoroacetate)

65 mg (0.11 mmole) of tert-butyl 2-benzyloxycarbonylamino-3-[5-ethyl-6-[3-(5,6,7,8-tetrahydro-[1,8]-naphthyridin-2-yl)propylamino]-pyrimidin-4-ylamino]-propionate in 5 ml of dichloromethane with 0.5 ml of trifluoroacetic acid is stirred at ambient temperature for 16 hours. Toluene is added and the reaction mixture is evaporated to dryness under reduced pressure (2 kPa). The residue is solubilized in the minimum amount of dichloromethane with a little methanol then poured into diisopropyl ether. The precipitate is filtered. 45 mg of expected product is obtained in the form of a beige solid.

TLC: Rf=0.55 (silica gel, eluent: dichloromethane-methanol-water-acetic acid 85-15-2-2)

HPLC/MS: 534 (MH+); 400 (MH-COOCH2Ph+); 532-(M-H−); 424-(532-OCH2Ph−); 1065-(2M-H−)

Example 2

Synthesis of (6-chloro-5-methyl-pyrimidin-4-yl)-[3-(5,6,7,8-tetrahydro-[1,8]-naphthyridin-2-yl)-propyl]-amine A mixture of 774.3 mg (4.05 mmoles) of 3-(5,6,7,8-tetrahydro-[1,8]-naphthyridin-2-ylpropylamine (prepared according to J. Org. Chem. 2004, 69, 1959-1966) and 600 mg (3.68 mmoles) of 4,6-dichloro-5-methyl-pyrimidine in 6 ml of dimethylacetamide and 1.2 ml of diisopropylethylamine is taken to 120° C. for 9 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent evaporated off under reduced pressure (2 kPa). The residue is chromatographed on Alumina then on silica eluting with a gradient of 100% heptane to 100% ethyl acetate. 680 mg (Yield=58%) of expected product is obtained.

TLC: Rf=0.096 (silica gel, eluent: 100% ethyl acetate)

1H-NMR (CDCl$_3$-d6): δ 1.96 and 2.1 (2m, 2*2H, $CH_2$—$CH_2$—$CH_2$); 2.12 (s, 3H, $CH_3$); 2.75 (m, 2*2H, $CH_2$—$CH_2$—$CH_2$—NH); 3.46 and 3.6 (2m, 2*2H, $CH_2$—

CH$_2$—CH$_2$—NH); 4.92 and 5.45 (2m, 2*1H, NH); 6.42 and 7.13 (2d, 2*1H, naphthyridine); 8.3 (s, 1H, N=CH—N).

MS: 318 (MH+).

Synthesis of tert-butyl 2-benzyloxycarbonylamino-3-[5-methyl-6-[3-(5,6,7,8-tetrahydro-[1,8]-naphthyridin-2-yl)propylamino]-pyrimidin-4-ylamino]-propionate A mixture of 680 mg (2.14 mmole) of (6-Chloro-5-methyl-pyrimidin-4-yl)-[3-(5,6,7,8-tetrahydro-[1,8]-naphthyridin-2-yl)-propyl]-amine, 755 mg (2.57 mmole) of tert-butyl 3-amino-2-benzyloxycarbonylamino propionate (prepared according to J. Med. Chem. (2001), 44 (8), 1158-1176), 455 mg (3 mmole) of cesium fluoride, 133 mg (0.214 mmole) of tris(dibenzylideneacetone) dipalladium (0), and 98 mg (0.107 mmole) of 2,2'-bis(diphenyl-phosphino)-1,1'-binaphthyl in 20 ml of dimethoxyetane was heated under reflux for 24 hours The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent evaporated off under reduced pressure (2 kPa). The residue is chromatographed twice on alumina eluting with a gradient of ethyl acetate-isopropyl ether (50/50) with 10% of a dichloromethane-methanol mixture (9/1). 220 mg of expected product is obtained.

TLC: Rf=0.30 (silica gel, eluent: dichloromethane-methanol-water-acetic acid 90-10-1-1)

1H-NMR (CDCl$_3$): δ 1.45 (s, 9H, tBu); 1.76 to 2.1 (2m, 7H, CH2-CH2-CH2, CH2-CH2-CH2, CH3); 2.63 to 2.8 (m, 2*2H, CH2-CH2-CH2-NH); 3.4 to 3.6 (m, 2*2H, CH2-CH2-CH2-NH); 3.7 to 4.05 (2m, 2H, NH—CH2-CH—NH); 4.47 (m, 1H, NH—CH2-CH—NH); 4.73 and 4.8 (2m, 2H, NH); 5.03 (s, 2H, CH2-O-Ph); 6.42 and 7.35 (2d, 2H, naphthyridine); 6.55, 6.8 and 6.95 (3m, 3*1H, NH); 7.02 to 7.35 (m, 5H, Ph); 8.18 (s, 1H, N=CH—N).

MS: 576 (MH+); 520 (MH-tbu+); 386 (MH-tbu-COOCH2Ph+).

Synthesis of 2-benzyloxycarbonylamino-3-[5-methyl-6-[3-(5,6,7,8-tetrahydro-[1,8]-naphthyridin-2-yl)propylamino]-pyrimidin-4-ylamino]-propionic acid, bis(trifluoroacetate)

40 mg (0.069 mmole) of tert-butyl 2-benzyloxycarbonylamino-3-[5-methyl-6-[3-(5,6,7,8-tetrahydro-[1,8]-naphthyridin-2-yl)propylamino]-pyrimidin-4-ylamino]-propionate in 1 ml of dichloromethane with 0.2 ml of trifluoroacetic acid is stirred at ambient temperature for 16 hours. Toluene is added and the reaction mixture is evaporated to dryness under reduced pressure (2 kPa). The residue is solubilized in the minimum amount of dichloromethane then poured into diisopropyl ether. The precipitate is filtered. 43 mg of expected product is obtained in the form of an off-white solid.

TLC: Rf=0.13 (silica gel, eluent: dichloromethane-methanol-water-acetic acid 90-10-1-1)

NMR (CDCl$_3$): δ 1.92 and 2.0 (2m, 2*2H, CH$_2$—CH$_2$—CH$_2$); 2.05 (s, 3H, CH$_3$); 2.7 and 2.84 (m, 2*2H, CH$_2$—CH$_2$—NH); 3.42 and 3.52 (2m, 2*2H, CH$_2$—CH$_2$—NH); 3.85 (m, 2H, NH—CH$_2$—CH—NH); 4.4 (m, 1H, NH—CH$_2$—CH—NH); 4.73 and 4.8 (2m, 2H, NH); 5.12 (s, 2H, CH$_2$—O-Ph); 5.47 (m, 1H, NH); 6.37 and 7.12 (2d, 2H, naphthyridine); 7.35 (m, 5H, Ph); 8.17 (s, N=CH—N).

HPLC/MS: 520 (MH+); 386 (MH-COOCH2Ph+).

Example 3

Preparation of 3-[1,8]naphthyridin-2-yl-propan-1-ol

914 μl (9 mmoles) of 5-hydroxy-pentan-2-one, 750 μl (9 mmoles) of pyrrolidine and 11.5 μl (0.2 mmole) of concentrated sulphuric acid are added at ambient temperature into a flask containing 1 g (8.19 mmoles) of 2-amino-pyridine-3-carbaldehyde solubilized in 5 ml of ethanol. The reaction mixture is then taken to reflux (78° C.) for 3 hours and 30 minutes.

After cooling down, the solution is concentrated to dryness under reduced pressure (2 kPa) and the residue obtained is taken up in a mixture of water, ethyl acetate and a saturated solution of sodium bicarbonate. The organic phase is separated and the aqueous phase extracted with ethyl acetate then with n-butanol. The collected organic phases are dried over magnesium sulphate. The filtrate is concentrated to dryness then chromatographed on silica gel eluting with a gradient of ethyl acetate (100%), ethyl acetate-methanol (98-2) to ethyl acetate-methanol (90-10).

990 mg of expected product is obtained.

TLC: Rf=0.1 [silica gel, eluent: ethyl acetate-methanol (98-2)

1H-NMR (CDCl$_3$-d1): δ 2.2 (quintuplet, 2H, O—CH2-CH2-CH2); 2.97 (m, 1H, HO—CH2-CH2-CH2); 3.22 (t, 2H, O—CH2-CH2-CH2); 3.8 (t, 2H, O—CH2-CH2-CH2); [(7.33; 7.47; 8.12; 8.18; 9.08), 5 multiplets, 5H, Naphthyridine].

MS: 189 (MH+)

Synthesis of 2-[3-(6-chloro-5-methyl-pyrimidin-4-yloxy)-propyl]-[1,8]naphthyridine 800 mg (4.24 mmoles) of 3-[1,8]naphthyridin-2-yl-propan-1-ol solubilized in 5 ml of dioxane is added dropwise, at ambient temperature and under nitrogen, into a single-necked flask containing 102 mg (2.12 mmoles) of sodium hydride and 7 ml of dioxane.

This mixture is maintained under stirring and under an inert atmosphere at ambient temperature for 2 hours.

Then 346.4 mg (2.12 mmoles) of 4,6-dichloro-5-methyl-pyrimidine solubilized in 5 ml of dioxane is added.

The mixture is then heated under reflux for 5 hours and 30 minutes then concentrated to dryness under vacuum. The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate. The filtrate is concentrated to dryness then chromatographed on silica gel eluting with a gradient of ethyl acetate (100%) then ethyl acetate-methanol (98-2).

300 mg of expected product is obtained.

TLC: Rf=0.32 (silica gel, eluent: ethyl acetate-methanol (95-5).

1H-NMR (CDCl$_3$): δ 2.1 (singlet, 3H, —CH3); 2.5 (quintuplet, 2H, O—CH2-CH2-CH2); 3.25 (triplet, 2H, O—CH2-CH2-CH2); 4.55 (t, 2H, O—CH2-CH2-CH2); [(7.43; 7.5; 8.15; 8.2; 9.13), 5 multiplets, 5H, naphthyridine]; 8.32 (singlet, 1H, N=CH—N).

Synthesis of 7-[3-(6-chloro-5-methyl-pyrimidin-4-yloxy)-propyl]-1,2,3,4-tetrahydro-[1,8]naphthyridine A sufficient quantity of ethanol to solubilize the product, and 15 mg of platinum oxide are added to 300 mg (0.953 mmoles) of 2-[3-(6-chloro-5-methyl-pyrimidin-4-yloxy)-propyl]-[1,8]naphthyridine. The reaction mixture is then purged under vacuum and surmounted on a balloon flask containing hydrogen. The reaction medium is left under stirring and at ambient temperature for 6 hours then overnight. The reaction mixture is then filtered on Clarcel and concentrated to dryness under reduced pressure (2 kPa). Then 300 mg of expected product is obtained.

TLC: Rf=0.6 [silica gel, eluent: ethyl acetate-methanol (95-5)].

1H-NMR (CDCl$_3$): δ 1.93 (quintuplet, 2H, CH2-CH2-CH2-NH), 2.22 (multiplet, 5H, —CH3, O—CH2-$\overline{CH2}$-CH2); 2.73 (m, 4H, O—$\overline{CH2}$-CH2-CH2, $\overline{CH2}$-CH2-CH2-NH); 3.43 (m, 2H, CH2-CH2-CH2-$\overline{NH}$); $\overline{4.45}$ (triplet, 2H, O—CH2-CH2-CH2); 5.23 $\overline{(m}$, 1H, CH2-CH2-CH2-NH); 6.37 $\overline{and}$ 7.1 (2d, 2H, naphthyridine]; 8.4 (singlet, 1$\overline{H, N}$=CH—N).

MS: 319 (MH+)

Synthesis of tert-butyl 2-benzyloxycarbonylamino-3-{5-methyl-6-[3-(5,6,7,8-tetrahydro-[1,8]naphthyridin-2-yl)-propoxy]-pyrimidin-4-ylamino}-propionate A mixture of 2 g (6.27 mmoles) of 7-[3-(6-chloro-5-methyl-pyrimidin-4-yloxy)-propyl]-1,2,3,4-tetrahydro-[1,8]naphthyridine and 2.2 g (7.52 mmoles) of tert-butyl 3-amino-2-benzyloxycarbonylamino propionate, in the presence of 1.3 g (8.78 mmoles) of cesium fluoride, 390 mg (62.7 μmoles) of (2,2'-bis(diphenylphosphino)-1,1'-binaphthyl and 290 mg (31.3 μmoles) of tris-dibenzylideneacetone dipalladium (o) in 35 ml of 1,2-dimethoxyethane is heated under reflux for 24 hours.

After cooling down the solution is concentrated to dryness then taken up in a mixture of water, ethyl acetate and a saturated solution of sodium bicarbonate. The organic phase is decanted and the aqueous phase is extracted with ethyl acetate. The collected organic phases are dried over magnesium sulphate and evaporated to dryness under vacuum. The residue is chromatographed on silica with a gradient of ethyl acetate-dichloromethane (50-50) to ethyl acetate-dichloromethane (80-20). 772 mg of expected product is obtained.

TLC: Rf=0.17 (silica gel, eluent: ethyl acetate-dichloromethane 80-20).

1H-NMR (CDCl$_3$): δ 1.45 (s, 9H, tBu); 2.88 (s, 3H, —CH3); 1.93 (m, 2H, NH—CH2-CH2-CH2); 2.17 (m, 2H, O—CH2-CH2-CH2); 2.68 and 2.8 $\overline{(m, 4H}$, NH—CH2-CH2-CH2, O—$\overline{CH2}$-CH2-CH2); 3.45 (m, 2H, NH—$\overline{CH2}$-CH2-CH2); 3.9 (m, $\overline{2H}$, NH—CH2-CH—NH); 4.35 (t, $\overline{2H,}$ O—CH2-CH2-CH2); 4.45 $\overline{(m,}$ 1H, NH—CH2-CH—NH); $\overline{5.12}$ (m, 2H, O—CH2-Ph); 4.95 and 6.10 (2m, $\overline{2H}$, NH); 6.37 and 7.13 (2d, $\overline{2H, CH}$=CH naphthyridine); 7.35 (m, 5H, Ph); 8.2 (s, 1H, N=$\overline{CH—N)}.$

MS: 577 (MH+)

Example 4

Synthesis of 2-benzyloxycarbonylamino-3-{5-methyl-6-[3-(5,6,7,8-tetrahydro-[1,8]naphthyridin-2-yl)-propoxy]-pyrimidin-4-ylamino}-propionic acid, bis(trifluoroacetate)

Formation of the acid corresponding to the ester of Example 3: A mixture of 65 mg (0.11 mmoles) of tert-butyl 2-benzyloxycarbonylamino-3-{5-methyl-6-[3-(5,6,7,8-tetrahydro-[1,8]naphthyridin-2-yl)-propoxy]-pyrimidin-4-ylamino}-propionate solubilized in 1 ml of dichloromethane and 50 μl of trifluoroacetic acid is stirred at ambient temperature for 25 hours. Then toluene is added and the mixture is evaporated to dryness. The residue is solubilized in a minimum amount of dichloromethane then poured into a mixture of pentane and diisopropyl ether. The precipitate is filtered. An impure yellow powder is obtained which must be purified on silica with a gradient of 100% ethyl acetate to ethyl acetate-methanol (80-20).

21 mg of expected product is obtained.

TLC: Rf=0.33 [silica gel, eluent: Dichloromethane-methanol-acetic acid-water (90-10-1-1).

1H-NMR (CDCl$_3$): δ 1.72 and 1.95 (m, 5H, —CH3, NH—CH2-CH2-CH2); 2.15 (m, 2H, O—CH2-CH2-CH2); 2.63 and 2.85 $\overline{(m,}$ 4H, NH—CH2-CH2-CH2, O—$\overline{CH2}$-CH2-CH2); 3.45 (m, 2H, NH—CH2-CH2-$\overline{CH2)}$; 3.7 and 4.0 (m, $\overline{2H, NH}$—CH2CH—NH); $\overline{4.3}$ (m, 3H, O—CH2-CH2-CH2, NH—CH$\overline{2-CH}$—NH); 5.1 (m, 2H, O—CH$\overline{2-Ph}$); 5.78 and 6.10 (2m, 2$\overline{H, NH}$); 6.33 and 7.25 (2d, $\overline{2H, CH}$=CH naphthyridine); 7.28 and 7.45 (m, 5H, Ph); 8.$\overline{13}$ (s, $\overline{1H}$, N=CH—N).

$\overline{MS}$: 521 (MH+)

Example 5

1) Synthesis of N-t.butoxycarbonyl-3-(methoxy-methyl-carbamoyl)-azetidine 2 g (10 mmol) of N-t.butoxycarbonyl-azetidine-3-carboxylic acid is dissolved in 20 ml of dimethylformamide under argon.

This solution is cooled down to 0° C. using an ice bath and 5.46 g (12.3 mmol) of benzotriazol-1-yloxytris(dimethylamino)phosphonium hexafluorophosphate, 1.4 g (14.3 mmol) of N,O-dimethylhydroxylamine chloride and 6 ml of diisopropylethylamine are added. The reaction mixture is left to return to ambient temperature and is stirred for 18 hours at ambient temperature.

The dimethylformamide and diisopropylethylamine are evaporated off under reduced pressure (2 kPa).

Purification is carried out by chromatography on silica gel eluting with a heptane/ethyl acetate 50:50 mixture 2.1 g of colourless oil is recovered.

TLC: Rf=0.25 (silica gel, eluent: heptane/ethyl acetate 50:50

1H-NMR (CDCl$_3$): δ 1.44 (s, 9H, tBu); 3.22 (s, 3H, —N—CH2); 3.64 (m, 1H, H3); 3.67 (s, 3H, —O—CH3); 4.05 and $\overline{4.15}$ (m, 4H, H2 and H2')

2) Synthesis of N-t.butoxycarbonyl-3-acetyl-azetidine 110 mg (0.45 mmol) of N-t.butoxycarbonyl-3-(methoxy-methyl-carbamoyl)-azetidine is solubilized in 2 ml of ether under argon.

This solution is cooled down to 0° C. using an ice bath and 1 ml of a 1.6 M solution of methyllythium in ether is added dropwise.

The reaction medium is stirred for 2 hours at this temperature then treated with a 1 M aqueous solution of hydrochloric acid.

The aqueous and ether phases are decanted and separated. This operation is repeated 3 times then the ethereal phases are collected and dried over MgSO4, then after filtration the ether is evaporated under reduced pressure.

40 mg of a colourless oil is recovered.

TLC: Rf=0.35 (silica gel, eluent: heptane/ethyl acetate 50:50

1H-NMR (CDCl$_3$): δ 1.44 (s, 9H, tBu); 2.2 (s, 3H, —CO—CH3); 3.45 (m, 1H, H3); 3.67 (s, 3H, —O—CH3); 4.07 (m, 4H, H2 and H2')

N-t.butoxycarbonyl-3-[1,8]naphthyridin-2-yl-azetidine 30 mg of N-t.butoxycarbonyl-3-acetyl-azetidine (0.150 mmol) is solubilized in 2 ml of ethanol to which 18 mg (0.150 mmol) of 2-aminopyridine-3-carboxyaldehyde and 25 mg of potassium carbonate (0.18 mmol) are added.

This mixture is taken to reflux for 24 hours then is left to return to ambient temperature and the ethanol is evaporated off under reduced pressure (2 kPa).

The residue obtained is purified by chromatography on silica gel eluting with a dichloromethane/MeOH 95:5 mixture.

30 mg of expected product is recovered in the form of a beige solid.

TLC: Rf=0.25 (silica gel, eluent: CH2Cl2/MeOH 95:5)
MS: 256 (MH+); 230 (MH-tBu+)
1H-NMR (CDCl$_3$): δ 1.47 (s, 9H, tBu); 4.18 (m, 1H, H3); 4.40 (m, 4H, H2 and H2'); 7.52 (m, 2H, H7 and H4); 8.22 (m, 2H, H5 and H6); 9.14 (m, 1H, H8)

3-[1,8]Naphthyridin-2-yl-azetidine 50 mg (0.175 mmol) of N-t.butoxycarbonyl-3-[1,8]Naphthyridin-2-yl-azetidine is solubilized in 2 ml of CH$_2$Cl$_2$ to which 0.2 ml of trifluoroacetic acid is added and the reaction medium is left under stirring for 18 hours at ambient temperature.

The trifluoroacetic acid and dichloromethane are evaporated off under reduced pressure (2 kPa).

40 mg of crude product is isolated in the form of a yellow oil.

TLC: Rf=0.25 (silica gel, eluent: CH$_2$Cl$_2$/MeOH 90:10)
MS: 186 (MH+)

Synthesis of 7-azetidin-3-yl-1,2,3,4-tetrahydro-[1,8]naphthyridine 40 mg of 3-[1,8]naphthyridin-2-yl-azetidine is solubilized in 2 ml of ethanol to which 10 mg of platinum oxide is added. The reaction medium is stirred under a hydrogen atmosphere for one hour.

The catalyst is filtered out and the ethanol is evaporated off under reduced pressure.

The crude residue is purified by filtration on silica gel eluting with a dichloromethane/MeOH mixture 95:5 and 85:15

25 mg (61%) of a colourless oil is recovered.
TLC: Rf=0.1 (silica gel, eluent: CH2Cl2/MeOH 90:10)
1H-NMR (MeOD): δ 1.90 (m, 2H, H7); 2.75 (m, 2H, H6); 3.41 (m, 2H, H8); 3.96 (m, 1H, H3); 4.30 (m, 4H, H2 and H2'); 6.40 (d, 1H, H4) and 7.15 (d, 1H, H5)
MS: 190 (MH+)

Synthesis of 2,5-dimethyl-4,6-dihydroxy-pyrimidine

A single-necked flask containing 40 ml of methanol, placed under a nitrogen atmosphere, is cooled down to 0° C. using an ice bath, 9.72 g of sodium methylate (i.e. a solution concentration c=3 mol.l$^{-1}$) is added to the reaction mixture then 5 g (53 mmoles) of acetamidine hydrochloride is added at 0° C. and in small quantities. Stirring is maintained at ambient temperature for about twenty minutes, then 8.3 ml of diethyl methylmalonate is added dropwise. Stirring is maintained for 3 hours. Then the methanol is condensed under reduced pressure (2 kPa). The crude product obtained is taken up with a minimum quantity of water, cooled down to 0° C. then acidified with pure acetic acid to a pH between 4 and 5. The white precipitate formed is filtered, rinsed with water, ethyl ether and pentane. Then the white product is dried over P$_2$O$_5$ under reduced pressure (0.2 kPa). 3.3 g of expected product is obtained.

TLC: Rf=0.2 (silica gel, eluent: dichloromethane-methanol-water-acetic acid 85-15-2-2)
1H-NMR (DMSO d6): δ 1.68 (s, 3H, OH—CH=C—CH3); 2.18 (s, 3H, N=C—CH3).

Synthesis of 2,5-dimethyl-4,6-dichloro pyrimidine

A mixture of 3.3 g (23.5 mmoles) of 2,5-dimethyl-4,6-dihydroxy-pyrimidine and 15 ml of phosphorus oxychloride is taken to reflux for 8 hours. After returning to ambient temperature, the reaction mixture is poured slowly onto a mixture of ice and water. This aqueous phase is extracted with ethyl acetate. The organic phase is washed with a saturated solution of sodium bicarbonate then dried over magnesium sulphate and evaporated to dryness under reduced pressure (2 kPa). 3.39 g of expected product is obtained.

TLC: Rf=0.9 (silica gel, eluent: 100% ethyl acetate)
1H-NMR (CDCl3): δ 2.46 (s, 3H, Cl—CH=C—CH3); 2.68 (s, 3H, N=C—CH3)
MS: 177/179 (MH+).

Synthesis of 7-[1-(6-Chloro-2,5-dimethyl-pyrimidin-4-yl)-azetidin-3-yl]-1,2,3,4-tetrahydro-[1,8]naphthyridine 90 mg (0.47 mmol) of 7-azetidin-3-yl-1,2,3,4-tetrahydro-[1,8]naphthyridine is dissolved in 2 ml of dimethylacetamide to which 90 mg (0.51 mmol) of 2,5-dimethyl-4,6-dichloro pyrimidine is added.

This mixture is heated at 100° C. for 18 hours.

The solvent is evaporated off under reduced pressure (2 kPa).

The crude residue is purified by chromatography on silica gel eluting with a dichloromethane/MeOH mixture 95:5

50 mg (32%) of expected product is recovered.
TLC: Rf=0.25 (silica gel, eluent: CH2Cl2/MeOH 95:5)
MS: 330 (MH+).

Tert-butyl 2-benzyloxycarbonylamino-3-{2,5-dimethyl-6-[3-(5,6,7,8-tetrahydro-[1,8]naphthyridin-2-yl)-azetidin-1-yl]-pyrimidin-4-ylamino}-propionate 50 mg (0.150 mmol) of 7-[1-(6-chloro-2,5-dimethyl-pyrimidin-4-yl)-azetidin-3-yl]-1,2,3,4-tetrahydro-[1,8]naphthyridine, 53 mg of tert-butyl 3-amino-2-benzyloxycarbonylamino propionate and 70 mg (0.460 mmol) of cesium fluoride are solubilized in 2 ml of dioxane.

This mixture is heated for 5 minutes at 90° C. then 6 mg (0.01 mmol) of rac-2,2'-bis(diphenylphosphino)-1,1'-Binaphthyl and 9 mg (0.01 mmol) of tris(dibenzylideneacetone) dipalladium are added to it. This mixture is heated at 110° C. for 2 hours under magnetic stirring. The same quantities of catalyst and cesium fluoride are added again and the reaction medium is heated for 2 hours at 140° C. The dioxane is evaporated off under reduced pressure (2 kPa).

The residue obtained is purified by chromatography on silica gel eluting with a heptane/ethyl acetate mixture 1:1.

25 mg of expected product is recovered in the form of a yellow solid
TLC: Rf=0.25 (silica gel, eluent: CH2Cl2/MeOH 95:5)

MS: 588 (MH+); 398 (MH-(tBu and —CO—O—CH2-Ph)+.

2-benzyloxycarbonylamino-3-{2,5-dimethyl-6-[3-(5,6,7,8-tetrahydro-[1,8]-naphthyridin-2-yl)-azetidin-1-yl]-pyrimidin-4-ylamino}-propionic acid bis(trifluoroacetate)

20 mg of tert-butyl 2-benzyloxycarbonylamino-3-{2,5-dimethyl-6-[3-(5,6,7,8-tetrahydro-[1,8]naphthyridin-2-yl)-azetidin-1-yl]-pyrimidin-4-ylamino}-propionate is solubilized in 1 ml of $CH_2Cl_2$ and 0.1 ml of trifluoroacetic acid is added to it.

This solution is stirred for 24 hours at ambient temperature and diluted with toluene.

The solvents and trifluoroacetic acid are evaporated off under reduced pressure (2 kPa). The residue obtained is taken up in a minimum quantity of $CH_2Cl_2$ then this solution is poured into isopropyl ether.

The insoluble part is thus isolated and 15 mg of expected product is recovered in the form of a white powder TLC: Rf=0.1 (silica gel, eluent: CH2Cl2/MeOH 90:10)

1H-NMR (MeOD): δ from 1.95 to 2.00 (m, 5H, H1 and H11); 2.50 (s, 3H, H3); 3.35 (dd, 2H, H10); 3.52 (dd, 2H, H12); 3.30 (m, 1H, H7); 3.97 and 4.15 (2m, 2H, H4); 4.53 (m, 3H, H5+H2 or H2'); 4.80 (dd partially masked by H2O, 2H, H2 or H2'); 5.10 (m, 2H, —O—CH2-C6H5); 6.82 (d, 1H, H8); from 7.30 to 7.40 (m, 5H, —O—CH2-C6H5); 7.62 (d, 1H, H9)

MS: 532 (MH+); 398 (MH-(CO—O—CH2-C6H5)+)

Example 6

Synthesis of tert-butyl 2-benzyloxycarbonylamino-3-[6-(6-amino-3',4',5',6'-tetrahydro-2'H-[2.4]bipyridinyl-1'-yl)-5-methyl-pyrimidin-4-ylamino]-propionate

1) Synthesis of N-t.butoxycarbonyl-4-hydroxy-piperidine 1 g (5 mmol) of N-t.butoxycarbonyl-4-oxo-1-piperidine (marketed by Aldrich) is dissolved in 5 ml of ethanol. This solution is cooled down to 0° C. using an ice bath and 200 mg (7.56 mmol) of tetrasodium borohydride is added by portions and the reaction medium is stirred for 4 hours at ambient temperature. A saturated aqueous solution of ammonium chloride is added to the reaction mixture. The ethanol is evaporated off under reduced pressure (2 kPa) then the reaction mixture is taken up in ethyl acetate. The organic phase is separated from the aqueous phase. This extraction is repeated once and then the organic phases are collected and dried over magnesium sulphate, followed by concentrating under reduced pressure (2 kPa) and in this way 1.05 g of a colourless oil is recovered.

TLC: Rf=0.5 (silica gel, eluent: CH2Cl2/MeOH 90:10)

1H-NMR (CDCl$_3$): δ 1.47 (s, 9H, tBu) and (m, 2H; —CHH—CH2-N—CH2-CHH—); 1.87 (m, 2H, —CHH—CH2-N—CH2-CHH—); 3.04 (m, 2H, —CHH—N—CHH—); 3.85 (m, 2H, —CHH—N—CHH—) and (m, 1H, —CH—OH)

2) Synthesis of N-t.butoxycarbonyl-4-iodo-1-piperidine 2.15 g of triphenylphosphine (8.2 mmole) and 2.08 g of iodine (8.2 mmole) are dissolved in 30 ml of acetonitrile.

The reaction medium is left under stirring for 10 minutes at ambient temperature then 918 mg of imidazole (13.5 mmol) is added and stirring is maintained for another 10 minutes at ambient temperature. Then 1 g (5 mmol) of N-t.butoxycarbonyl-4-hydroxy-1-piperidine is added and stirring is maintained for 24 hours at ambient temperature. The reaction is treated by adding an aqueous solution of sodium thiosulphate and the acetonitrile is evaporated off under reduced pressure (2 kPa), followed by taking up in ethyl acetate, extracting and washing with an aqueous solution of sodium thiosulphate. The organic phases are dried over MgSO4, filtered and the ethyl acetate is evaporated off under reduced pressure (2 kPa), followed by chromatography on silica gel eluting with dichloromethane then dichloromethane/methanol 90:10.

1.1 g (Yield=70%) of colourless oil is recovered.

TLC: Rf=0.8 (silica gel, eluent: CH2Cl2/MeOH 90:10

1H-NMR (CDCl$_3$): δ 1.47 (s, 9H, tBu); 2.03 (m, 4H, —CH2-CHI—CH2-); 3.30 and 3.60 (2m, 4H, —CH2-N—CH2-); 4.46 (m, 1H-CHI—)

3) Synthesis of 2-bromo-6 (2,5-dimethyl-pyrol-1-yl)-pyridine (3)

1 g (5.78 mmol) of 2-amino-6-bromopyridine in 30 ml of toluene is placed in a 100 ml flask surmounted with a Dean Stark apparatus. 0.3 ml of acetic acid and 0.8 ml (6.78 mmol) of acetonylacetone are added, followed by heating under reflux of the toluene for 5 hours. The reaction medium is left to return to ambient temperature and the toluene is evaporated off under reduced pressure (2 kPa). Water is added followed by extraction with ethyl acetate. The organic phases are collected and dried over magnesium sulphate. The ethyl acetate is evaporated off under reduced pressure (2 kPa) and the crude residue is purified by chromatography on silica gel eluting with dichloromethane.

1 g of expected product is recovered in the form of yellow powder.

TLC: Rf=0.7 (silica gel, eluent: CH2Cl2)

1H-NMR (CDCl$_3$): δ 2.20 (s, 6H, —CH3C═CH—CH═CCH3-); 5.90 (s, 2H, —CH3C═CH—CH═CCH3-); 7.08 (d, 1H, H3 or H5); 7.16 (d, 1H, H3 or H5); 7.29 (t, 1H, H4).

4) Synthesis of 6-(2,5-dimethyl-pyrrol-1-yl)-3',4',5',6'-tetrahydro-2'H-[2.4']bipyridinyl-1'-carboxylic acid tert-butyl ester 284 mg (4.34 mmol) of electrolytic zinc is placed in suspension, under an argon atmosphere, then 0.033 ml of 1,2-dibromoethane and 1 ml of tetrahydrofuran are added.

The reaction medium is stirred for 3 minutes at 60° C. and is then left to return to ambient temperature. 0.047 ml of trimethylsilyl chloride is added followed by stirring for 30 minutes at ambient temperature. 1 g (3.2 mmol) of N-t.butoxycarbonyl-4-iodo-1-piperidine solubilized beforehand in 2 ml of tetrahydrofuran is added. This reaction mixture is stirred for 45 minutes at ambient temperature and a solution containing 30 mg (0.032 mmol) of tris(dibenzylideneacetone)dipalladium marketed by Aldrich and 30 mg (0.13 mmol) of tris(2-furyl)phosphine are added to it. Then 1 g (4 mmol) of 2-bromo-6 (2,5-dimethyl-pyrol-1-yl)-pyridine solubilized beforehand in 10 ml of tetrahydrofuran is added. The reaction mixture is left under magnetic stirring at 60° C. for 2 hours, then left to return to ambient temperature, filtered on Clarcel and extracted between ethyl acetate and a saturated aqueous solution of sodium bicarbonate. The aqueous phase is extracted twice with ethyl acetate, then the organic phases are collected and dried over magnesium sulphate. The ethyl acetate is evaporated off under reduced pressure (2 kPa) and the crude residue is purified by chromatography on silica gel eluting with a heptane/ethyl acetate mixture 4:1. 350 mg of expected product is recovered in the form of yellow oil.

TLC: Rf=0.2 (silica gel, eluent: heptane/ethyl acetate 90:10).

1H-NMR (CDCl₃ δ 1.50 (s, 9H, tBu); 1.78 and 1.97 (m, 4H, —CH2-CH2-N—CH2-CH2-); 2.18 (s, 6H, —CH3C=CH—CH=CCH3-); 2.85 and 2.95 (m, 3H, CH—CH2-CHH—N—CHH—CH2-); 4.28 (m, 2H, —CH2-CHH—N—CHH—CH2-); 5.92 (s, 2H, —CH3C=CH—CH=CCH3-); 7.08 (d, 1H, H3 or H5); 7.16 (d, 1H, H3 or H5); 7.29 (t, 1H, H4).

5) Synthesis of 6-(2,5-dimethyl-pyrrol-1-yl)-1',2',3',4',5',6'-hexahydro-[2.4']bipyridinyl 330 mg (0.928 mmol) of 6-(2,5-dimethyl-pyrrol-1-yl)-3',4',5',6'-tetrahydro-2'H-[2.4']bipyridinyl-1'-carboxylic acid tert-butyl ester is placed in solution in 3 ml of dichloromethane to which 0.3 ml of trifluoroacetic acid is added. The reaction medium is stirred for 2 hours at ambient temperature. The dichloromethane is evaporated off under reduced pressure (2 kPa). The residue obtained is taken up in water, followed by rendering basic to pH=10 with concentrated ammonium hydroxide and extracting the product with dichloromethane. The organic phase is dried over magnesium sulphate and the dichloromethane is evaporated off under reduced pressure (2 kPa). 220 mg (Yield=92%) of yellow oil is recovered.

TLC: Rf=0.3 (silica gel, eluent: CH2Cl2/MeOH 90:10)

1H-NMR (CDCl₃): δ 1.90 and 2.08 (m, 4H, —CH2-CH2-N—CH2-CH2-); 2.18 (s, 6H, —CH3C=CH—CH=CCH3-); 2.88 and 3.34 (m, 4H, —CH2-CH2-N—CH2-CH2-); 2.95, (m, 1H, CH—CH2-CH2-N—CH2-); 4.10 (m, 1H, NH); 5.92 (s, 2H, —CH3C=CH—CH=CCH3-); 7.08 (d, 1H, H3 or H5); 7.16 (d, 1H, H3 or H5); 7.29 (t, 1H, H4)

MS: 256 (MH+).

6) Synthesis of 1'-(6-chloro-5-methyl-pyrimidin-4-yl)-6-(2,5-dimethyl-pyrrol-1-yl)-1',2',3',4',5',6'-hexahydro-2.4']bipyridinyl 220 mg (0.860 mmol) of 6-(2,5-dimethyl-pyrrol-1-yl)-1',2',3',4',5',6'-hexahydro-[2.4']bipyridinyl is dissolved in 2 ml of dimethylacetamide to which 140 mg (0.860 mmol) of 4,6-dichloro-5-methyl-pyrimidine marketed by [ ] and 0.2 ml of diisopropylethylamine are added. The mixture is heated at 110° C. under magnetic stirring for one hour. The mixture is left to return to ambient temperature and the dimethylacetamide is evaporated off under reduced pressure (0.2 kPa). The crude residue is taken up in ethyl acetate and washed with water. The aqueous phase is extracted twice with ethyl acetate, the organic phases are collected and dried over magnesium sulphate. The ethyl acetate is evaporated off under reduced pressure (0.2 kPa) and 330 mg of brown resin is recovered which is used for the following stage without purification.

TLC: Rf=0.4 (silica gel, eluent: CH2Cl2)

1H-NMR (CDCl₃): δ 2.02 and 2.10 (m, 4H, —CH2-CH2-N—CH2-CH2-); 2.18 (s, 6H, —CH3C=CH—CH=CCH3-); 2.30 (s, 3H, CH3); 3.08 and 4.01 (m, 4H, —CH2-CH2-N—CH2-CH2-); 3.02, (m, 1H, CH—CH2-CH2-N—CH2-); 5.92 (s, 2H, —CH3C=CH—CH=CCH3-); 7.09 (d, 1H, H3 or H5); 7.20 (d, 1H, H3 or H5); 7.29 (t, 1H, H4); 8.41 (s, 1H, =N—CH=N)

Synthesis of tert-butyl 2-benzyloxycarbonylamino-3-{6-[6-(2,5-dimethyl-pyrrol-1-yl)-3',4',5',6'-tetrahydro-2'H-[2.4']bipyridinyl-1'-yl]-5-methyl-pyrimidin-4-ylamino}-propionate 330 mg (0.866 mmol) of 1'-(6-chloro-5-methyl-pyrimidin-4-yl)-6-(2,5-dimethyl-pyrrol-1-yl)-1',2',3',4',5',6'-hexahydro-[2.4']bipyridinyl is dissolved in 5 ml of dimethoxyethane. 286 mg (1 mmol) of tert-butyl 3-amino-2-benzyloxycarbonylamino propionate, 184 mg (1.21 mmol) of cesium fluoride, 54 mg (10% mol) of 2,2'-bis(diphenylphosphino)-1,1'-binaphthyl and 40 mg (5% mol) of tris(dibenzylideneacetone) dipalladium are added successively. This mixture is heated at 100° C. for 18 hours under magnetic stirring. The reaction medium is left to return to ambient temperature and the dimethoxyethane is evaporated off under reduced pressure (2 kPa). The residue obtained is taken up in ethyl acetate and washed with a saturated aqueous solution of sodium bicarbonate. The aqueous phase is extracted with ethyl acetate, the organic phases are collected and dried over magnesium sulphate. The ethyl acetate is evaporated off under reduced pressure (2 kPa). The residue obtained is purified by chromatography on silica gel eluting with a heptane/ethyl acetate mixture 1:1. 200 mg of yellow solid is recovered.

TLC: Rf=0.2 (silica gel, eluent: heptane/ethyl acetate 1:1)

1H-NMR (CDCl₃): δ 1.50 (s, 9H, tBu); 1.97 (s, 3H, CH3); 2.02 to 2.10 (m, 4H, —CH2-CH2-N—CH2-CH2-); 2.18 (s, 6H, —CH3C=CH—CH=CCH3-); 3.20 and 3.78 (m, 4H, —CH2-CH2-N—CH2-CH2-); 3.00 (m, 1H, CH—CH2-CH2-N—CH2-); from 3.85 to 4.00 (m, 2H, NH—CH2-CHCOOtBuNH); 4.47 (m, 1H, NH—CH2CH—COOtBuNH); 5.12 (2H, —O—CH2-Phenyl); 5.92 (s, 2H, —CH3C=CH—CH=CCH3-); 6.12 (m, mobile 1H); 7.09 (d, 1H, H3 or H5); 7.21 (d, 1H, H3 or H5); 7.78 (t, 1H, H4); 7.45 (m, aromatic 5H); 8.32 (s, 1H, =N—CH=N)

MS: 641 (MH+), 584 (MH-tBu+)

Synthesis of tert-butyl 3-[6-(6-amino-3',4',5',6'-tetrahydro-2'H-[2,4']bipyridinyl-1'-yl)-5-methyl-pyrimidin-4-ylamino]-2-benzyloxycarbonylamino-propionate 100 mg (0.15 mmol) of tert-butyl 2-benzyloxycarbonylamino-3-{6-[6-(2,5-dimethyl-pyrrol-1-yl)-3',4',5',6'-tetrahydro-2'H-[2.4']bipyridinyl-1'-yl]-5-methyl-pyrimidin-4-ylamino}-propionate is dissolved in 3 ml of ethanol and 0.3 ml of water. 50 mg (0.75 mmol) of hydroxylamine hydrochloride is added and the reaction medium is heated for 18 hours at 90° C. The solvents are evaporated off under reduced pressure (2 kPa) and the crude residue is purified by chromatography on silica gel eluting with a CH2Cl2/MeOH mixture 90:10. 30 mg of expected product is obtained in the form of a resin.

TLC: Rf=0.5 (silica gel, eluent: CH₂Cl₂/MeOH 90:10)

1H-NMR (CDCl₃ δ 1.50 (s, 9H, tBu); 1.97 (s, 3H, CH3); 2.02 to 2.10 (m, 4H, —CH2-CH2-N—CH2-CH2-); 2.18 (s, 6H, —CH3C=CH—CH=CCH3-); 3.20 and 3.78 (m, 4H, —CH2-CH2-N—CH2-CH2-); 3.00 (m, 1H, CH—CH2-CH2-N—CH2-); from 3.85 to 4.00 (m, 2H, NH—CH2-CHCOOtBuNH); 4.47 (m, 1H, NH—CH2CH—COOtBuNH); 5.12 (2H, —O—CH2-Phenyl); 5.92 (s, 2H, —CH3C=CH—CH=CCH3-); 6.18, 6.57, 6.62 (3d, H3 and H5+mobile 1H); 7.45 (m, aromatic 5H's); 7.60 (t, 1H, H4); 8.32 (s, 1H, =N—CH=N).

MS: 562 (MH+), 372 (MH-tBu and —CO—O-benzyl+).

Synthesis of tert-butyl 2-benzyloxycarbonylamino-3-[6-(6-ethylamino-3',4',5',6'-tetrahydro-2'H-[2.4']bipyridinyl-1'-yl)-5-methyl-pyrimidin-4-ylamino]-propionate 50 mg (0.09 mmol) of tert-butyl 2-benzyloxycarbonylamino-3-[6-(6-amino-3',4',5',6'-tetrahydro-2'H-[2.4']bipyridinyl-1'-yl)-5-methyl-pyrimidin-4-ylamino]-propionate is solubilized in 2 ml of dichloromethane. The mixture is placed under an argon atmosphere and cooled down to 0° C. using an ice bath.

0.01 ml (0.18 mmol) of acetaldehyde and 30 mg (0.14 mmol) of sodium triacetoxyborohydride is added.

This mixture is stirred for 1 hour at ambient temperature and the same quantities of acetaldehyde and sodium triacetoxyborohydride are added again.

Stirring at ambient temperature is maintained for 2 hours then finally another 30 mg of sodium triacetoxyborohydride is added.

Stirring is maintained at ambient temperature for 15 minutes then the dichloromethane is evaporated off under reduced pressure (2 kPa).

The crude residue is purified by chromatography on silica gel eluting with dichloromethane/methanol 95:5 then 90:10.

40 mg of expected product is recovered.

TLC: Rf=0.7 (silica gel, eluent: $CH_2Cl_2$/MeOH 90:10

1H-NMR (CDCl$_3$): δ 1.30 (t, 3H, H1); 1.45 (s, 9H, tBu); 1.95 (s, 3H, H9); from 1.85 to 2.05 (m, 4H, H7 and H7'); 2.72 (m, 1H, H6); 2.95 (m, 2H, H8 or H8'); 3.30 (m, 2H, H2); 3.68 (m, 2H, H8 or H8'); 3.90 (m, 2H, H11); 4.45 (m, 1H, H12); 4.95 (m, 1H, mobile H); 5.12 (s, 2H, —O—CH2-C6H5); 6.19 (m, 1H, mobile H); 6.30 (d, 1H, H3); 6.50 (d, 1H, H5); 7.35 (m, 5H, O—CH2-C6H5); 7.46 (dd, 1H, H4); 8.30 (s, 1H, H10)

MS: 590=(MH+), 534=(MH-tBu+), 400=MH-(tBu and —CO—O—CH2-C6H5)+

Synthesis of 2-benzyloxycarbonylamino-3-[6-(6-ethylamino-3',4',5',6'-tetrahydro-2'H-[2.4']bipyridinyl-1'-yl)-5-methyl-pyrimidin-4-ylamino]-propionic acid bis(trifluoroacetate)

300 mg (0.51 mmol) of tert-butyl 2-benzyloxycarbonylamino-3-[6-(6-ethylamino-3',4',5',6'-tetrahydro-2'H-[2.4']bipyridinyl-1'-yl)-5-methyl-pyrimidin-4-ylamino]-propionate is solubilized in 5 ml of dichloromethane to which 0.5 ml of trifluoroacetic acid is added.

This mixture is stirred at ambient temperature for 4 hours.

After diluting with toluene, the trifluoroacetic acid, dichloromethane and toluene are evaporated off under reduced pressure (2 kPa).

The residue obtained is taken up in a minimum amount of CH2Cl2 then this solution is poured into isopropyl ether.

The precipitate is filtered out and 220 mg of expected product is recovered in the form of a beige solid TLC: Rf=0.7 (silica gel, eluent: CH2Cl2/MeOH 85:15

1H-NMR (MeOD): δ 1.32 (t, 3H, H1); 2.00 (s, 3H, H9); of 1.90 to 2.10 (m, 4H, H7 and H7'); 2.95 to 3.15 (m, 3H, H6 and H8 or H8'); 3.45 (m, 2H, H2); 3.75 (m, 2H, H8 or H8'); 3.80 and 4.00 (2m, 2H, H11); 4.50 (m, 1H, H12); 5.10 (m, 2H, —O—CH2-C6H5); 6.80 (d, 1H, H3); 6.90 (d, 1H, H5); of 7.35 to 7.40 (m, 5H, O—CH2-C6H5); 7.86 (dd, 1H, H4); 8.20 (s, 1H, H10)

MS: 534=(MH+), 400=MH-(CO—O—CH2-C6H5)+

Examples 7 to 11

By operating in a similar manner to the method described in Example 6, the following products are prepared:

| Example | Ester formed | Rf | MS(MH+) |
|---|---|---|---|
| 7 | [structure] | 0.3 | 646 |
| 8 | [structure] | 0.3 | 659 |

-continued
| | | | |
|---|---|---|---|
| 9 | 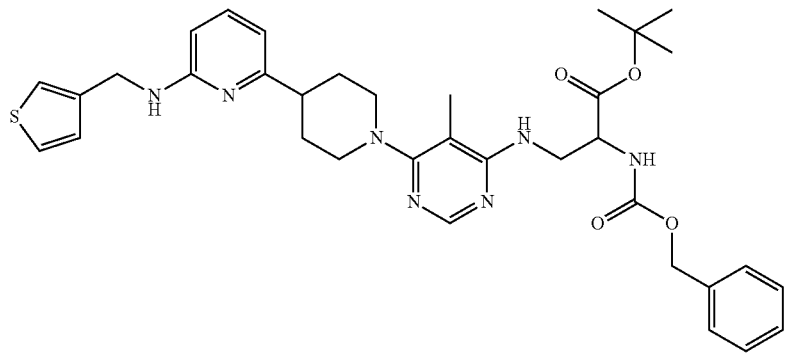 [SMILES: Cc1c(NCC(NC(=O)OCc2ccccc2)C(=O)OC(C)(C)C)ncnc1N1CCC(c2cccc(NCc3ccsc3)n2)CC1] | 0.3 | 659 |
| 10 | 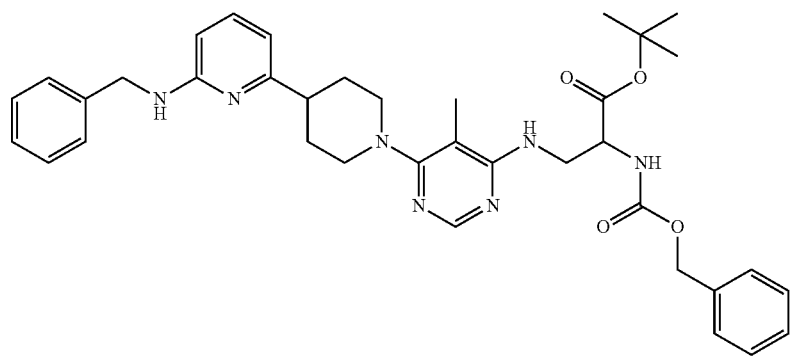 [SMILES: Cc1c(NCC(NC(=O)OCc2ccccc2)C(=O)OC(C)(C)C)ncnc1N1CCC(c2cccc(NCc3ccccc3)n2)CC1] | 0.3 | 653 |
| 11 | 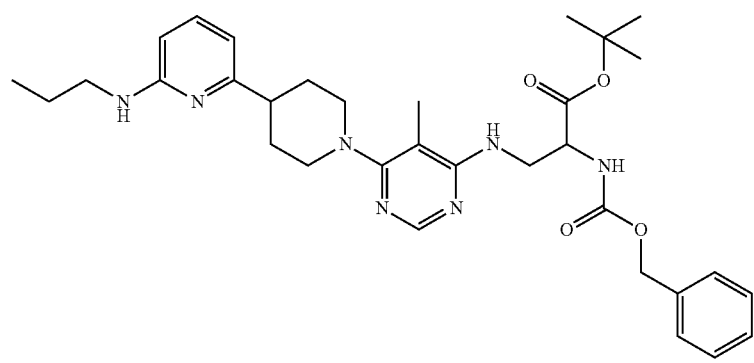 [SMILES: CCCNc1cccc(C2CCN(c3ncnc(NCC(NC(=O)OCc4ccccc4)C(=O)OC(C)(C)C)c3C)CC2)n1] | 0.3 | 604 |
| Example | Acid formed | FW | MS (MH+) | Rf |
|---|---|---|---|---|
| 7 | 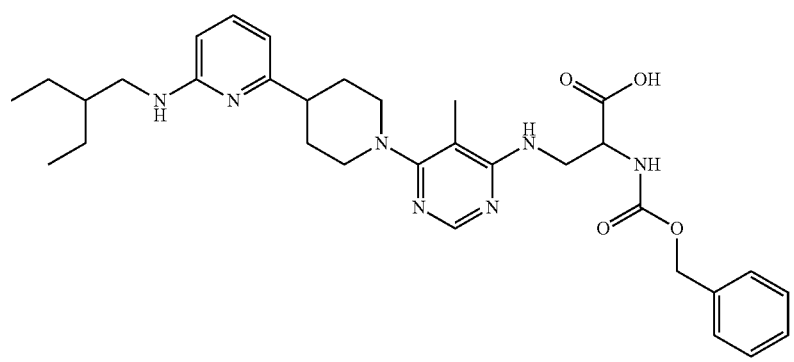 [SMILES: CCC(CC)CNc1cccc(C2CCN(c3ncnc(NCC(NC(=O)OCc4ccccc4)C(=O)O)c3C)CC2)n1] | 589 | 590 | 0.25 |

| | | | | |
|---|---|---|---|---|
| 8 | 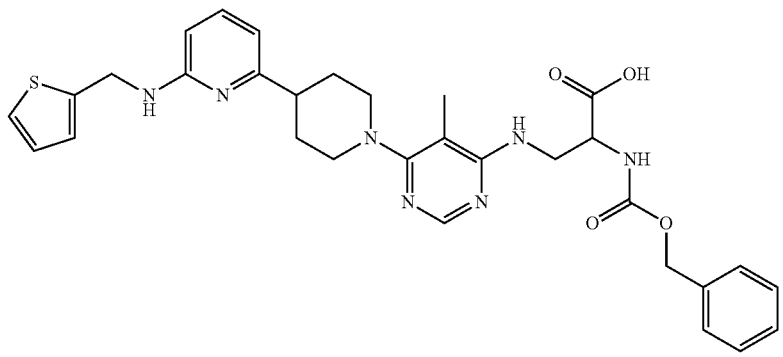 [SMILES: Cc1c(NCC(NC(=O)OCc2ccccc2)C(=O)O)ncnc1N1CCC(c2cccc(NCc3cccs3)n2)CC1] | 601 | 602 | 0.25 |
| 9 | 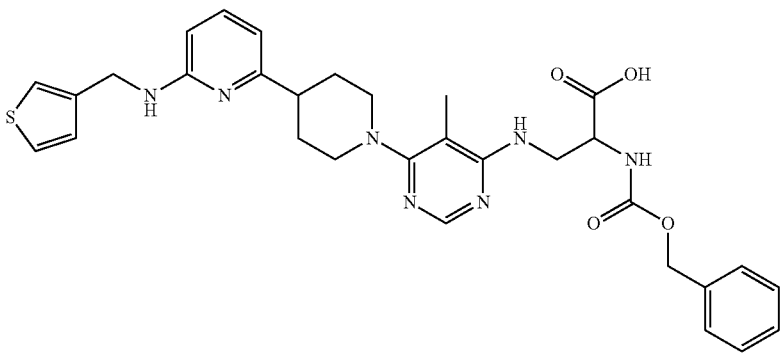 [SMILES: Cc1c(NCC(NC(=O)OCc2ccccc2)C(=O)O)ncnc1N1CCC(c2cccc(NCc3ccsc3)n2)CC1] | 601 | 602 | 0.25 |
| 10 | 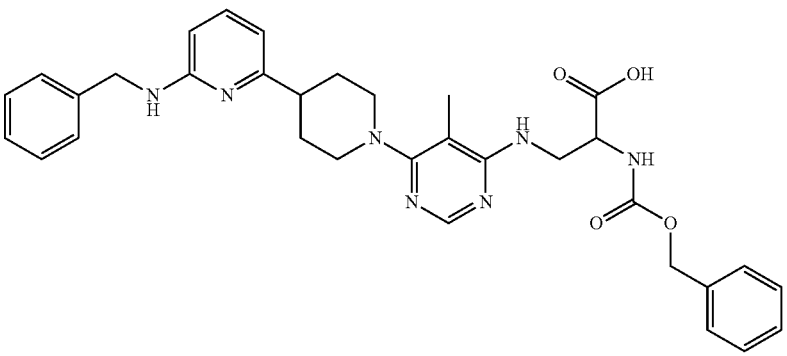 [SMILES: Cc1c(NCC(NC(=O)OCc2ccccc2)C(=O)O)ncnc1N1CCC(c2cccc(NCc3ccccc3)n2)CC1] | 595 | 598 | 0.25 |
| 11 | 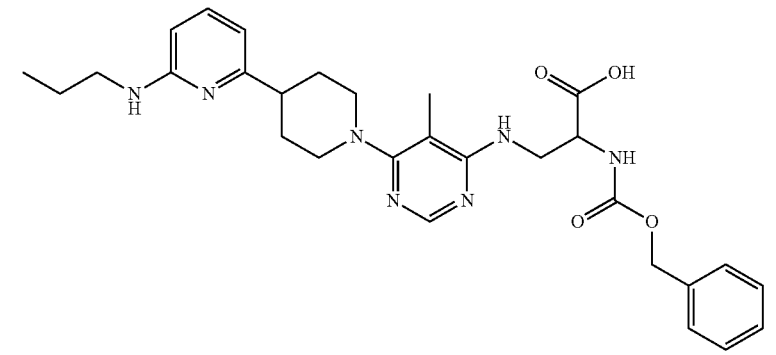 [SMILES: CCCNc1cccc(C2CCN(c3ncnc(NCC(NC(=O)OCc4ccccc4)C(=O)O)c3C)CC2)n1] | 547 | 548 | 0.25 |

Example 12

Synthesis of 2-methyl-4,6-dihydroxy-5-methoxy-pyrimidine 10.8 g (200 mmoles) of sodium methylate is added to a solution of 5.5 g (58 mmoles) of acetamidine hydrochloride in 100 ml of ethanol cooled down to 0° C. and the mixture is stirred for 15 minutes; then a solution of 7.2 ml (52 mmoles) of dimethyl methoxy malonate in 50 ml of ethanol is added and the mixture is stirred overnight at ambient temperature. The reaction mixture is evaporated to dryness under reduced pressure (2 kPa). The residue is taken up in 100 ml of a saturated solution of sodium chloride and extracted with 800 and 200 ml of n-butanol. The organic phases are dried over sodium sulphate, filtered and evaporated to dryness under reduced pressure (2 kPa). 2.4 g of expected product is obtained in the form of a white solid.

1H-NMR (CD$_3$OD): δ 2.31 ppm (s, 3H, C—C$\underline{H_3}$); 3.74 (s, 3H, C—OC$\underline{H_3}$).

MS: 157 (MH+).

Synthesis of 4,6-dichloro-2-methyl-5-methoxy-pyrimidine

A mixture of 1.9 g (12.2 mmoles) of 2-methyl-4,6-dihydroxy-5-methoxy-pyrimidine in 60 ml of phosphorus oxychloride is taken to reflux for 2 hours. After returning to ambient temperature, the reaction mixture is poured into a mixture of ice and water then sodium bicarbonate is added slowly until a basic pH is reached, followed by extracting with ethyl acetate, drying over magnesium sulphate and evaporating to dryness under reduced pressure (2 kPa). 0.67 g (Yield=28%) of a brown oil is obtained.

TLC: Rf=0.40 (silica gel, eluent: heptane-ethyl acetate 90-10).

1H-NMR (CDCl$_3$): δ 2.68 ppm (s, 3H, C—C$\underline{H_3}$); 3.96 (s, 3H, C—OC$\underline{H_3}$).

MS: 193.195 (MH+).

Synthesis of 2-piperidin-4-yl-[1,8]naphthyridine 51 g (300 mmoles) of 4-(2-methyl-[1.3]dioxolan-2-yl)-piperidine (prepared according to J. Org. Chem.; 29; 1964; 2898-2903) is solubilized in 550 ml of ethanol.

This mixture is cooled down to 0° C. using an ice bath.

85 ml of 6N hydrochloric acid (510 mmoles) is added.

The mixture is heated under reflux of ethanol for 24 hours.

Then 20.4 g (510 mmoles) of soda in pellets is added in order to neutralize the pH then 32.13 g (260 mmoles) of 2-aminopyridine-3-carboxyaldehyde and 200 ml of ethanol are added.

Finally 40.8 g (295 mmoles) of potassium carbonate is added.

This mixture is stirred at 100° C. for 8 hours then for 18 hours at ambient temperature.

The ethanol is evaporated off under reduced pressure, then diluted with water and with butanol. The 2 phases are separated and the product is thus extracted with butanol.

The organic phase is dried over sodium sulphate then filtered and evaporated under reduced pressure.

A brown solid is recovered, 65 g of which is used without purification for the following.

TLC: Rf=0.1 (silica gel, eluent: CH2Cl2/MeOH/NH4OH 89:10:1

1H-NMR (MeOD): δ from 1.90 to 2.10 (m, 4H, $\underline{H7}$ and $\underline{H7'}$); from 2.8 to 2.90 (m, 2H, H8 or H8'); from 3.12 to 3.28 (m, 3H, H6+H8 or H8'); from 7.58 to 7.68 (m, 2H, H2 and H5); from 8.38 to 8.45 (m, 2H, H3 and H4); 9.03 (m, 1H, H1).

MS: 270 (MH+)

Synthesis of 2-[1-(6-Chloro-5-methoxy-2-methyl-pyrimidin-4-yl)-piperidin-4-yl]-[1,8]naphthyridine 30 ml of dimethylacetamide, 0.9 g (4.66 mmoles) 4,6-dichloro-2-methyl-5-methoxy-pyrimidine and 3 ml of diisopropylethylamine are added into a single-necked flask containing 1.1 g (5.2 mmoles) of 2-piperidin-4-yl-[1,8] naphthyridine. This mixture is heated at 120° C. for 4 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The residue is chromatographed on silica gel eluting with a gradient of heptane-ethyl acetate of 100-0 to 0-100. 870 mg of expected product is obtained in the form of a yellow solid.

TLC: Rf=0.25 [silica gel, eluent: ethyl acetate (100%)]

1H-NMR (CDCl$_3$): δ 2.16 ppm (m, 4H, N—CH2-CH2-CH—CH2); 2.47 (s, 3H, C—C$\underline{H_3}$); 3.11 and 4.84 (m and bd, 4H, C$\underline{H2}$, CH2-N—CH2-C$\underline{H2}$); 3.26 (m, 1H, CH2-CH—CH2,); 3.75 (s, 3H, C—OC$\underline{H_3}$); 7.45 and 8.16 (2d, 2H, C—CH═CH—C(CH)═N); 7.47 (dd, 1H, N—CH═CH—C$\underline{H}$═C); 8.18 (dd, 1H, N—CH═CH—C$\underline{H}$═C); 9.11 (dd, 1H, N—CH═CH—CH═C).

MS: 370.372 (MH+).

Synthesis of tert-butyl 2-benzyloxycarbonylamino-3-[5-methoxy-2-methyl-6-(4-[1,8]naphthyridin-2-yl-piperidin-1-yl)-pyrimidin-4-ylamino]-propionate A mixture of 870 mg (2.36 mmoles) of 2-[1-(6-chloro-5-methoxy-2-methyl-pyrimidin-4-yl)-piperidin-4-yl]-[1,8] naphthyridine, 766 mg (2.59 mmoles) of tert-butyl 3-amino-2-benzyloxycarbonylamino propionate, 540 mg (3.57 mmoles) of cesium fluoride, 120 mg (0.124 mmole) of tris (dibenzylideneacetone) dipalladium (0), and 70 mg (0.108 mmole) of 2,2'-bis(diphenyl-phosphino)-1,1'-binaphthyl in 50 ml of dioxane is heated under reflux for 6 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent evaporated off under reduced pressure (2 kPa). The residue is chromatographed a first time on alumina eluting with ethyl acetate-ethyl ether 50-50 then a second time on silica eluting with ethyl acetate-heptane 50-50. 820 mg of expected product is obtained in the form of an amorphous white solid.

TLC: Rf=0.30 (silica gel, eluent: ethyl acetate).

1H-NMR (CDCl$_3$): δ 1.47 ppm (s, 1H, tBu); 2.07 to 2.16 (m, 4H, N—CH2-CH2-CH—CH2); 2.38 (s, 3H, C—C$\underline{H_3}$); 2.97 and 4.53 (m and bd, 4H, C$\underline{H2}$-CH2-N—CH2-C$\underline{H2}$); 3.19 (m, 1H, CH2-CH—CH2,); 3.63 (s, 3H, C—OC$\underline{H_3}$); 3.86 (m, 2H, NH—C$\underline{H_2}$—CH—NH); 4.36 (m, 1H, NH—CH$_2$—CH—NH); 5.12 (d, 2H, CH$_2$-Ph); 7.35 (m, 5H, CH2Ph); 7.46 and 8.15 (2d, 2H, C—CH═CH—C(CH)═N); 7.48 (dd, 1H, N—CH═CH—C$\underline{H}$═C); 8.18 (dd, 1H, N—CH═CH—C$\underline{H}$═C); 9.10 (dd, 1H, N—CH═CH—CH═C).

MS: 628 (MH+); 438 (MH-COOCH2Ph+).

Synthesis of tert-butyl 2-benzyloxycarbonylamino-3-{5-methoxy-2-methyl-6-[4-(5,6,7,8-tetrahydro-[1,8] naphthyridin-2-yl)-piperidin-1-yl]-pyrimidin-4-ylamino}-propionate A mixture of 820 mg (1.3 mmoles) of tert-butyl 2-benzyloxycarbonylamino-3-[5-methoxy-2-methyl-6-(4-[1,8] naphthyridin-2-yl-piperidin-1-yl)-pyrimidin-4-ylamino]-propionate and 30 mg of platinum oxide in 50 ml of ethanol is stirred for 2 hours under hydrogen at atmospheric pressure. The reaction mixture is filtered on Clarcel then evaporated to dryness under reduced pressure (2 kPa). The residue is crystallized from diisopropyl ether. 570 mg of expected product is obtained in the form of an amorphous white solid.

TLC: Rf=0.28 (silica gel, eluent: ethyl acetate).

1H-NMR (CDCl$_3$): δ 1.48 ppm (s, 1H, tBu); 1.67 and 1.97 (m, 6H, CH$_2$—C$\underline{H_2}$—CH$_2$—NH and C$\underline{H_2}$—CH—C$\underline{H_2}$); 2.35

(s, 3H, C—CH₃); 2.65 (tt, 1H, CH₂—CH—CH₂); 2.71 (t, 2H, CH₂—CH₂—CH₂—NH); 2.87 and 4.47 (bt and bd, 4H, CH2-CH2-N—CH2-CH2); 3.41 (m, 2H, CH₂—CH₂-CH₂—NH); 3.57 (s, 3H, C—OCH₃); 3.84 (m, 2H, NH—CH₂—CH—NH); 4.36 (m, 1H, NH—CH₂—CH—NH); 5.12 (d, 2H, CH₂-Ph); 6.38 and 7.11 (2d, 2H, C═CH═CH═C); 7.36 (m, 5H, CH2Ph); 4.75 and 5.27 (m; bt and bd Mobile H's).

MS: 632 (MH+); 442 (MH-COOCH2Ph+).

Example 13

Synthesis of 2-benzyloxycarbonylamino-3-{2-methoxy-5-methyl-6-[4-(5,6,7,8-tetrahydro-[1,8]naphthyridin-2-yl)-piperidin-1-yl]-pyrimidin-4-ylamino}-propionic acid bis(trifluoroacetate)

280 mg (0.443 mmole) of tert-butyl 2-benzyloxycarbonylamino-3-{5-methoxy-2-methyl-6-[4-(5,6,7,8-tetrahydro-[1,8]naphthyridin-2-yl)-piperidin-1-yl]-pyrimidin-4-ylamino}-propionate in 15 ml of dichloromethane with 3 ml of trifluoroacetic acid is stirred at ambient temperature for 18 hours. Toluene is added and the reaction mixture is evaporated to dryness under reduced pressure (2 kPa). The residue is solubilized in the minimum amount of dichloromethane then poured into diisopropyl ether. 210 mg of expected product is obtained by filtration in the form of a white solid.

TLC: Rf=0.45 (silica gel, eluent: methylene chloride-methanol-water-acetic acid 90-10-1-1).

1H-NMR (CDCl₃): δ 1.75 and 2.10 ppm (m, 6H, CH₂—CH₂—CH₂—NH and CH₂—CH—CH₃); 2.50 (s, 3H, C—CH₃); 2.78 (bt, 2H, CH₂—CH₂—CH₂—NH); 3.05 (bt, 1H, CH₂—CH—CH₂); 3.50 and 4.79 (bt and bd, 4H, CH2-CH2-N—CH2CH2); 3.51 (m, 2H, CH₂—CH₂—CH₂—NH); 3.57 (s, 3H, C—OCH₃); 3.95 and 4.01 (2m, 2H, NH—CH₂—CH—NH); 4.51 (m, 1H, NH—CH₂—CH—NH); 5.11 (d, 2H, CH₂-Ph); 6.39 and 7.39 (2d, 2H, C═CH═CH═C); 7.30 (m, 5H, CH2Ph); 9.71 (m mobile H's).

MS: 576 (MH+); 442 (MH-COOCH2Ph+); 574 (MH–); 466 (574-OCH2Ph–); 1150 (2M–).

Example 14

Synthesis of 2-tert-butyl-5-methyl-4,6-dihydroxy-pyrimidine

A single-necked flask containing 80 ml of ethanol is cooled down to 0° C. by an ice bath, 4 g (55.6 mmoles) of sodium ethylate and 3.8 g (27.8 mmoles) of tert-butylcarbamidine hydrochloride are added. The reaction mixture is left to return to ambient temperature, then 5 ml (27.8 mmoles) of diethyl ester methylmalonate is added dropwise. Stirring is maintained at ambient temperature overnight. The ethanol is then condensed under reduced pressure (2 kPa). The crude product obtained is solubilized in a minimum amount of water (approximately 40 ml), then acidified at 0° C. with pure acetic acid until a pH comprised between 4 and 5 is achieved. The white precipitate formed is filtered, rinsed successively with water, ethyl ether and with pentane. Then the white powder obtained is dried over P₂O₅ under reduced pressure (0.2 kPa). 2.4 g of expected product is obtained.

TLC: Rf=0.56 (silica gel, eluent: dichloromethane-methanol 90-10).

MS: (MH+)=183, (MH–)=181
1H-NMR (DMSOd6): δ 1.25 (s, 9H, tert-butyl); 1.72 (s, 3H, N═C—CH3).

Synthesis of
2-tert-butyl-4,6-dichloro-5-methyl-pyrimidine

A mixture of 2.91 g (15.9 mmoles) of 2-tert-butyl-5-methyl-4,6-dihydroxy-pyrimidine and 15 ml of phosphorus oxychloride is taken to reflux for 1 hour 30 minutes. After returning to ambient temperature, the reaction mixture is poured slowly into a mixture of ice, water and solid sodium carbonate. This aqueous phase is extracted with ethyl acetate. The organic phase is washed several times with a saturated solution of sodium bicarbonate until total neutralization of the acid is achieved then dried over magnesium sulphate and evaporated to dryness under reduced pressure (2 kPa). 3.27 g of expected product is obtained.

TLC: Rf=0.63 (silica gel, eluent: cyclohexane-ethyl acetate 98-2)

1H-NMR (CDCl₃): δ 1.38 (s, 9H, tert-butyl); 2.45 (s, 3H, N═C—CH3).

MS: (MH+)=210.

Synthesis of 2-[1-(2-tert-butyl-6-chloro-5-methyl-pyrimidin-4-yl)-piperidin-4-yl]-[1,8]naphthyridine 20 ml of dimethylacetamide and 5 ml (17.8 mmoles) of diisopropylethylamine are added into a single-necked flask containing 1.5 g (6.84 mmoles) of 2-tert-butyl-4,6-dichloro-5-methyl-pyrimidine and 1.46 g (6.84 mmoles) of 2-piperidin-4-yl-[1,8]naphthyridine. This mixture is heated at 100° C. overnight. The next day 0.2 equivalent of naphthyridine is added and the mixture is heated for another 6 hours. The reaction mixture is returned to ambient temperature before concentrating to dryness. The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The residue is chromatographed on silica gel eluting with a gradient of heptane-ethyl acetate (70-30) to heptane-ethyl acetate (50-50). 1.77 g of expected product is obtained.

TLC: Rf=0.50 [silica gel, eluent heptane-ethyl acetate (50-50).

1H-NMR (CDCl₃): δ 1.37 (s, 9H, tert-butyl); 2.1 (m, 1H, cyclopropyl); 2.15 (m, 4H, N—CH2-CH2-CH—CH2-CH2); 2.27 (s, 3H, CH3); 3.1 and 4.05 (2m, 4H, CH2-CH2-N—CH2-CH2); 3.25 (m, 1H, N—CH2-CH2-CH—CH2-CH2); [(7.48; 8.18; 9.12), 3m, 5H, naphthyridine].

MS: 396 (MH+).

Synthesis of tert-butyl 2-benzyloxycarbonylamino-3-[2-tert-butyl-5-methyl-6-(4-[1,8]naphthyridin-2-yl-piperidin-1-yl)-pyrimidin-4-ylamino]-propionate A mixture of 1.7 g (4.2 mmoles) of 2-[1-(2-tert-butyl-6-chloro-5-methyl-pyrimidin-4-yl)-piperidin-4-yl]-[1,8]naphthyridine and 1.51 g (5.04 mmoles) of tert-butyl 3-amino-2-benzyloxycarbonylamino propionate, in the presence of 1.95 g (12.6 mmoles) of cesium fluoride, 266 mg (0.42 mmoles) of (2,2'-bis(diphenylphosphino)-1,1'-binaphthyl in 20 ml of dioxane is taken to reflux, 230 mg (0.21 mmoles) of tris-dibenzylideneacetone) dipalladium (o) solubilized in 5 ml of dioxane is added hot, then the reaction medium is left under reflux for 15 hours. The reaction mixture is then taken to ambient temperature, concentrated to dryness under reduced pressure (2 kPa) then taken up in a mixture of water, ethyl acetate and a saturated solution of sodium bicarbonate. The organic phase is decanted and the aqueous phase is extracted with ethyl acetate. The collected organic phases are dried over magnesium sulphate and evaporated to dryness under reduced pressure (2 kPa). The residue is chromatographed on silica with a gradient of dichloromethane-ethyl acetate (95-5) until to (70-30). 1.91 g of expected product is obtained.

TLC: Rf=0.17 (silica gel, eluent: dichloromethane-ethyl acetate (70-30)

1H-NMR (CDCl$_3$): δ 1.33 (s, 9H, tert-butyl); 1.48 (s, 9H, tBu); 1.95 (s, 3H, CH3); 2.08 to 2.25 (m, 4H, N—CH2-CH2-CH—CH2-CH2); 3.0 and 3.8 (2m, 4H, CH2-CH2-N—CH2-CH2); 3.18 (m, 1H, N—CH2-CH2-CH—CH2-CH2); 3.83 to 4.0 (2m, 2H, NH—CH2-CH—NH); 4.35 (m, 1H, NH—CH2-CH—NH); 4.65 and 7.3 (2m, 2H, NH); 5.1 (s, 2H, O—CH2-Ph); 7.32 (m, 5H, phenyl); [(7.47; 8.17; 9.12), (3m, 5H, naphthyridine).

MS: 654 (MH+), 464 (MH-CBZ-tbu)

Synthesis of tert-butyl 2-benzyloxycarbonylamino-3-[2-tert-butyl-5-methyl-6-[4-(5,6,7,8-tetrahydro-[1,8] naphthyridin-2-yl-piperidin-1-yl)-pyrimidin-4-ylamino]-propionate 120 mg of platinum (IV) oxide is added to 1.8 g (2.75 mmoles) of tert-butyl 2-benzyloxycarbonylamino-3-[2-tert-butyl-5-methyl-6-(4-[1,8]naphthyridin-2-yl-piperidin-1-yl)-pyrimidin-4-ylamino]-propionate solubilized in 80 ml of ethanol. The reaction mixture is then purged under vacuum and surmounted by a balloon flask containing hydrogen, then left under stirring and at ambient temperature for 6 hours. The reaction mixture is then filtered on Clarcel and concentrated to dryness under reduced pressure (2 kPa). The residue is chromatographed on silica with a gradient of dichloromethane-methanol (98-2). 1.6 g of expected product is obtained.

TLC: Rf=0.76 [silica gel, eluent: dichloromethane-methanol 90-10]

1H-NMR (CDCl$_3$): δ 1.3 (s, 9H, tBu); 1.48 (s, 9H, tBu); 1.7 to 2.0 (m, 9H, CH3, CH2-CH2-CH2-NH, N—CH2-CH2-CH—CH2-CH2); 2.63 (m, 1H, N—CH2-CH2-CH—CH2-CH2); 2.71 (t, 2H, CH2-CH2-CH2-NH); 2.9 and 3.73 (2m, 4H, CH2-CH2-N—CH2-CH2); 3.41 (m, 2H, CH2-CH2-CH2-NH); 3.8 to 4.3 (2m, 2H, NH—CH2-CH—NH); 4.35 (m, 1H, NH—CH2-CH—NH); [(4.56; 4.75; 7.03), 3m, 3H, NH); 5.08 (s, 2H, O—CH2-Ph); 6.4 and 7.12 (2d, 2H, naphthyridine); 7.32 (m, 5H, phenyl).

MS: 658 (MH+).

Example 15

2-benzyloxycarbonylamino-3-[2-tert-butyl-5-methyl-6-[4-(5,6,7,8-tetrahydro-[1,8]naphthyridin-2-yl-piperidin-1-yl)-pyrimidin-4-ylamino]-propionic acid (bis trifluoroacetate)

A mixture of 350 mg (0.53 mmoles) of tert-butyl 2-benzyloxycarbonylamino-3-[2-tert-butyl-5-methyl-6-[4-(5,6,7,8-tetrahydro-[1,8]naphthyridin-2-yl-piperidin-1-yl)-pyrimidin-4-ylamino]-propionate solubilized in 6 ml of dichloromethane and 2.2 ml of trifluoroacetic acid is stirred at ambient temperature for 24 hours. Then toluene is added and the mixture is evaporated to dryness. The residue is solubilized in a minimum amount of dichloromethane then poured into a mixture of pentane and diisopropyl ether. The precipitate is filtered. An impure white powder is obtained which must be purified on silica with a gradient of 100% dichloromethane to dichloromethane-methanol (90-10).

390 mg of expected product is obtained.

TLC: Rf=0.27 (silica gel, eluent: dichloromethane-methanol-water-acetic acid 90-10-1-1).

1H-NMR (CDCl$_3$): δ 1.37 (s, 9H, tBu); 1.75 (m, 2H, CH2-CH2-CH2-NH); 1.90 to 2.05 (m, 5H, CH3, N—CH2-CH2-CH—CH2-CH2); 2.75 (t, 2H, CH2-CH2-CH2-NH); 3.02 (m, 1H, N—CH2-CH2-CH—CH2-CH2); 3.15 and 3.77 (2m, 4H, CH2-CH2-N—CH2-CH2); 3.5 (m, 2H, CH2-CH2-CH2-NH); 4.17 (m, 3H, NH—CH2-CH—NH, NH—CH2-CH—NH); 5.08 (s, 2H, O—CH2-Ph); 6.4 and 7.35 (2d, 2H, naphthyridine); 6.12 (m, 1H, NH); 7.2 to 7.35 (m, 5H, phenyl); 10.05 (m, 1H, OH acid).

MS: 602 (MH+); 600 (MH−)

Example 16

Synthesis of 2-methyl-5-cyclopropyl-4,6-dihydroxy-pyrimidine

A single-necked flask containing 80 ml of ethanol is cooled down to 0° C. using an ice bath, 4.5 g (66.4 mmoles) of sodium ethylate and 4 g (33.2 mmoles) of cyclopropylcarbamidine hydrochloride are added. The reaction mixture is left to return to ambient temperature, then 5.7 ml (33.2 mmoles) of diethyl ester methylmalonate is added dropwise. Stirring is maintained at ambient temperature overnight. The ethanol is then condensed under reduced pressure (2 kPa). The crude product obtained is solubilized in a minimum amount of water (approximately 40 ml), then acidified at 0° C. with pure acetic acid until a pH comprised between 4 and 5 is achieved. The white precipitate formed is filtered, rinsed successively with water, ethyl ether and with pentane. Then the white powder obtained is dried over P$_2$O$_5$ under reduced pressure (0.2 kPa). 3 g of expected product is obtained.

TLC: Rf=0.36 (silica gel, eluent: dichloromethane-methanol 90-10).

MS: (MH+)=167, (MH−)=165

1H-NMR (DMSOd6): δ 0.95 (m, 4H, cyclopropyl); 1.67 (s, 3H, N=C—CH3); 1.83 (m, 1H, cyclopropyl).

Synthesis of 2-cyclopropyl-4,6-dichloro-5-methyl-pyrimidine

A mixture of 3.68 g (22 mmoles) of 2-cyclopropyl-5-methyl-4,6-dihydroxy-pyrimidine and 20 ml of phosphorus oxychloride, is taken to reflux for 1 hour and 30 minutes. After returning to ambient temperature, the reaction mixture is poured slowly into a mixture of ice, water and solid sodium carbonate. This aqueous phase is extracted with ethyl acetate. The organic phase is washed several times with a saturated solution of sodium bicarbonate until total neutralization of the acid is achieved then dried over magnesium sulphate and evaporated to dryness under reduced pressure (2 kPa). 4.26 g (Yield=95%) of expected product is obtained.

TLC: Rf=0.56 (silica gel, eluent: cyclohexane-ethyl acetate 98-2)

1H-NMR (CDCl$_3$): δ 1.07 to 1.2 (m, 4H, cyclopropyl); 2.18 (m, 1H, cyclopropyl); 2.42 (s, 3H, N=C—CH3);

MS: (MH+)=204.

Synthesis of 2-[1-(2-cyclopropyl-6-chloro-5-methyl-pyrimidin-4-yl)-piperidin-4-yl]-[1,8]naphthyridine 20 ml of dimethylacetamide and 3.36 ml (19.2 mmoles) of diisopropylethylamine are added into a single-necked flask containing 1.5 g (7.39 mmoles) of 2-cyclopropyl-4,6-dichloro-5-methyl-pyrimidine and 1.58 g (7.39 mmoles) of 2-piperidin-4-yl-[1,8]naphthyridine. This mixture is heated at 100° C. overnight. The next day 0.2 equivalent of naphthyridine is added and the reaction mixture is heated for another 6 hours, followed by returning to ambient temperature before concentration to dryness. The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The residue is chromatographed on silica gel eluting with a gradient of heptane-ethyl acetate (50-50) to 100% ethyl acetate. 1.45 g of expected product is obtained.

TLC: Rf=0.28 [silica gel, eluent heptane-ethyl acetate (50-50).

1H-NMR (CDCl$_3$): δ 0.98 and 1.09 (2m, 4H, cyclopropyl); 2.1 (m, 1H, cyclopropyl); 2.15 (m, 4H, N—CH2-CH2-CH—CH2-CH2); 2.25 (s, 3H, CH3); 3.05 and 4.0 (2m, 4H, CH2-CH2-N—CH2-CH2); 3.23 (m, 1H, N—CH2-CH2-CH—CH2-CH2); [(7.05; 8.2; 9.13), 3m, 5H, naphthyridine].

MS: 380 (MH+).

Synthesis of tert-butyl 2-benzyloxycarbonylamino-3-[2-cyclopropyl-5-methyl-6-(4-[1,8]naphthyridin-2-yl-piperidin-1-yl)-pyrimidin-4-ylamino]-propionate A mixture of 1.4 g (3.68 mmoles) of 2-[1-(2-tert-butyl-6-chloro-5-methyl-pyrimidin-4-yl)-piperidin-4-yl]-[1,8]naphthyridine and 1.3 g (4.42 mmoles) of tert-butyl 3-amino-2-benzyloxycarbonylamino propionate in the presence of 1.68 g (11 mmoles) of cesium fluoride, 230 mg (0.37 mmoles) and (2,2'-bis(diphenylphosphino)-1,1'-binaphthyl in 20 ml of dioxane is taken to reflux. 200 mg (0.19 mmoles) of tris-dibenzylideneacetone) dipalladium (o) solubilized in 5 ml of dioxane is added hot, then left under reflux for 15 hours. The reaction mixture is then taken to ambient temperature, and concentrated to dryness under reduced pressure (2 kPa) then taken up in a mixture of water, ethyl acetate and a saturated solution of sodium bicarbo-nate. The organic phase is decanted and the aqueous phase is extracted with ethyl acetate. The collected organic phases are dried over magnesium sulphate and evaporated to dryness under reduced pressure (2 kPa). The residue is chromatographed on alumina then on silica with a gradient of dichloromethane-ethyl acetate (95-5) to (70-30). 1.5 g of expected product is obtained.

TLC: Rf=0.17 (silica gel, eluent: dichloromethane-ethyl acetate (70-30)

1H-NMR (CDCl$_3$): δ 0.82 and 1.05 (2m, 4H, cyclopropyl); 1.45 (s, 9H, tBu); 1.93 (s, 3H, CH3); 1.97 (m, 1H, cyclopropyl); 2.07 to 2.25 (m, 4H, N—CH2-CH2-CH—CH2-CH2); 3.0 and 3.73 (2m, 4H, CH2-CH2-N—CH2-CH2); 3.15 (m, 1H, N—CH2-CH2-CH—CH2-CH2); 3.73 to 4.0 (2m, 2H, NH—CH2-CH—NH); 4.36 (m, 1H, NH—CH2-CH—NH); 4.65 and 8.87 (2m, 2H, NH); 5.12 (s, 2H, O—CH2-Ph); 7.33 (m, 5H, phenyl); [(7.47; 8.15; 9.1), (3m, 5H, naphthyridine).

MS: 638 (MH+), 448 (MH-CBZ-tBu)

Synthesis of tert-butyl 2-benzyloxycarbonylamino-3-[2-cyclopropyl-5-methyl-6-[4-(5,6,7,8-tetrahydro-[1, 8]naphthyridin-2-yl-piperidin-1-yl)-pyrimidin-4-ylamino]-propionate 100 mg of platinum (IV) oxide is added to 1.4 g (2.19 mmoles) of tert-butyl 2-benzyloxycarbonylamino-3-[2-cyclopropyl-5-methyl-6-(4-[1,8]naphthyridin-2-yl-piperidin-1-yl)-pyrimidin-4-ylamino]-propionate solubilized in 60 ml of ethanol. The reaction mixture is then purged under vacuum and surmounted by a balloon flask containing hydrogen. The reaction mixture is left under stirring and at ambient temperature for 6 hours, then filtered on Clarcel and concentrated to dryness under reduced pressure (2 kPa). The residue is chromatographed on silica with a gradient of dichloromethane-methanol (98-2). 1.23 g of expected product is obtained.

TLC: Rf=0.10 [silica gel, eluent: dichloromethane-methanol 98-2]

1H-NMR (CDCl$_3$): δ 0.82 and 1.05 (2m, 4H, cyclopropyl); 1.45 (s, 9H, tBu); 1.68 (m, 1H, cyclopropyl); 1.75 to 2.0 (m, 9H, CH3, CH2-CH2-CH2-NH, N—CH2-CH2-CH—CH2-CH2); 2.6 (m, 1H, N—CH2-CH2-CH—CH2-CH2); 2.72 (t, 2H, CH2-CH2-CH2-NH); 2.9 and 3.65 (2m, 4H, CH2-CH2-N—CH2-CH2); 3.43 (m, 2H, CH2-CH2-CH2-NH); 3.75 to 4.0 (2m, 2H, NH—CH2-CH—NH); 4.36 (m, 1H, NH—CH2-CH—NH); [(4.6; 4.75; 6.87), 3m, 3H, NH); 5.1 (s, 2H, O—CH2-Ph); 6.42 and 7.12 (2d, 2H, naphthyridine); 7.33 (m, 5H, phenyl).

MS: 642 (MH+).

Example 17

2-benzyloxycarbonylamino-3-[2-cyclopropyl-5-methyl-6-[4-(5,6,7,8-tetrahydro-[1,8]naphthyridin-2-yl-piperidin-1-yl)-pyrimidin-4-ylamino]-propionic acid (bistrifluoroacetate)

A mixture of 300 mg (0.47 mmoles) of tert-butyl 2-benzyloxycarbonylamino-3-[2-cyclopropyl-5-methyl-6-[4-(5,6,7,8-tetrahydro-[1,8]naphthyridin-2-yl-piperidin-1-yl)-pyrimidin-4-ylamino]-propionate solubilized in 5 ml of dichloromethane and 2 ml of trifluoroacetic acid is stirred at ambient temperature for 24 hours. Then toluene is added and the mixture is evaporated to dryness. The residue is solubilized in a minimum amount of dichloromethane then poured into a mixture of pentane and diisopropyl ether. The precipitate is filtered. An impure white powder is obtained which must be purified on silica with a gradient of 100% dichloromethane to dichloromethane-methanol (90-10).

320 mg of expected product is obtained.

TLC: Rf=0.16 (silica gel, eluent: dichloromethane-methanol-water-acetic acid 90-10-1-1).

1H-NMR (CDCl$_3$): δ 1.05 (m, 4H, cyclopropyl); 1.95 (m, 9H, CH3, CH2-CH2-CH2-NH, N—CH2-CH2-CH—CH2-CH2); 2.3 (m, 1H, cyclopropyl); 2.77 (t, 2H, CH2-CH2-CH2-NH); 2.85 to 3.2 and 3.95 (3m, 7H, CH2-CH2-N—CH2-CH2, N—CH2-CH2-CH—CH2-CH2, NH—CH2-CH—NH); 3.5 (m, 2H, CH2-CH2-CH2-NH); 4.25 (m, 1H, NH—CH2-CH—NH); 5.1 (s, 2H, O—CH2-Ph); 6.07 (m, 1H, NH); 6.35 (d, 1H, naphthyridine); 7.2 to 7.4 (m, 6H, naphthyridine and phenyl); 10.3 (m, 1H, OH acid).

MS: 586 (MH+); 584 [MH-).

Example 18

Synthesis of 2-methoxy-4,6-dihydroxy-5-methyl-pyrimidine 13.8 g (200 mmoles) of sodium ethylate is added to a solution of 10 g (58 mmoles) of methoxyformamidine sulphate in 100 ml of ethanol cooled down to 0° C. and the mixture is stirred for 15 minutes; then a solution of 9 ml (52 mmoles) of diethyl methyl malonate in 50 ml of ethanol is added followed by stirring overnight at ambient temperature. The reaction mixture is evaporated to dryness under reduced pressure (2 kPa). The residue is taken up in 100 ml of a saturated solution of sodium chloride and extracted with 800 and 200 ml of n-butanol. The organic phases are dried over sodium sulphate, filtered and evaporated to dryness under reduced pressure (2 kPa). 5.9 g of expected product is obtained in the form of a white solid.

1H-NMR (CD$_3$OD): δ 1.85 ppm (s, 3H, C—CH$_3$); 3.95 (s, 3H, C—OCH$_3$).

MS: 157 (MH+); 155 (M-H–).

Synthesis of 4,6-dichloro-2-methoxy 5-methyl-pyrimidine

A mixture of 0.9 g (5.77 mmoles) of 2-methoxy-4,6-dihydroxy-5-methyl-pyrimidine in 30 ml of phosphorus oxychloride is taken to reflux for 2 hours. After returning to ambient temperature, the reaction mixture is poured into a mixture of ice and water then sodium bicarbonate is slowly added until a basic pH is achieved, followed by extracting with ethyl acetate, drying over magnesium sulphate and evaporating to dryness under reduced pressure (2 kPa). 0.43 g (Yield=38%) of a brown oil is obtained.

TLC: Rf=0.5 (silica gel, eluent: heptane-ethyl acetate 80-20).

1H-NMR (CDCl$_3$): δ 2.68 ppm (s, 3H, C—CH$_3$); 3.94 (s, 3H, C—OCH$_3$).

MS: 193.195 (MH+).

Synthesis of 2-[1-(6-chloro-2-methoxy-5-methyl-pyrimidin-4-yl)-piperidin-4-yl]-[1,8]naphthyridine 30 ml of dimethylacetamide, 0.4 g of 4,6-dichloro-2-methoxy-5-methyl-pyrimidine (2 mmoles) and 3 ml of diisopropylethylamine are added into a single-necked flask containing 0.48 g (2.2 mmoles) of 4-(1,8-naphthyridin-7-yl)-1-piperidine. This mixture is heated at 120° C. for 4 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The residue is chromatographed on silica gel eluting with a gradient of heptane-ethyl acetate of 100-0 to 0-100. 460 mg of expected product is obtained in the form of a yellow solid.

TLC: Rf=0.28 [silica gel, eluent: ethyl acetate (100%)]

1H-NMR (CDCl$_3$): δ 2.17 ppm (m, 4H, N—CH2-CH2-CH—CH2); 2.25 (s, 3H, C—CH$_3$); 3.11 and 4.06 (dt and bd, 4H, CH2-CH2-N—CH2-CH2); 3.23 (m, 1H, CH2-CH—CH2,); 3.96 (s, 3H, C—OCH$_3$); 7.47 and 8.17 (2d, 2H, C—CH═CH—C(CH)═N); 7.48 (dd, 1H, N—CH═CH—CH═C); 8.19 (dd, 1H, N—CH═CH—CH═C); 9.12 (dd, 1H, N—CH═CH—CH═C).

MS: 370.372 (MH+).

Synthesis of tert-butyl 2-benzyloxycarbonylamino-3-[2-methoxy-5-methyl-6-(4-[1,8]naphthyridin-2-yl-piperidin-1-yl)-pyrimidin-4-ylamino]-propionate A mixture of 460 mg (1.25 mmoles) 2-[1-(6-chloro-2-methoxy-5-methyl-pyrimidin-4-yl)-piperidin-4-yl]-[1,8] naphthyridine, 405 mg (1.37 mmoles) of tert-butyl 3-amino-2-benzyloxycarbonylamino propionate, 250 mg (1.65 mmoles) of cesium fluoride, 57 mg (0.062 mmole) of tris(dibenzylideneacetone) dipalladium (0), and 40 mg (0.062 mmole) of 2,2'-bis(diphenyl-phosphino)-1,1'-binaphthyl in 50 ml of dioxane is heated under reflux for 2 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on alumina eluting with a gradient of heptane-ethyl acetate of 100-0 to 0-100. 300 mg of expected product is obtained in the form of an amorphous yellow solid.

TLC: Rf=0.27 (silica gel, eluent: ethyl acetate).

1H-NMR (CDCl$_3$): δ 1.48 ppm (s, 1H, tBu); 1.91 (s, 3H, C—CH$_3$); 2.10 to 2.26 (m, 4H, N—CH2-CH2-CH—CH2); 3.01 and 3.79 (bt and bd, 4H, CH2-CH2-N—CH2-CH2); 3.17 (m, 1H, CH2-CH—CH2,); 3.85 and 3.97 (2m, 2H, NH—CH$_2$—CH—NH); 3.91 (s, 3H, C—OCH$_3$); 4.45 (m, 1H, NH—CH$_2$—CH—NH); 5.12 (d, 2H, CH$_2$-Ph); 7.35 (m, 5H, CH2Ph); 7.48 and 8.16 (2d, 2H, C—CH═CH—C(CH)═N); 7.48 (dd, 1H, N—CH═CH—CH═C); 8.19 (dd, 1H, N—CH═CH—CH═C); 9.11 (dd, 1H, N—CH═CH—CH═C); 4.89 and 6.21 (bt and bd mobile H's).

MS: 628 (MH+); 438 (MH-COOCH2Ph+).

Synthesis of tert-butyl 2-benzyloxycarbonylamino-3-{2-methoxy-5-methyl-6-[4-(5,6,7,8-tetrahydro-[1,8]naphthyridin-2-yl)-piperidin-1-yl]-pyrimidin-4-ylamino}-propionate A mixture of 300 mg (0.477 mmole) of tert-butyl-2-benzyloxycarbonylamino-3-[2-methoxy-5-methyl-6-(4-[1,8] naphthyridin-2-yl-piperidin-1-yl)-pyrimidin-4-ylamino]-propionate and 30 mg of platinum oxide in 30 ml of ethanol is stirred for 1 hour under hydrogen at atmospheric pressure. The reaction mixture is filtered on Clarcel then evaporated to dryness under reduced pressure (2 kPa). 170 mg of amine product is obtained in the form of an orange oil.

This amine is reacted with 120 mg of benzyloxycarbonyl-succinimide in 40 ml of dimethoxyethane for 3 hours at ambient temperature. The reaction mixture is taken up in ethyl acetate, water and a saturated solution of sodium bicarbonate. The organic phase is separated, dried over magnesium sulphate and the solvent is evaporated off under reduced pressure (2 kPa). The residue is chromatographed on silica gel eluting with a gradient of heptane-ethyl acetate of 100-0 to 0-100. 200 mg (Yield=93%; 67% for the two stages) of expected product is obtained in the form of a yellow oil.

TLC: Rf=0.18 (silica gel, eluent: ethyl acetate).

1H-NMR (CDCl$_3$): δ1.46 ppm (s, 1H, tBu); 1.77 and 1.97 (m, 6H, CH$_2$—CH$_2$—CH$_2$—NH and CH$_2$—CH—CH$_2$); 1.90 (s, 3H, C—CH$_3$); 2.61 (tt, 1H, CH$_2$—CH—CH$_2$); 2.71 (bt, 2H, CH$_2$—CH$_2$—CH$_2$—NH); 2.91 and 3.72 (bt and bd, 4H, CH2-CH2-N—CH2-CH2); 3.41 (m, 2H, CH$_2$—CH$_2$—CH$_2$—NH); 3.84 and 3.95 (2m, 2H, NH—CH$_2$—CH—NH); 3.89 (s, 3H, C—OCH$_3$); 4.43 (m, 1H, NH—CH$_2$—CH—NH); 5.11 (d, 2H, CH$_2$-Ph); 6.41 and 7.12 (2d, 2H, C═CH═CH═C); 7.36 (m, 5H, CH2Ph); 4.77; 4.85 and 6.21 (m; bt and bd mobile H's).

MS: 632 (MH+); 442 (MH-COOCH2Ph+).

Synthesis of 2-benzyloxycarbonylamino-3-{2-methoxy-5-methyl-6-[4-(5,6,7,8-tetrahydro-[1,8]naphthyridin-2-yl)-piperidin-1-yl]-pyrimidin-4-ylamino}-propionic acid bis(trifluoroacetate)

200 mg (0.317 mmole) of tert-butyl 2-benzyloxycarbonylamino-3-{2-methoxy-5-methyl-6-[4-(5,6,7,8-tetrahydro-[1,8]naphthyridin-2-yl)-piperidin-1-yl]-pyrimidin-4-ylamino}-propionate in 10 ml of dichloromethane with 2 ml of trifluoroacetic acid is stirred at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane then poured into diisopropyl ether. 170 mg of expected product is obtained in the form of a beige solid.

TLC: Rf=0.30 (silica gel, eluent: methylene chloride-methanol-water-acetic acid 90-10-1-1).

1H-NMR (CDCl$_3$) 1.72 and 2.05 ppm (m, 6H, CH$_2$—CH$_2$—CH$_2$—NH and CH$_2$—CH—CH$_2$); 1.93 (s, 3H, C—CH$_3$); 2.77 (bt, 2H, CH$_2$—CH$_2$—CH$_2$—NH); 2.96 (bt, 1H, CH$_2$—CH—CH$_2$); 3.20 and 3.83 (bt and bd, 4H, CH2-CH2-N—CH2-CH2); 3.51 (m, 2H, CH$_2$—CH$_2$—CH$_2$—NH); 3.96 (s, 3H, C—OCH$_3$); 4.01 (m masked, 2H, NH—CH$_2$—CH—NH); 4.44 (m, 1H, NH—CH$_2$—CH—NH); 5.09 (d, 2H, CH$_2$-Ph); 6.41 and 7.36 (2d, 2H, C═CH═CH—C); 7.31 (m, 5H, CH2Ph); 6.49; 8.17 and 9.60 (bd; bm and bs mobile H's).

MS: 576 (MH+); 442 (MH-COOCH2Ph+); 574 (MH-); 466 (574-OCH2Ph-); 1150 (2M-).

Example 19

Synthesis of 2,5-dimethoxy-4,6-dihydroxy-pyrimidine 9.7 g (180 mmoles) of sodium methylate is added to a solution of 9 g (52 mmoles) of methoxyformamidine sulphate in 100 ml of ethanol cooled down to 0° C. and the mixture is stirred for 15 minutes; then a solution of 6.5 ml (46.8 mmoles) of methyl methoxy malonate in 50 ml of ethanol is added, followed by stirring overnight at ambient temperature. The reaction mixture is evaporated to dryness under reduced pressure (2 kPa). The residue is taken up in 100 ml of a saturated solution of sodium chloride and extracted with 800 and 200 ml of n-butanol. The organic phases are dried over sodium sulphate, filtered and evaporated to dryness under reduced pressure (2 kPa). 7 g of expected product is obtained in the form of a white solid.

1H-NMR (CD$_3$OD): δ 3.59 ppm (s, 3H, C—OCH$_3$); 3.91 (s, 3H, C—OCH$_3$), 4.90 (m mobile H's).

MS: 173 (MH+); 171 (M-H-).

Synthesis of 4,6-dichloro-2,5-dimethoxy-pyrimidine

A mixture of 1.7 g (10 mmoles) of 2,5-dimethoxy-4,6-dihydroxy-pyrimidine in 30 ml of phosphorus oxychloride is taken to reflux for 5 hours. After returning to ambient temperature, the reaction mixture is poured into a mixture of ice and water then sodium bicarbonate is added slowly until a basic pH is achieved, followed by extracting with butanol, drying over sodium sulphate and evaporating to dryness under reduced pressure (2 kPa). 0.50 g of a brown oil is obtained.

TLC: Rf=0.5 (silica gel, eluent: heptane-ethyl acetate 80-20).

1H-NMR (CDCl$_3$): δ 3.90 ppm (s, 3H, C—OCH$_3$); 4.01 s, 3H, C—OCH$_3$).

Synthesis of 2-[1-(6-Chloro-2,5-dimethoxy-pyrimidin-4-yl)-piperidin-4-yl]-[1,8]naphthyridine 40 ml of dimethylacetamide, 1.25 g of 4,6-dichloro-2,5-dimethoxy-pyrimidine (5.6 mmoles) and 5 ml of diisopropylethylamine are added into a single-necked flask containing 1.3 g (7.8 mmoles) of 4-(1,8-naphthyridin-7-yl)-1-piperidine. This mixture is heated at 120° C. for 5 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The residue is chromatographed on silica gel eluting with a gradient of heptane-ethyl acetate of 100-0 to 0-100. 1.2 g of expected product is obtained in the form of a yellow solid.

TLC: Rf=0.12 [silica gel, eluent: ethyl acetate (100%)]

1H-NMR (CDCl$_3$): δ 2.10 to 2.20 ppm (m, 4H, N—CH2-CH2-CH—CH2); 3.13 and 4.87 (dt and bd, 4H, CH2-CH2-N—CH2-CH2); 3.30 (m, 1H, CH2-CH—CH2,); 3.72 and 3.91 (2s, 6H, C—OCH$_3$); 7.47 and 8.19 (2d, 2H, C—CH═CH—C(CH)═N); 7.50 (dd, 1H, N—CH═CH—CH═C); 8.22 (dd, 1H, N—CH═CH—CH═C); 9.12 (dd, 1H, N—CH═CH—CH═C).

MS: 386.388 (MH+).

Synthesis of tert-butyl 2-benzyloxycarbonylamino-3-[2,5-dimethoxy-6-(4-[1,8]naphthyridin-2-yl-piperidin-1-yl)-pyrimidin-4-ylamino]-propionate A mixture of 1.2 g (3.1 mmoles) 2-[1-(6-Chloro-2,5-dimethoxy-pyrimidin-4-yl)-piperidin-4-yl]-[1,8]naphthyridine, 1.3 g tert-butyl (4.40 mmoles) of 3-amino-2-benzyloxycarbonylamino propionate, 750 mg (4.95 mmoles) of cesium fluoride, 200 mg (0.217 mmole) of tris(dibenzylideneacetone) dipalladium (0), and 120 mg (0.186 mmole) of 2,2'-bis(diphenyl-phosphino)-1,1'-binaphthyl in 150 ml of dioxane is heated under reflux for 6 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed a first time on alumina eluting with ethyl acetate-ethyl ether 50-50 then a second time on silica with a gradient of heptane-ethyl acetate of 100-0 to 0-100. 900 mg of expected product is obtained in the form of an amorphous yellow solid.

TLC: Rf=0.35 (silica gel, eluent: ethyl acetate).

1H-NMR (CDCl$_3$): δ 1.48 ppm (s, 1H, tBu); 2.12 (m, 4H, N—CH2-CH2-CH—CH2); 3.01 and 4.60 (bt and bd, 4H, CH2-CH2-N—CH2-CH2); 3.21 (m, 1H, CH2-CH—CH2,); 3.57 and 3.88 (2s, 6H, C—OCH$_3$); 3.85 (m, 2H, NH—CH$_2$—CH—NH); 4.41 (m, 1H, NH—CH2-CH—NH); 5.12 (s, 2H, CH$_2$-Ph); 7.35 (m, 5H, CH2Ph); 7.48 and 8.16 (2d, 2H, C—CH═CH—C(CH)═N); 7.48 (dd, 1H, N—CH═CH—CH═C); 8.19 (dd, 1H, N—CH═CH—CH═C); 9.11 (dd, 1H, N—CH═CH—CH═C); 5.37 and 6.29 (bt and bd mobile H's).

MS: 644 (MH+); 454 (MH-COOCH2Ph+).

Synthesis of tert-butyl 2-benzyloxycarbonylamino-3-{2,5-dimethoxy-6-[4-(5,6,7,8-tetrahydro-[1,8]naphthyridin-2-yl)-piperidin-1-yl]-pyrimidin-4-ylamino}-propionate A mixture of 85 mg (1.32 mmoles) of tert-butyl 2-benzyloxycarbonylamino-3-[2,5-dimethoxy-6-(4-[1,8]naphthyridin-2-yl-piperidin-1-yl)-pyrimidin-4-ylamino]-propionate and 30 mg of platinum oxide in 50 ml of ethanol is stirred for 2 hours under hydrogen at atmospheric pressure. The reaction mixture is filtered on Clarcel then evaporated to dryness under reduced pressure (2 kPa). The residue is chromatographed on silica with a gradient of heptane-ethyl acetate-methanol of 100-0-0 to 0-100-0 then 0-95-5. 300 mg of expected product is obtained in the form of a white solid.

TLC: Rf=0.16 (silica gel, eluent: ethyl acetate).

1H-NMR (CDCl$_3$): δ 1.46 ppm (s, 1H, tBu); 1.79 and 1.97 (dt and m, 6H, CH$_2$—CH$_2$—CH$_2$—NH and CH$_2$—CH—CH$_2$); 2.72 (bt, 3H, CH$_2$—CH—CH$_2$ and CH$_2$—CH$_2$—CH$_2$—NH); 2.92 and 4.57 (bt and bd, 4H, CH2-CH2-N—CH2-CH2); 3.43 (m, 2H, CH$_2$—CH$_2$—CH$_2$—NH); 3.56 and 3.87 (2s, 6H, C—OCH$_3$); 3.85 (m masked, 2H, NH—CH$_2$—CH—NH); 4.41 (m, 1H, NH—CH$_2$—CH—NH); 5.12 (s, 2H, CH$_2$-Ph); 6.37 and 7.16 (2d, 2H, C=CH—CH=C); 7.35 (m, 5H, CH2Ph); 5.33 and 6.28 (bt and bd mobile H's).

MS: 648 (MH+); 458 (MH-COOCH2Ph+).

Example 20

Synthesis of 2-benzyloxycarbonylamino-3-{2,5-dimethoxy-6-[4-(5,6,7,8-tetrahydro-[1,8]naphthyridin-2-yl)-piperidin-1-yl]-pyrimidin-4-ylamino}-propionic acid, bis(trifluoroacetate)

350 mg (0.54 mmole) of tert-butyl 2-benzyloxycarbonylamino-3-{2,5-dimethoxy-6-[4-(5,6,7,8-tetrahydro-[1,8] naphthyridin-2-yl)-piperidin-1-yl]-pyrimidin-4-ylamino}-propionate in 10 ml of dichloromethane with 2 ml of trifluoroacetic acid is stirred at ambient temperature until the starting product disappears according to TLC (silica gel, eluent: CH2Cl2-MeOH—H$_2$O—AcOH 90-10-1-1). Toluene is added and the reaction mixture is evaporated to dryness under reduced pressure (2 kPa). The residue is purified by chromatography on silica eluting with an elution gradient of methylene chloride-methanol of 100-0 to 90-10. 360 mg of expected product is obtained in the form of a white solid.

TLC: Rf=0.50 (silica gel, eluent: methylene chloride-methanol-water-acetic acid 90-10-1-1).

1H-NMR (CD$_3$OD): δ1.79 and 1.96 ppm (q and m, 6H, CH$_2$—CH$_2$—CH$_2$—NH and CH$_2$—CH—CH$_2$); 2.82 (bt, 2H, CH$_2$—CH$_2$—CH$_2$—NH); 2.91 (bt, 1H, CH$_2$—CH—CH$_2$); 3.50 and 4.58 (bt and bd, 4H, CH2-CH2-N—CH2-CH2); 3.50 (bt, 2H, CH$_2$—CH$_2$—CH$_2$—NH); 3.67 and 3.87 masked, 2H NH—CH$_2$—CH—NH); 3.52 and 3.85 (2s, 6H, C—OCH$_3$); 4.39 (m, 1H, NH—CH$_2$—CH—NH); 5.07 (bq, 2H, CH$_2$-Ph); 6.62 and 7.58 (2d, 2H, C=CH—CH=C); 7.31 (m, 5H, CH2Ph).

MS: 592 (MH+); 458 (MH-COOCH2Ph+); 590 (MH–); 482 (590-OCH2Ph–); 1182 (2M–).

Example 21

Synthesis of 4-chloro-6-[4-(5,6,7,8-tetrahydro-[1,8] naphthyridin-2-yl)-piperidin-1-yl]-pyrimidine-5-carbaldehyde 80 ml of dimethylacetamide, 3.9 g (22 mmoles) of 4,6-dichloro-5-formyl-pyrimidine [prepared according to Liebigs Annalen der Chemie (1972) 766 73-88] and 8 ml of diisopropylethylamine are added into a single-necked flask containing 3.9 g (17 mmoles) of 7-piperidin-4-yl-1,2,3,4-tetrahydro-[1,8]naphthyridine. This mixture is heated at 120° C. for 3 hours then concentrated to dryness under reduced pressure (2 kPa). The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The crude product obtained is chromatographed on silica gel eluting with a gradient of methylene chloride and ethyl acetate (100-0 to 0-100).

2.3 g of expected product is obtained in the form of a yellow powder.

TLC: Rf=0.25 [silica gel, eluent: ethyl acetate (100%)]

1H-NMR (CDCl$_3$): δ1.79 to 2.06 (m, 6H, NH—CH2-CH2-CH2, N—CH2-CH2-CH—CH2); 2.72 (t, 2H, NH—CH2-CH2-CH2); 2.81 (bt, 1H, CH2-CH—CH2), 3.26 and 4.21 (bt and bd, 4H, CH2-CH2-N—CH2-CH2); 3.43 (bs, 2H, NH—CH2-CH2-CH2); 6.38 and 7.12 (2d, 2H, CH=CH naphthyridine); 8.35 (s, 1H, N=CH—N); 10.34 (s, 1H, C—CH=O).

MS: 358-360 (MH+)

Synthesis of tert-butyl 2-benzyloxycarbonylamino-3-{5-formyl-6-[4-(5,6,7,8-tetrahydro-[1,8]naphthyridin-2-yl)-piperidin-1-yl]-pyrimidin-4-ylamino}-propionate A mixture of 180 mg (0.5 mmole) of 4-chloro-6-[4-(5,6,7, 8-tetrahydro-[1,8]naphthyridin-2-yl)-piperidin-1-yl]-pyrimidine-5-carbaldehyde, 150 mg (0.5 mmole) of tert-butyl 3-amino-2-benzyloxycarbonylamino propionate, 117 mg (0.77 mmole) of cesium fluoride, 23 mg (0.025 mmole) of tris(dibenzylideneacetone) dipalladium (0), and 32 mg (0.51 mmole) of 2,2'-bis(diphenyl-phosphino)-1,1'-binaphthyl in 30 ml of dimethoxyethane is heated under reflux for 2 hours. After cooling down another 23 mg (0.025 mmole) of tris (dibenzylideneacetone) dipalladium (0) is added followed by heating under reflux for 2 hours. The reaction mixture is evaporated to dryness under reduced pressure (2 kPa) and the residue is taken up in ethyl acetate, water and a saturated solution of sodium bicarbonate. The organic phase is separated, dried over magnesium sulphate and the solvent is evaporated off under reduced pressure (2 kPa). The residue is chromatographed on silica gel eluting with a mixture of ethyl acetate-methylene chloride-methanol 50-45-5. 120 mg of expected product is obtained in the form of an amorphous white solid.

TLC: Rf=0.25 (silica gel, eluent: ethyl acetate).

1H-NMR (CDCl$_3$): δ 1.50 (s, 9H, tBu); 1.80 to 2.12 (m, 6H, CH$_2$—CH$_2$—CH$_2$—NH and CH$_2$—CH—CH$_2$); 2.72 (t, 2H, CH$_2$—CH$_2$—CH$_2$—NH); 2.87 (bt, 1H, CH$_2$—CH—CH$_2$); 3.30 and 4.29 (bq and bt, 4H, CH$_2$—CH$_2$—N—CH$_2$—CH$_2$); 3.46 (m, 2H, CH$_2$—CH$_2$—CH$_2$—NH); 3.92 and 4.03 (2m, 2H, NH—CH$_2$—CH—NH); 4.47 (m, 1H, NH—CH$_2$—CH—NH); 5.13 (s, 2H, CH$_2$-Ph); 6.37 and 7.19 (2d, 2H, CH=CH naphthyridine); 7.36 (m, 5H, Ph)); 8.35 (s, 1H, N=CH—N); 9.77 (s, 1H, C—CH=O); 6.17 and 9.16 (bd and bt, 2H, NH).

MS: 616 (MH+); 560 (MH-tBu+); 426 (MH-COOCH2Ph+).

Synthesis of 2-benzyloxycarbonylamino-3-{5-formyl-6-[4-(5,6,7,8-tetrahydro-[1,8]naphthyridin-2-yl)-piperidin-1-yl]-pyrimidin-4-ylamino}-propionic acid bis(trifluoroacetate)

120 mg (0.195 mmole) of tert-butyl 2-benzyloxycarbonylamino-3-{5-formyl-6-[4-(5,6,7,8-tetrahydro-[1,8]naphthyridin-2-yl)-piperidin-1-yl]-pyrimidin-4-ylamino}-propionate in 10 ml of dichloromethane with 1 ml of trifluoroacetic acid is stirred at ambient temperature for 24 hours. Toluene is added and the reaction mixture is evaporated to dryness under reduced pressure (2 kPa). The residue is solubilized in the minimum amount of dichloromethane with a little methanol then poured into diisopropyl ether. The precipitate is filtered. 60 mg of expected product is obtained in the form of a white solid.

TLC: Rf=0.25 (silica gel, eluent: dichloromethane-methanol-water-acetic acid 90-10-1-1)

MS: 560 (MH+); 426 (MH-COOCH2Ph+); 558-(M-H–); 450-(558-OCH2Ph–); 1117-(2M-H–).

Example 22

Synthesis of tert-butyl 2-benzyloxycarbonylamino-3-{5-hydroxymethyl-6-[4-(5,6,7,8-tetrahydro-[1,8]naphthyridin-2-yl)-piperidin-1-yl]-pyrimidin-4-ylamino}-propionate 340 mg (0.55 mmole) of tert-butyl 2-benzyloxycarbonylamino-3-{5-formyl-6-[4-(5,6,7,8-tetrahydro-[1,8]naphthyridin-2-yl)-piperidin-1-yl]-pyrimidin-4-ylamino}-propionate in 50 ml of methanol with 350 mg (9.2 mmoles) of sodium borohydride is stirred at ambient temperature for 2 hours. Then 100 ml of a saturated solution of ammonium chloride is added and the reaction mixture is evaporated to dryness under reduced pressure (2 kPa). The residue obtained is taken up in a mixture of water and ethyl acetate. The organic phase is dried over magnesium sulphate then the solvent is evaporated off under reduced pressure (2 kPa). The crude product obtained is chromatographed on silica gel eluting with a gradient of methylene chloride and ethyl acetate (100-0 to 0-100). 160 mg of expected product is obtained in the form of a yellow oil.

MS: 618 (MH+); 616-(M-H−); 508-(616-OCH2Ph−)

1H-NMR (CDCl$_3$): δ 1.48 (s, 9H, tBu); 1.80 to 2.05 (m, 6H, CH$_2$—CH$_2$—CH$_2$—NH and CH$_2$—CH—CH$_2$); 2.72 (t, 2H, CH$_2$—$\overline{CH_2}$—CH$_2$—NH); 2.87 (bt, 1H, $\overline{CH_2}$—CH—CH$_2$); $\overline{2.99}$ and 3.81 (bt and bd, 4H, CH$_2$—CH$_2$—N—$\overline{CH_2}$—CH$_2$); 3.42 (m, 2H, CH$_2$—CH$_2$—CH$_2$—N$\overline{H}$); 3.90 (m, $\overline{2H}$, NH—CH$_2$—CH—NH); 4.44 (m, $\overline{1H}$, $\overline{NH}$—CH$_2$—CH—NH); 5.09 (s, $\overline{2H}$, CH$_2$-Ph); 6.40 and 7.14 (2d, 2H, CH=CH naphthyridine); $\overline{7.32}$ (m, 5H, Ph)); 8.27 (s, 1H, N=$\overline{CH}$—N); 5.98 and 6.18 (m and bd, 2H, NH).

Synthesis of 2-benzyloxycarbonylamino-3-{5-hydroxymethyl-6-[4-(5,6,7,8-tetrahydro-[1,8]naphthyridin-2-yl)-piperidin-1-yl]-pyrimidin-4-ylamino}-propionic acid, bis(trifluoroacetate)

150 mg (0.24 mmole) of tert-butyl 2-benzyloxycarbonylamino-3-{5-hydroxymethyl-6-[4-(5,6,7,8-tetrahydro-[1,8]naphthyridin-2-yl)-piperidin-1-yl]-pyrimidin-4-ylamino}-propionate in 15 ml of dichloromethane with 0.8 ml of trifluoroacetic acid is stirred at ambient temperature for 24 hours. Toluene is added and the reaction mixture is evaporated to dryness under reduced pressure (2 kPa). The residue is solubilized in the minimum amount of dichloromethane then poured into diisopropyl ether. The precipitate is filtered. 100 mg of expected product is obtained in the form of a white solid.

TLC: Rf=0.40 (silica gel, eluent: dichloromethane-methanol-water-acetic acid 85-15-2-2)

MS: 562 (MH+); 560-(M-H−); 452-(560-OCH2Ph−); 1121-(2M-H−).

Example 23

By operating as described in the preceding examples, using 5-amino-4,6-dichloro-pyrimidine and 2,5-dimethoxytetrahydrofuran, tert-butyl 2-benzyloxycarbonylamino-3-{5-pyrrol-1-yl-6-[4-(5,6,7,8-tetrahydro-[1,8]naphthyridin-2-yl)-piperidin-1-yl]-pyrimidin-4-ylamino}-propionate is prepared TLC: Rf=0.7 (silica gel, eluent: CH2Cl2/MeOH 90:10)

MS: 653 (MH+); 463 (MH-(tBu and CO—O—CH2-C6H5)+ then 2-benzyloxycarbonylamino-3-{5-pyrrol-1-yl-6-[4-(5,6,7,8-tetrahydro-[1,8]naphthyridin-2-yl)-piperidin-1-yl]-pyrimidin-4-ylamino}-propionic acid TLC: Rf=0.5 (silica gel, eluent: CH2Cl2/MeOH 90:10)

MS: 597 (MH+); 463 (MH-(CO—O—CH2-C6H5)+

1H-NMR (MeOD): δ from 1.60 to 2.00 (3m, 6H, H2, H7 and H7'); from 2.70 to 2.85 (m, 3H, H6 and H3); 3.5 $\overline{(m, 2H,}$ H1); $\overline{3.62}$ and 3.92 (2m, 2H, H12); $\overline{4.35}$ (m, $\overline{1H}$, H13); 5.10 $\overline{(m, 2H,}$ —O—CH2-C6H5); $\overline{6.32}$ (m, 2H, H11); $\overline{6.55}$ (d, 1H, H5); 6.67 (m, $\overline{2H}$, H10); from 7.25 $\overline{to}$ 7.40 (m, 5H, —O—CH2-C6H5); 7.55 (d, 1H, H4); 8.12 (m, 1H, H9)

Examples 24 to 37

General Operating Method for the Preparation of the Amines

Stage a 75 mg (0.35 mmoles) of triacetoxysodium borohydride in 6 ml of tetrahydrofuran is left under stirring for 10 minutes at AT. Then a mixture of 100 mg (0.208 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate and 0.228 mmoles of aldehyde in solution in 3 ml of tetrahydrofuran is added. For certain aldehydes the reaction being slower, either the reaction mixture is stirred at ambient temperature for 4 hours, or it is heated under reflux for 4 hours. The reaction mixture is then extracted with ethyl acetate after washing with a saturated solution of sodium bicarbonate. The organic phase obtained is dried over magnesium sulphate before being concentrated to dryness under reduced pressure (2 kPa). The residue is then chromatographed on silica gel with the following eluent: ethyl acetate-dichloromethane/methanol (90/10) 50-50. A mass $m_y$ of expected product is obtained.

TLC: Rf (eluent: dichloromethane-methanol (90/10)-ethyl acetate 50-50.

Stage b

A mass $m_y$ of tert-butyl 3-{5-ethyl-6-[4-(5,6,7,8-tetrahydro-[1,8]naphthyridin-2-yl)-piperidin-1-yl]-pyrimidin-4-ylamino}-2-alkylamino-propionate in 5 ml of dichloromethane with 850 μl of trifluoroacetic acid is stirred at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in a minimum amount of dichloromethane then poured into diisopropyl ether. The precipitate is filtered. A mass $m_z$ of the expected acid is obtained.

TLC: Rf (eluent: dichloromethane-methanol-water-acetic acid 90-10-1-1).

Example 24

Stage a

Synthesis of tert-butyl 2-(2-ethyl-butylamino)-3-{5-ethyl-6-[4-(5,6,7,8-tetrahydro-[1,8]naphthyridin-2-yl)-piperidin-1-yl]-pyrimidin-4-ylamino}-propionate 75 mg (0.35 mmoles) of sodium triacetoxyborohydride in 6 ml of tetrahydrofuran is left under stirring for 10 minutes at TA. Then a mixture of 100 mg (0.208 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate and 0.228 mmoles of 2-ethyl-butylaldehyde in solution in 3 ml of tetrahydrofuran is added. The reaction mixture is stirred at ambient temperature for 4 hours 30 minutes. Then it is extracted with ethyl acetate after washing with a saturated solution of sodium bicarbonate. The organic phase obtained is dried over magnesium sulphate before being concentrated to dryness under reduced pressure (2 kPa). The residue is then chromatographed on silica gel with the following eluent: ethyl acetate-dichloromethane/methanol (80/20) 50-50. A mass $m_y$ of expected product is obtained.

TLC: Rf=0.27 (eluent: dichloromethane-methanol (80/20)-ethyl acetate 50-50).

1H-NMR (CDCl₃): δ 0.9 (t, 6H, CH3-CH2-CH—CH2-CH3); 1.2 (t, 3H, CH2-CH3); 1.47 (s, 9H, tBu); 1.7 (m, 1H, ((CH2CH3)₂—CH—CH2); 1.85 and 2.05 (2m, 6H, N—CH2-CH2-CH—CH2-CH2, CH2-CH2-CH2-NH); 2.4 and 2.53 (m, 3H, N—CH2-CH2-CH—CH2-CH2, (CH2CH3)₂—CH—CH2-NH); 2.6 and 2.75 (m, 4H, CH2-CH2-CH2-NH, CH2-CH3); 2.96 and 3.56 (2m, 4H, N—CH2-CH2-CH—CH2-CH2); 3.32 (m, 1H, NH—CH2-CH—NH); 3.45 (m, 2H, CH2-CH2-CH2-NH); 3.7 and 3.9 (m, 2H, NH—CH2-CH—NH); 5.42 (t, 1H, mobile NH); 6.43 and 7.17 (2d, 2H, CH=CH naphthyridine); 8.32 (s, 1H, N=CH—N).

MS: 566 (MH+), 510 (MH-tBu).

Stage b

Synthesis of 2-(2-ethyl-butylamino)-3-{5-ethyl-6-[4-(5,6,7,8-tetrahydro-[1,8]naphthyridin-2-yl)-piperidin-1-yl]-pyrimidin-4-ylamino}-propionic acid, bis(trifluoroacetate)

80 mg (0.141 mmoles) of (1,1-dimethylethyl) 3-[[5-ethyl-6-[4-(1,2,3,4-tetrahydro-1,8-naphthyridin-7-yl)-1-piperidinyl]-4-pyrimidinyl]amino]-N-(4-methoxy-benzoyl) alaninate in 5 ml of dichloromethane with 400 μl of trifluoroacetic acid is stirred at ambient temperature for 9 hours.

Then toluene is added and the reaction mixture is evaporated to dryness under reduced pressure (2 kPa). The residue is solubilized in the minimum amount of dichloromethane, then poured into diisopropyl ether. The precipitate is filtered. 90 mg of expected product is obtained.

TLC: Rf=0.50 (silica gel, eluent: dichloromethane-methanol-water-acetic acid 70-30-6-3).

1H-NMR (CDCl₃): δ 0.9 (t, 6H, CH3-CH2-CH—CH2-CH3); 1.2 (t, 3H, CH2-CH3); 1.8 (m, 1H, ((CH2CH3)₂-CH—CH2), 1.85 and 2.1 (2m, 6H, N—CH2-CH2-CH—CH2-CH2, CH2-CH2-CH2-NH); 2.56 (q, 2H, CH2-CH3); 2.78 (t, 2H, CH2-CH2-CH2-NH); 2.9 and 3.1 (m, 3H, (CH2CH3)₂—CH—CH2-NH, N—CH2-CH2-CH—CH2-CH2); 3.28 and 3.9 (2m, 4H, N—CH2-CH2-CH—CH2-CH2); 3.53 (m, 2H, CH2-CH2-CH2-NH); 4.25 (m, 2H, NH—CH2-CH—NH); 6.4 and 7.38 (2d, 2H, CH=CH naphthyridine); 8.33 (s, 1H, N=CH—N); 10.05 (m, 1H, mobile COOH).

MS: 510 (MH+).

$M_x$: mass of aldehyde introduced
$M_y$: mass of ester obtained.
$M_z$: mass of acid obtained.

| Example | Acid obtained | FW (Free base) | FW (Free base + 2 TFA) | Mz (mg) |
|---|---|---|---|---|
| 25 | | 543.72 | 771.72 | 90 |
| 26 | | 516.65 | 744.65 | 25 |
| 27 | | 591.76 | 819.76 | 30 |

-continued
| Example | Acid obtained | FW (Free base) | FW (Free base + 2 TFA) | Mz (mg) |
|---|---|---|---|---|
| 28 | 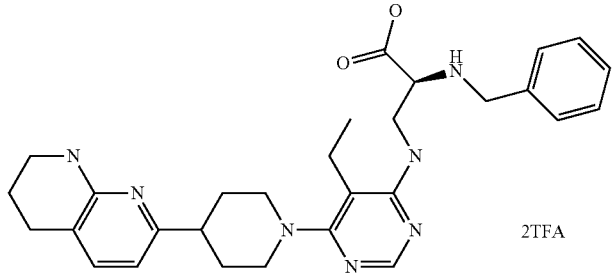 [SMILES: CCc1c(NC[C@H](NCc2ccccc2)C(=O)O)ncnc1N1CCC(c2ccc3c(n2)NCCC3)CC1] 2TFA | 571.77 | 799.77 | 35 |
| 29 | 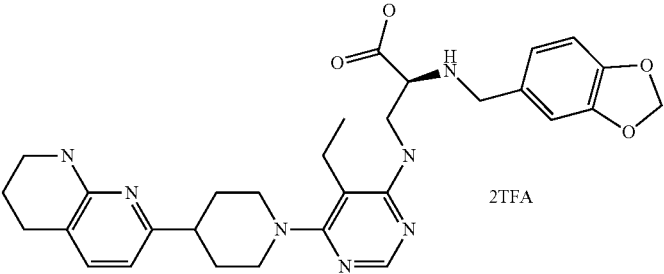 [SMILES: CCc1c(NC[C@H](NCc2ccc3c(c2)OCO3)C(=O)O)ncnc1N1CCC(c2ccc3c(n2)NCCC3)CC1] 2TFA | 559.67 | 787.67 | 46 |
| 30 | 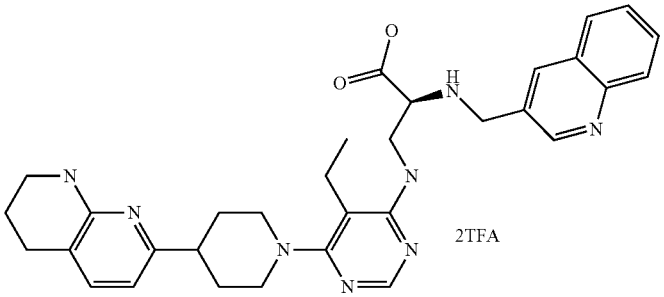 [SMILES: CCc1c(NC[C@H](NCc2cnc3ccccc3c2)C(=O)O)ncnc1N1CCC(c2ccc3c(n2)NCCC3)CC1] 2TFA | 566.71 | 794.71 | 34 |
| 31 | 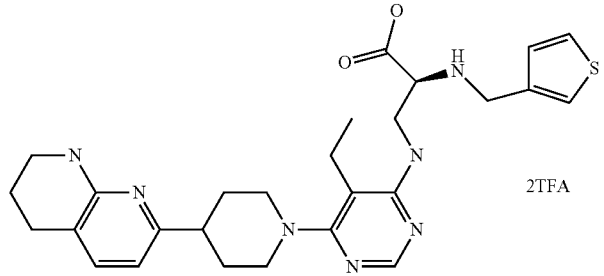 [SMILES: CCc1c(NC[C@H](NCc2ccsc2)C(=O)O)ncnc1N1CCC(c2ccc3c(n2)NCCC3)CC1] 2TFA | 521.69 | 749.69 | 14 |
| 32 | 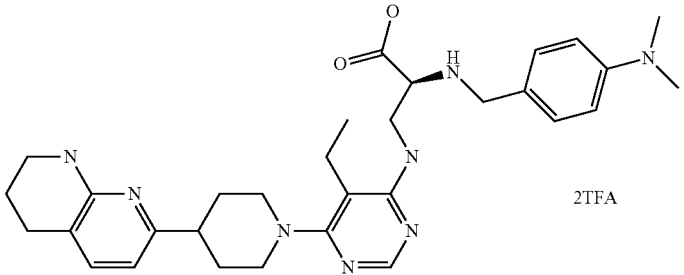 [SMILES: CCc1c(NC[C@H](NCc2ccc(N(C)C)cc2)C(=O)O)ncnc1N1CCC(c2ccc3c(n2)NCCC3)CC1] 2TFA | 558.73 | 786.73 | 38 |

-continued
| Example | Acid obtained | FW (Free base) | FW (Free base + 2 TFA) | Mz (mg) |
|---|---|---|---|---|
| 33 | 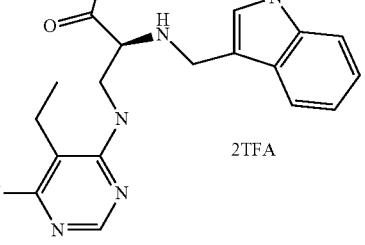 2TFA | 554.70 | 782.70 | 13 |
| 34 | 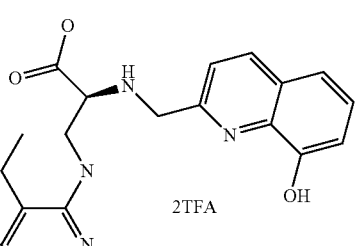 2TFA | 582.71 | 810.71 | 14 |
| 35 | 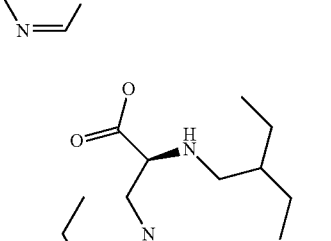 2TFA | 509.70 | 737.70 | 90 |
| 36 | 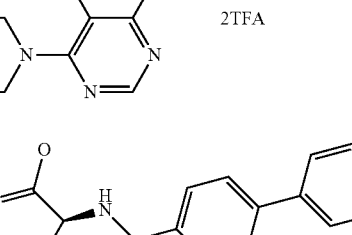 2TFA | 592.75 | 820.75 | 10 |
| 37 |  2TFA | 646.80 | 876.80 | 40 |

The products obtained above are prepared from the following raw materials:

| Example | Aldhyde | FW | Mx (mg) | expected product |
|---|---|---|---|---|
| 25 | 3-phenylpropanal | 138.18 | 28 | |
| 26 | pyridine-3-carbaldehyde | 107.11 | 25 | |
| 27 | biphenyl-4-carbaldehyde | 182.22 | 42 | |
| 28 | benzaldehyde | 106.12 | 24 | |

| | | | |
|---|---|---|---|
| 29 | 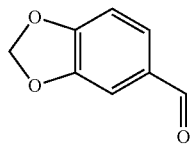 [SMILES: O=Cc1ccc2c(c1)OCO2] | 150.13 | 34 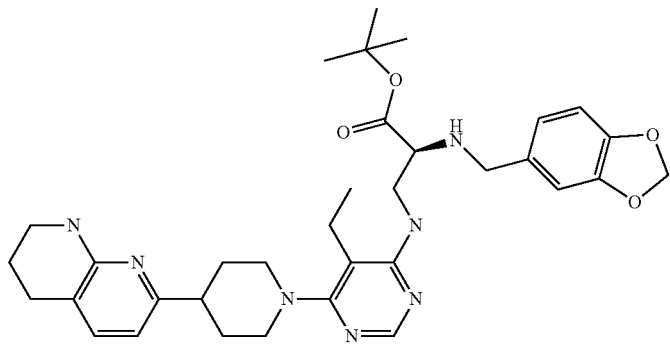 [SMILES: CCc1c(NC[C@H](NCc2ccc3c(c2)OCO3)C(=O)OC(C)(C)C)ncnc1N1CCC(c2ccc3c(n2)NCCC3)CC1] |
| 30 | 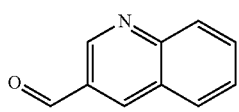 [SMILES: O=Cc1cnc2ccccc2c1] | 157.17 | 36 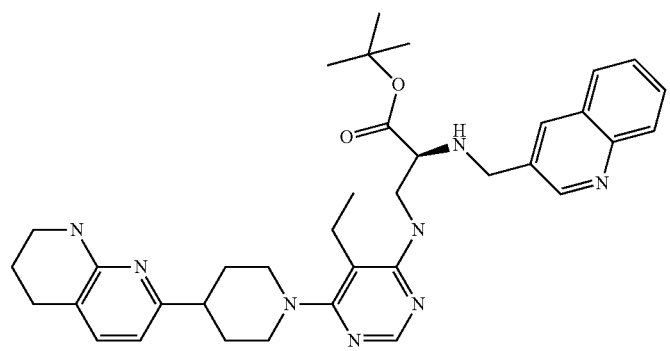 [SMILES: CCc1c(NC[C@H](NCc2cnc3ccccc3c2)C(=O)OC(C)(C)C)ncnc1N1CCC(c2ccc3c(n2)NCCC3)CC1] |
| 31 | 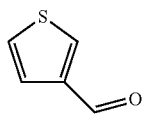 | 112.15 | 26 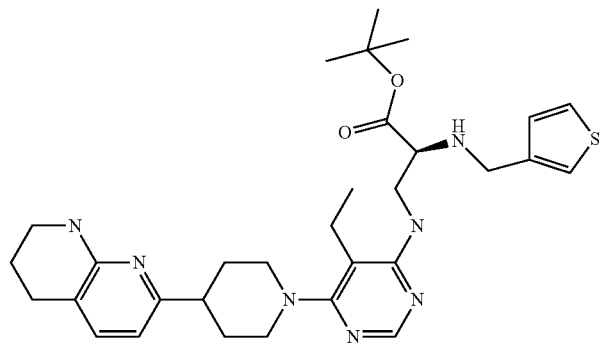 [SMILES: CCc1c(NC[C@H](NCc2ccsc2)C(=O)OC(C)(C)C)ncnc1N1CCC(c2ccc3c(n2)NCCC3)CC1] |
| 34 | 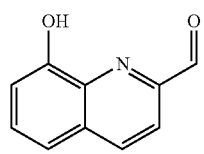 [SMILES: O=Cc1ccc2cccc(O)c2n1] | 173.17 | 40 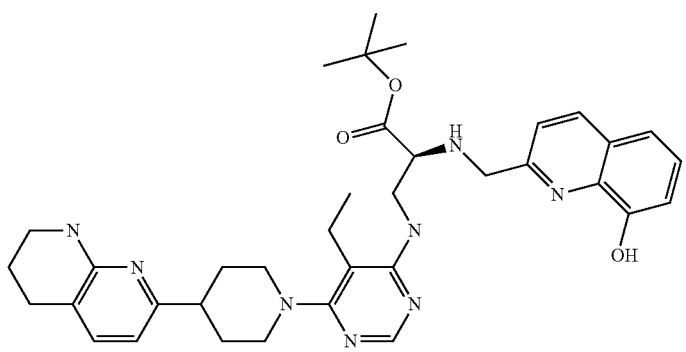 [SMILES: CCc1c(NC[C@H](NCc2ccc3cccc(O)c3n2)C(=O)OC(C)(C)C)ncnc1N1CCC(c2ccc3c(n2)NCCC3)CC1] |

-continued

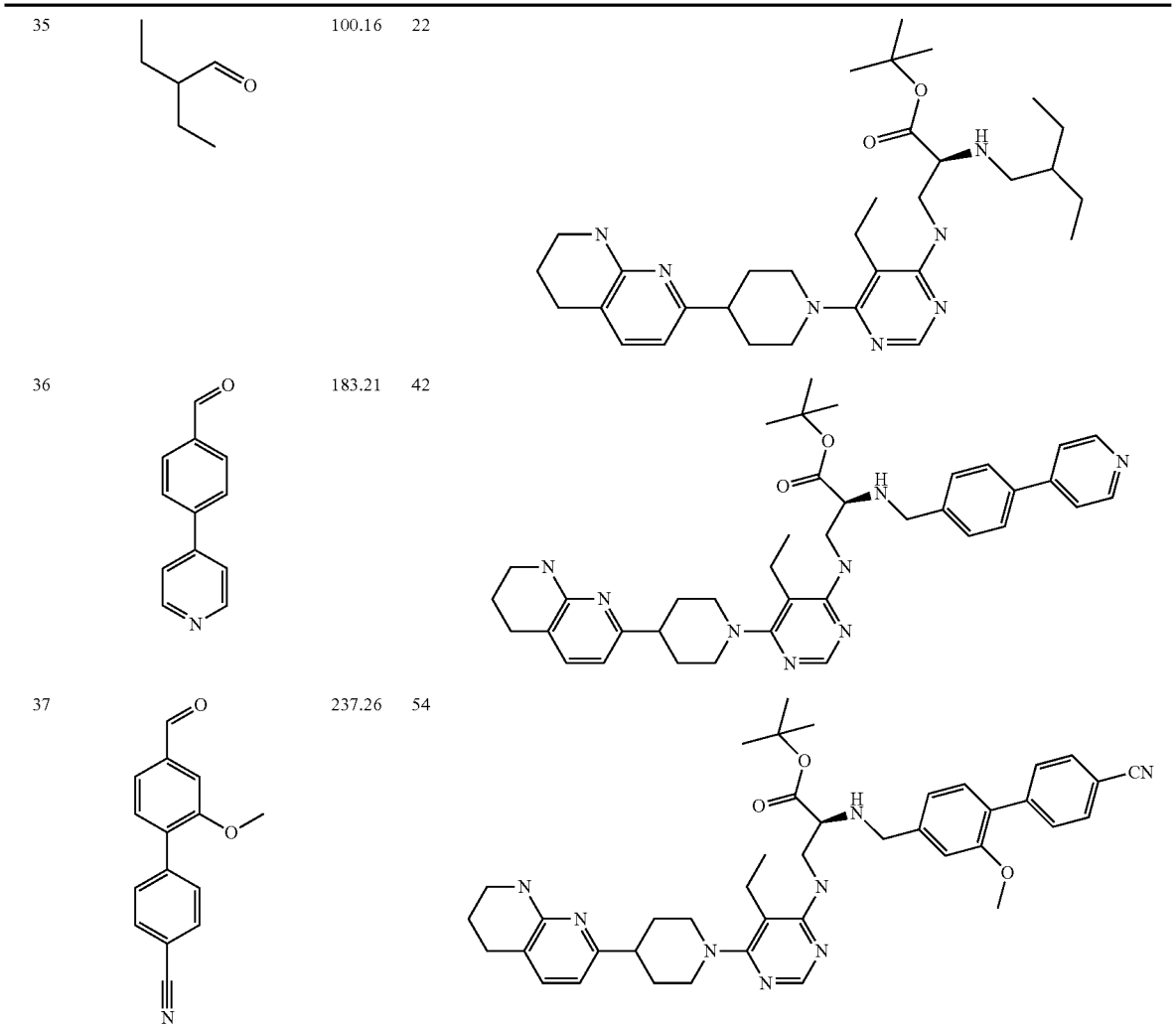

| Example | FW | M<sub>y</sub> (mg) | Yield |
|---------|--------|------|----|
| 25 | 599.83 | 100 | 94 |
| 26 | 572.76 | 37 | 31 |
| 27 | 647.87 | 20 | 15 |
| 28 | 571.77 | 36 | 30 |
| 29 | 615.78 | 40 | 31 |
| 30 | 622.82 | 79 | 61 |
| 31 | 577.8 | 26 | 21 |
| 34 | 638.82 | 30 | 23 |
| 35 | 565.81 | 89 | 38 |
| 36 | 648.86 | 32 | 24 |
| 37 | 702.91 | 42 | 29 |

Example 38

Synthesis of tert-butyl 3-[5-methyl-6-[4-(5,6,7,8-tetrahydro-(1,8)naphthyridin-2-yl)-piperidin-1-yl]-pyrimidin-4-ylamino]-2-(4-methoxy benzoyl)-propionate 40 mg (0.233 mmoles) of 4-methoxy-benzoyl chloride in solution in 3 ml of dichloromethane is added to a mixture of 109 mg (0.233 mmoles) of tert-butyl 2-amino-3-{5-methyl-6-[4-(5,6,7,8-tetrahydro-[1,8]naphthyridin-2-yl)-piperidin-1-yl]-pyrimidin-4-ylamino}-propionate in solution in 6 ml of dichloromethane and 650 μl of pyridine. The reaction mixture is stirred at ambient temperature for 1 hour. Then, the solvent is evaporated off under reduced pressure (2 kPa) and the residue is chromatographed on silica gel with the following eluent: ethyl acetate-dichloromethane 50-50, ethyl acetate-dichloromethane/methanol (95/5) 50-50 then finishing with ethyl acetate-dichloromethane/methanol (9/1) 50-50. 98 mg of expected product is obtained.

TLC: Rf=0.62 (silica gel, eluent: dichloromethane-methanol-water-acetic acid 85-15-2-2)

1H-NMR (CDCl$_3$): δ 1.54 ppm (s, 9H, tBu); 1.20 (t, 3H, CH$_3$); 1.78 to 2.05 (m, 6H, CH$_2$—CH—CH$_2$ and CH$_2$—$\overline{CH_2}$—CH$_2$—NH); 2.66 (tt, 1$\overline{H, CH_2}$—CH$\overline{=CH_2}$); 2.72 (t, $\overline{2H, CH_2}$—CH$_2$—CH$_2$—NH); 2.92 and $\overline{3.68}$ (bq and m, 4H, CH$_2$—CH$_2$—N—CH$_2$—CH$_2$); 3.42 (m, 2H, CH$_2$—CH$_2$—CH$_2$—NH); 3.86 (s, 3H, COCH$_3$); 3.97 (t, 2H, NH—CH$_2$—CH—NH); 4.78 (q, 1H, NH—CH$_2$—CH—NH); 5.17 (t, 1H, 1H, NH—CH$_2$—CH—NH); 6.41 and 7.13 (2d, 2H, H naphthyridine); 6.92 and 7.79 (2d, 4H, H benzoyl); 8.32 ppm (s, 1H, N=CH—N); 8.23 (mobile H).

MS: 602 (MH+); 412 (MH-COOCH2Ph+).

Synthesis of 3-[5-methyl-6-[4-(5,6,7,8-tetrahydro-(1,8) naphthyridin-2-yl)-piperidin-1-yl]-pyrimidin-4-ylamino]-2-(4-methoxy benzoyl)-propionic acid, bis(trifluoroacetate)

20 mg (0.033 mmole) of tert-butyl 3-[5-methyl-6-[4-(5,6,7,8-tetrahydro-(1,8)naphthyridin-2-yl)-piperidin-1-yl]-pyrimidin-4-ylamino]-2-(4-methoxy benzoyl)-propionate in 2 ml of dichloromethane with 0.3 ml of trifluoroacetic acid is stirred at ambient temperature for 3 hours. Toluene is added and the reaction mixture is evaporated to dryness under reduced pressure (2 kPa). The residue is solubilized in the minimum amount of dichloromethane then poured into diisopropyl ether. The precipitate is filtered. 20 mg of expected product is obtained in the form of a beige solid.

1H-NMR (CDCl$_3$): δ 1.77 to 2.15 (m, 6H, CH$_2$—CH—CH$_2$ and CH$_2$—CH$_2$—CH$_2$—NH); 2.37 (s, 3H, CCH$_3$); 2.77 (bt, 2H, CH$_2$—CH$_2$—CH$_2$—NH); 2.99 (bt, 1H, CH$_2$—CH—CH$_2$); 3.22 and 3.97 (bt and bd, 4H, CH$_2$—CH$_2$—N—CH$_2$—CH$_2$); 3.52 (m, 2H, CH$_2$—CH$_2$—CH$_2$—NH); 3.91 and 4.14 (2m, 2H, NH—CH$_2$—CH—NH); 4.82 (m, 1H, NH—CH$_2$—CH—NH); 6.89 and 7.82 (2d, 2H, H naphthyridine); 7.19 and 7.38 (2d, 4H, H benzoyl); 8.25 ppm (s, 1H, N=CH—N); 6.39; 7.72; 8.09 and 9.61 mobile H's.

MS: 546 (MH+)

Examples 39 to 51

General Operating Method for the Preparation of the Amides

Stage a

650 µl of pyridine is added to 112.5 mg (0.23 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate in solution in 6 ml of dichloromethane, after stirring for 15 minutes at AT, 0.23 mmoles (mass m$_x$) of acid chloride in solution in 3 ml of dichloromethane is added. The reaction mixture is stirred at ambient temperature for 1 to 3 hours depending to the acid chloride used. Then, the solvent is evaporated off under reduced pressure (2 kPa) and the residue is chromatographed on silica gel with the following eluent: ethyl acetate-dichloromethane 50-50, ethyl acetate-dichloromethane/methanol (95/5) 50-50 and finishing with ethyl acetate-dichloromethane/methanol (90-10) 50-50. A mass m$_y$ of expected product is obtained.

TLC: Rf (eluent: dichloromethane-methanol (90/10)-ethyl acetate 50-50).

Stage b

A mass m$_y$ of the tert-butyl ester of Stage a) in 5 ml of dichloromethane with 850 µl of trifluoroacetic acid is stirred at ambient temperature until the starting product disappears according to TLC (silica gel, eluent: CH2Cl2-MeOH—H2O—AcOH 90-10--1-1). Toluene is added and the reaction mixture is evaporated to dryness under reduced pressure (2 kPa). The residue is solubilized in the minimum amount of dichloromethane then poured into diisopropyl ether. The precipitate is filtered. A mass m$_z$ is obtained of bis trifluoroacetate of the expected acid.

TLC: Rf (eluent: dichloromethane-methanol-water-acetic acid 90-10-1-1

Example 39

Stage a

Synthesis of tert-butyl 3-[5-ethyl-6-[4-(5,6,7,8-tetrahydro-(1,8)naphthyridin-2-yl)-piperidin-1-yl]-pyrimidin-4-ylamino]-2-(4-methoxy benzoyl)-propionate 40 mg (0.233 mmoles) of 4-methoxy-benzoyl chloride in solution in 3 ml of dichloromethane is added to a mixture of 112.5 mg (0.233 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate in solution in 6 ml of dichloromethane and 650 µl of pyridine. The reaction mixture is stirred at ambient temperature for 1 hour. Then, the solvent is evaporated off under reduced pressure (2 kPa) and the residue is chromatographed on silica gel with the following eluent: ethyl acetate-dichloromethane (50-50), ethyl acetate-dichloromethane/methanol (95/5) 50-50 then finishing with ethyl acetate-dichloromethane/methanol (9/1) 50-50. 98 mg of expected product is obtained.

TLC: Rf=0.62 (silica gel, eluent: dichloromethane-methanol-water-acetic acid 85-15-2-2)

1H-NMR (CDCl$_3$): δ 1.13 (t, 3H, CH2-CH3); 1.42 (s, 9H, tBu); 1.73 and 1.93 (2m, 6H, N—CH2-CH2-CH—CH2-CH2, CH2-CH2-CH2-NH); 2.41 (q, 2H, CH2-CH3); 2.62 (m, 3H, CH2-CH2-CH2-NH, N—CH2-CH2-CH—CH2-CH2); 3.90 and 3.53 (2m, 4H, N—CH2-CH2-CH—CH2-CH2); 3.35 (m, 2H, CH2-CH2-CH2-NH); 3.78 (s, 3H, O—CH3); 3.85 (m, 2H, NH—CH2—CH—); 4.71 (m, 1H, NH—CH2-CH—NH); 5.20 (t, 1H, NH mobile) 7.07 and 8.12 (2d, 2H, CH=CH naphthyridine); 6.85 and 7.72 (2d, 4H, CH=CH phenyl); 8.25 (s, 1H, N=CH—N).

MS: 616 (MH+), 560 (MH-tbu).

Stage b

Synthesis of 3-[5-ethyl-6-[4-(5,6,7,8-tetrahydro-(1,8) naphthyridin-2-yl)-piperidin-1-yl]-pyrimidin-4-ylamino]-2-(4-methoxy benzoyl)-propionic acid, bis(trifluoroacetate)

90 mg (0.146 mmoles) of tert-butyl 3-[5-ethyl-6-[4-(5,6,7,8-tetrahydro-(1,8)naphthyridin-2-yl)-piperidin-1-yl]-pyrimidin-4-ylamino]-2-(4-methoxy benzoyl)-propionate in 5 ml of dichloromethane with 850 µl of trifluoroacetic acid is stirred at ambient temperature for 7 hours.

Then toluene is added and the reaction mixture is evaporated to dryness under reduced pressure (2 kPa). The residue is solubilized in the minimum amount of dichloromethane then poured into diisopropyl ether. The precipitate is filtered. 85 mg of expected product is obtained.

TLC: Rf=0.27 (silica gel, eluent: dichloromethane-methanol-water-acetic acid 90-10-1-1).

1H-NMR (CDCl$_3$): δ 1.17 (t, 3H, CH2-CH3); 1.82 and 2.05 (2m, 6H, N—CH2-CH2-CH—CH2-CH2, CH2-CH2-CH2-NH); 2.53 (q, 2H, CH2-CH3); 2.77 (t, 2H, CH2-CH2-CH2-NH); 2.98 (m, 1H, N—CH—CH2-CH2); 3.25 and 3.90 (2m, 4H, N—CH2-CH2-CH—CH2-CH2); 3.52 (m, 2H, CH2-CH2-

CH2-NH); 3.82 (s, 3H, O—CH3); 4.20 (m, 2H, NH—CH2-CH—) 4.85 (m, 1H, NH—CH2-CH—NH); 6.40 and 7.75 (2m, 1H, NH mobile) 7.37 and 8.17 (2d, 2H, CH═CH naphthiridine); 6.90 and 8.85 (2d, 4H, CH═CH phenyl); 8.32 (s, 1H, N═CH—N).
MS: 560 (MH+).
$M_x$: mass of acid chloride introduced.
$M_y$: mass of ester obtained.
$M_z$: mass of acid obtained.
| Example | Acid obtained | FW (Free base) | FW (Free base + 2TFA) | Mz (mg) | MS (MH+) |
|---|---|---|---|---|---|
| 39 | 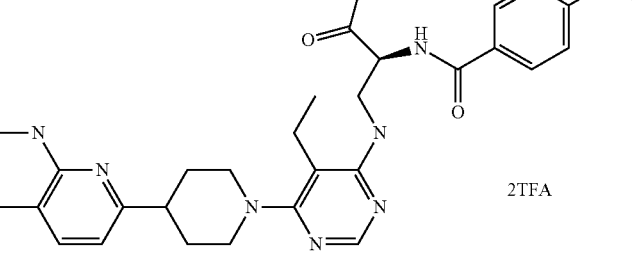 2TFA | 559.67 | 787.67 | 85 | 560 |
| 40 | 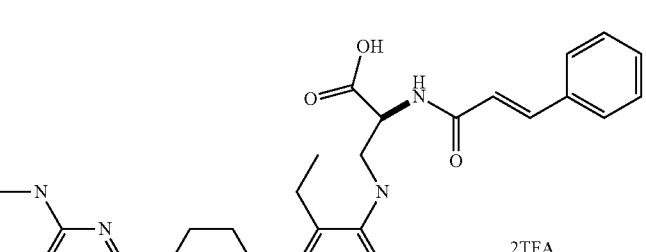 2TFA | 555.69 | 783.69 | 50 | 556 |
| 41 | 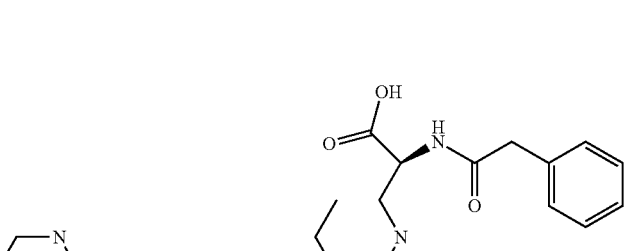 2TFA | 543.67 | 771.67 | 62 | 544 |
| 42 | 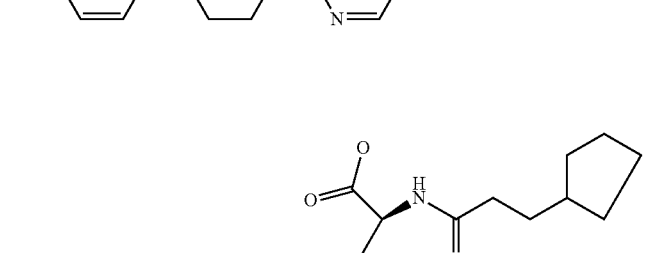 2TFA | 549.72 | 777.72 | 70 | 550 |

| Example | Acid obtained | FW (Free base) | FW (Free base + 2TFA) | Mz (mg) | MS (MH+) |
|---|---|---|---|---|---|
| 43 | 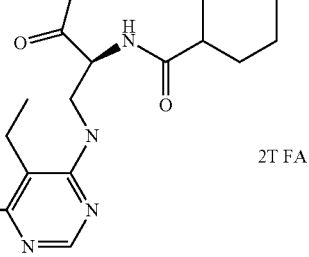 2TFA | 535.70 | 763.7 | 66 | 536 |
| 44 | 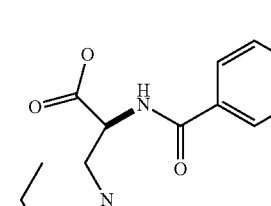 2TFA | 529.65 | 757.65 | 84 | 530 |
| 45 | 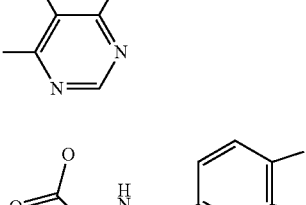 2TFA | 573.66 | 801.66 | 89 | 574 |
| 46 | 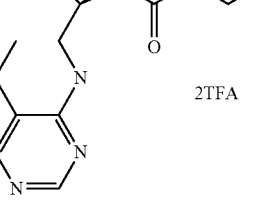 2TFA | 579.71 | 807.71 | 95 | 580 |
| 47 | 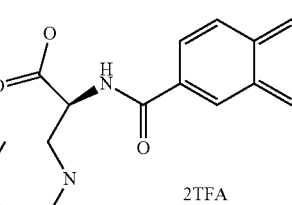 2TFA | 597.64 | 825.64 | 64 | 598 |

-continued
| Example | Acid obtained | FW (Free base) | FW (Free base + 2TFA) | Mz (mg) | MS (MH+) |
|---|---|---|---|---|---|
| 48 | 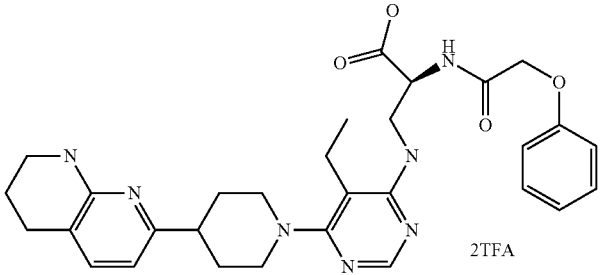 [SMILES: CCc1c(NC[C@H](NC(=O)COc2ccccc2)C(=O)O)ncnc1N1CCC(c2ccc3c(n2)NCCC3)CC1] | 559.67 | 787.67 | 80 | 560 |
| 49 | 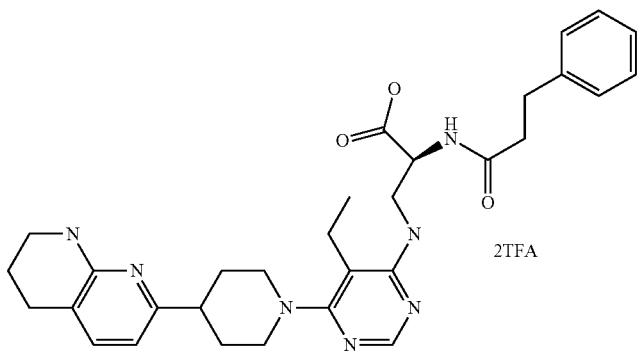 [SMILES: CCc1c(NC[C@H](NC(=O)CCc2ccccc2)C(=O)O)ncnc1N1CCC(c2ccc3c(n2)NCCC3)CC1] | 557.70 | 785.7 | 75 | 558 |
| 50 | 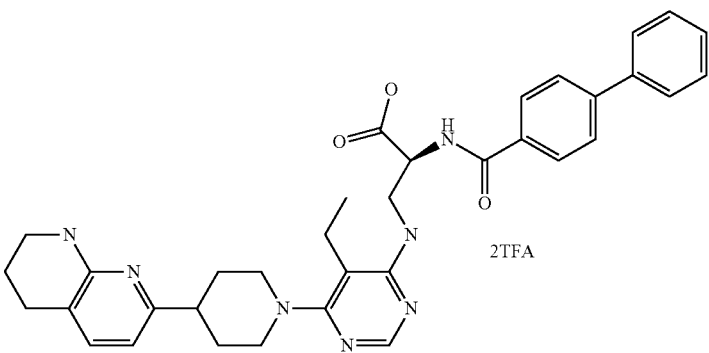 [SMILES: CCc1c(NC[C@H](NC(=O)c2ccc(-c3ccccc3)cc2)C(=O)O)ncnc1N1CCC(c2ccc3c(n2)NCCC3)CC1] | 605.75 | 833.75 | 123 | 605 |
| 51 | 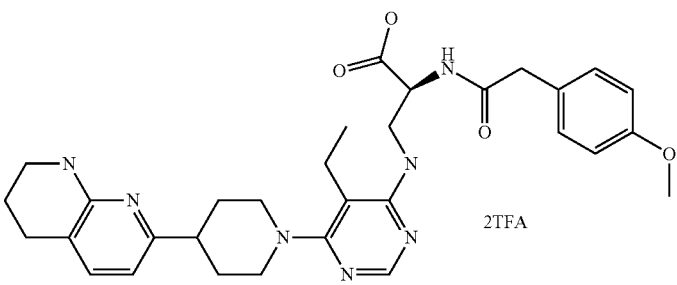 [SMILES: CCc1c(NC[C@H](NC(=O)Cc2ccc(OC)cc2)C(=O)O)ncnc1N1CCC(c2ccc3c(n2)NCCC3)CC1] | 573.70 | 801.7 | 155 | 574 |

The products obtained above are prepared from the following raw materials:

| Example | Acid chloride | mx (mg) | ester formed |
| --- | --- | --- | --- |
| 39 | 4-methoxybenzoyl chloride | 40 | |
| 40 | cinnamoyl chloride | 30 | |
| 41 | phenylacetyl chloride | 36.2 | |
| 42 | 3-cyclopentylpropanoyl chloride | 37.4 | |

-continued
| | | | |
|---|---|---|---|
| 43 | 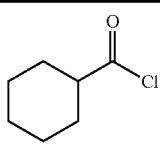 | 34.2 | 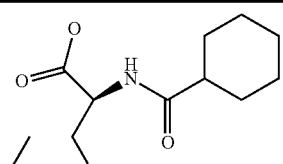 |
| 44 | 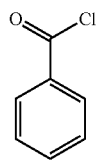 | 33 | 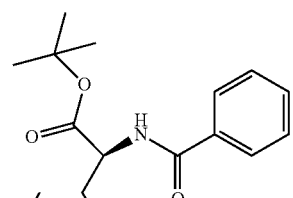 |
| 45 | 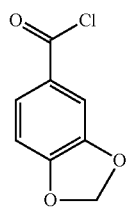 | 43 | 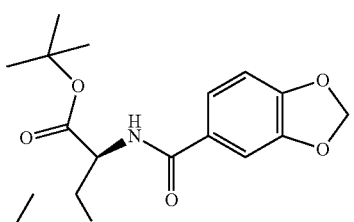 |
| 46 | 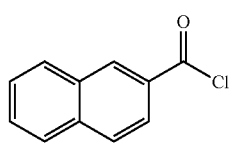 [SMILES: O=C(Cl)c1ccc2ccccc2c1] | 44.5 | 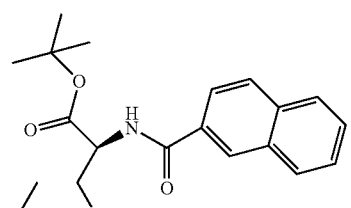 |
| 47 | 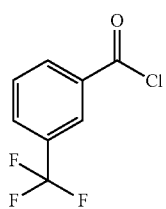 [SMILES: O=C(Cl)c1cccc(C(F)(F)F)c1] | 48.7 | 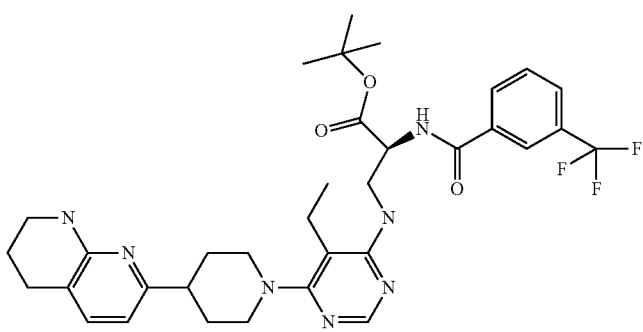 [SMILES: CCc1c(NC[C@H](NC(=O)c2cccc(C(F)(F)F)c2)C(=O)OC(C)(C)C)ncnc1N1CCC(c2ccc3c(n2)NCCC3)CC1] |

-continued
| | | | | | | |
|---|---|---|---|---|---|---|
| 48 | 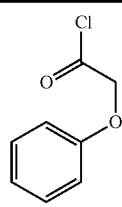 | 40 | 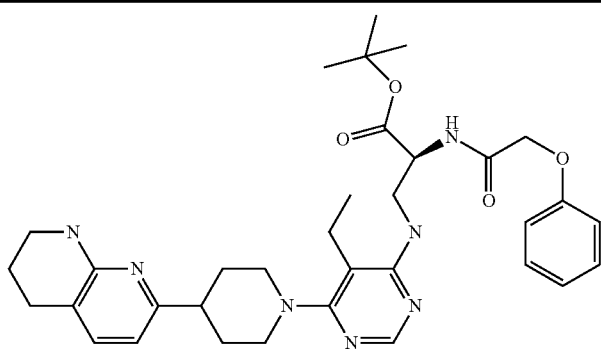 | | | |
| 49 | 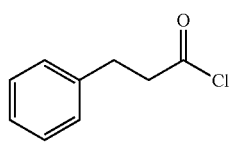 [SMILES: O=C(Cl)CCc1ccccc1] | 39.4 | 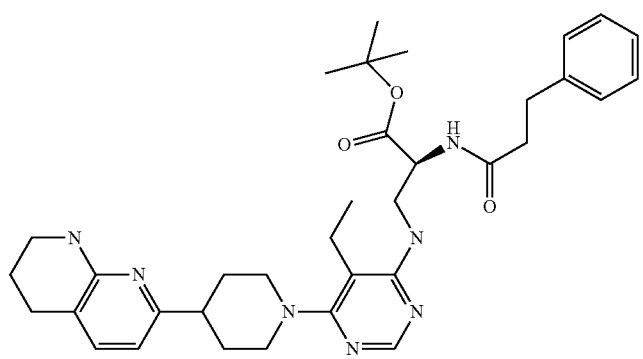 [SMILES: CCc1c(NC[C@H](NC(=O)CCc2ccccc2)C(=O)OC(C)(C)C)ncnc1N1CCC(c2ccc3c(n2)NCCC3)CC1] | | | |
| 50 | 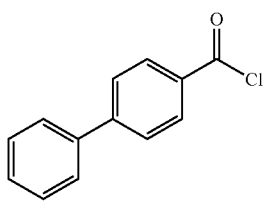 [SMILES: O=C(Cl)c1ccc(-c2ccccc2)cc1] | 46 | 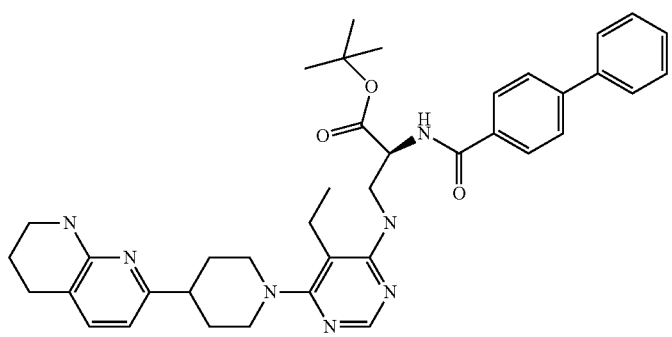 [SMILES: CCc1c(NC[C@H](NC(=O)c2ccc(-c3ccccc3)cc2)C(=O)OC(C)(C)C)ncnc1N1CCC(c2ccc3c(n2)NCCC3)CC1] | | | |
| 51 | 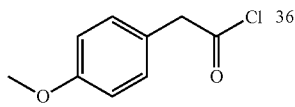 | 36 | 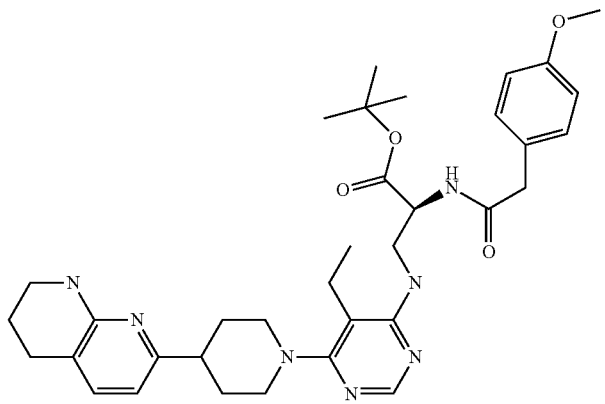 [SMILES: CCc1c(NC[C@H](NC(=O)Cc2ccc(OC)cc2)C(=O)OC(C)(C)C)ncnc1N1CCC(c2ccc3c(n2)NCCC3)CC1] | | | |
| | | Example | FW | M_y (mg) | Yield | MS (MH+) | Rf |
| | | 39 | 615.78 | 98 | 68 | 616 | 0.53 |
| | | 40 | 611.79 | 50 | 46 | 612 | |
| | | 41 | 599.78 | 81 | 58 | 600 | 0.50 |
| | | 42 | 605.83 | 81 | 57 | 606 | 0.53 |
| | | 43 | 591.8 | 74 | 53.5 | 592 | 0.53 |
| | | 44 | 585.76 | 86 | 63 | 586 | 0.47 |
| | | 45 | 629.77 | 92 | 62.5 | 630 | 0.50 |

| 46 | 635.82 | 94 | 63 | 636 | 0.53 |
| 47 | 653.75 | 94 | 61.5 | 654 | 0.53 |
| 48 | 615.78 | 92 | 64 | 616 | 0.58 |
| 49 | 613.81 | 85 | 59 | 614 | 0.58 |
| 50 | 661.85 | 63 | 38 | 662 | 0.20 |
| 51 | 629.81 | 90 | 57 | 630 | 0.16 |

Example 52

Synthesis of tert-butyl 3-[5-ethyl-6-[4-(5,6,7,8-tetrahydro-(1,8)naphthyridin-2-yl)-piperidin-1-yl]-pyrimidin-4-ylamino]-2-[3-(2-nitrophenyl)-ureido]-propionate A mixture of 240 mg (0.50 mmole) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate and 82 mg (0.50 mmole) of 2-nitrophenylisocynate in 15 ml of tetrahydrofuran is stirred for 3 hours at ambient temperature. The reaction mixture is evaporated to dryness under reduced pressure (2 kPa) and the residue is taken up in ethyl acetate and water. The organic phase is separated, dried over magnesium sulphate and the solvent evaporated off under reduced pressure (2 kPa). The residue is chromatographed on alumina eluting with a gradient of ethyl acetate-methylene chloride-methanol from 50-50-0 to 50-50-10. 260 mg of expected product is obtained in the form of a yellow solid.

TLC: Rf=0.12 (silica gel, eluent: ethyl acetate-methylene chloride-methanol 50-47-3).

1H-NMR (CDCl$_3$): δ 1.20 (t, 3H, CH$_2$CH$_3$); 1.45 (s, 9H, tBu); 1.80 to 2.02 (m, 6H, CH$_2$—CH—CH$_2$ and CH$_2$—CH$_2$—CH$_2$—NH); 2.50 (q, 2H, CH$_2$—CH$_3$); 2.66 (bt, 1H, CH$_2$—CH—CH$_2$); 2.73 (t, 2H, CH$_2$—CH$_2$—CH$_2$—NH); 2.97 and 3.62 (bt and m, 4H, CH$_2$—CH$_2$—N—CH$_2$—CH$_2$); 3.43 (m, 2H, CH$_2$—CH$_2$—CH$_2$—NH); 3.95 (m, 2H, NH—CH$_2$—CH—NH); 4.57 (m, 1H, NH—CH$_2$—CH—NH); 5.03 (t, 1H, 1H, NH—CH$_2$—CH—NH); 6.42 and 7.15 (2d, 2H, H naphthyridine); 7.03 and 7.58 (2t, 2H, C=CH—CH=CH—CH=C); 7.43 and 9.88 (d and s, mobile H's); 8.19 and 8.66 (2d, 2H, C=CH—CH=CH—CH=C); 8.36 ppm (s, 1H, N=CH—N).

MS: 646 (MH+); 590 (MH-tBu+); 644-(M-H−).

Synthesis of 3-[5-ethyl-6-[4-(5,6,7,8-tetrahydro-(1,8) naphthyridin-2-yl)-piperidin-1-yl]-pyrimidin-4-ylamino]-2-[3-(4-methoxy-2-aminophenyl)-ureido]-propionic acid, bis(trifluoroacetate)

110 mg (0.17 mmole) of tert-butyl 3-[5-ethyl-6-[4-(5,6,7,8-tetrahydro-(1,8)naphthyridin-2-yl)-piperidin-1-yl]-pyrimidin-4-ylamino]-2-[3-(4-methoxy-2-nitro-phenyl)-reido]-propionate and 70 mg of zinc in 5 ml of acetic acid are stirred at ambient temperature until the starting product disappears according to TLC (silica gel, eluent: CH2Cl2-MeOH—H2O—AcOH 90-10-1-1). After filtering on Clarcel, cyclohexane is added and the reaction mixture is evaporated to dryness under reduced pressure (2 kPa). The residue is taken up in ethyl acetate and water. The organic phase is separated, dried over magnesium sulphate and the solvent evaporated off under reduced pressure (2 kPa). The crude product is chromatographed on alumina eluting with a gradient of methylene chloride-methanol of 100-0 to 90-10.

The product obtained is stirred in 4 ml of dichloromethane with 0.5 ml of trifluoroacetic acid at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into diisopropyl ether. The precipitate is filtered. 40 mg of expected product is obtained in the form of a beige solid.

TLC: Rf=0.27 (silica gel, eluent: dichloromethane-methanol-water-acetic acid 85-15-2-2)

MS: 662 (MH+); 606 (MH-tBu+); 660-(M-H−);

1H-NMR (DMSO d6): δ 1.07 (m, 3H, CH$_2$CH$_3$); 1.65 to 2.05 (m, 6H, CH$_2$—CH—CH$_2$ and CH$_2$—CH$_2$—CH$_2$—NH); 2.50 (masked, 2H, CH$_2$—CH$_3$); 2.77 (t, 2H, CH$_2$—CH$_2$—CH$_2$—NH); 2.87 (m, 1H, CH$_2$—CH—CH$_2$); 3.01 and 3.55 (bt and bd, 4H, CH$_2$—CH$_2$—N—CH$_2$—CH$_2$); 3.45 (m, 2H, CH$_2$—CH$_2$—CH$_2$—NH); 3.72 and 3.84 (2m, 2H, NH—CH$_2$—CH—NH); 4.53 (m, 1H, NH—CH$_2$—CH—NH); 6.68 and 7.56 (2d, 2H, H naphthyridine); 7.65 to 7.00 (m, 2H, C=CH—CH=CH—CH=C); 8.12 and 8.50 (m, 2H, C=CH—CH=CH—CH=C); 8.28 ppm (s, 1H, N=CH—N).

MS: 560 (MH+); 558-(M-H−)

Example 53

Synthesis of 3-[5-ethyl-6-[4-(5,6,7,8-tetrahydro-(1,8) naphthyridin-2-yl)-piperidin-1-yl]-pyrimidin-4-ylamino]-2-[3-(2-nitrophenyl)-ureido]-propionic acid, bis(trifluoroacetate)

30 mg (0.046 mmole) of tert-butyl 3-[5-ethyl-6-[4-(5,6,7,8-tetrahydro-(1,8)naphthyridin-2-yl)-piperidin-1-yl]-pyrimidin-4-ylamino]-2-[3-(2-nitrophenyl)-ureido]-propinate in 3 ml of dichloromethane with 0.5 ml of trifluoroacetic acid is stirred at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane then poured into diisopropyl ether. The precipitate is filtered. 35 mg of expected product is obtained in the form of a yellow solid.

TLC: Rf=0.50 (silica gel, eluent: dichloromethane-methanol-water-acetic acid 85-15-2-2)

MS: 590 (MH+); 588-(M-H−);

1H-NMR (CDCl$_3$): δ 1.19 (t, 3H, CH$_2$CH$_3$); 1.82 to 2.05 (m, 6H, CH$_2$—CH—CH$_2$ and CH$_2$—CH$_2$—CH$_2$—NH); 2.50 (t, 2H, CH$_2$—CH$_3$); 2.76 (t, 2H, CH$_2$—CH$_2$—CH$_2$—NH); 2.98 (bt, 1H, CH$_2$—CH—CH$_2$); 3.25 and 3.84 (bt and bd, 4H, CH$_2$—CH$_2$—N—CH$_2$—CH$_2$); 3.49 (m, 2H, CH$_2$—CH$_2$—CH$_2$—NH); 3.87 and 4.06 (2m, 2H, NH—CH$_2$—CH—NH); 4.63 (m, 1H, NH—CH$_2$—CH—NH); 6.41 and 7.37 (2d, 2H, H naphthyridine); 7.06 and 7.54 (2t, 2H, C=CH—CH=CH—CH=C); 8.11 and 8.32 (2d, 2H, C=CH—CH=CH—CH=C); 8.27 ppm (s, 1H, N=CH—N).

Examples 54 to 62

General Operating Method for the Preparation of the Ureas

Stage a

A mass $m_x$ (0.207 mmoles) of isocyanate in solution in 3 ml of tetrahydrofuran is added to 120 mg (0.207 mmoles) of tert-butyl 2-amino-3-{5-ethyl-6-[4-(5,6,7,8-tetrahydro-[1,8] naphthyridin-2-yl)-piperidin-1-yl]-pyrimidin-4-ylamino}-propionate in solution in 5 ml of tetrahydrofuran. The reaction mixture is stirred at ambient temperature for 3 hours and 30 minutes. Then, the solvent is evaporated off under reduced pressure (2 kPa) and the residue is chromatographed on silica gel with the following eluent: 100% ethyl acetate, ethyl acetate-dichloromethane/methanol (95/5) 50-50, ethyl acetate-dichloromethane/methanol (90-10) 50-50 and finishing with ethyl acetate/methanol (95-5).

A mass m$_y$ of expected product is obtained.
TLC: Rf (eluent: ethyl acetate-methanol (90/10).

Stage b

A mass m$_y$ of tert-butyl ester of Stage a) in 5 ml of dichloromethane with 500 µl of trifluoroacetic acid is stirred at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane then poured into ethyl ether. The precipitate is filtered. It is a mixture of the expected product and the by-product of cyclization. This mixture is purified on silica in order to produce a mass m$_z$ of expected product.
TLC: Rf (eluent: dichloromethane-methanol-water-acetic acid (90-10-1-1)

Example 54

Stage a

Synthesis of tert-butyl 2-(3-benzo[1,3]dioxol-5-yl-ureido)-3-{5-ethyl-6-[4-(5,6,7,8-tetrahydro-[1,8] naphthyridin-2-yl)-piperidin-1-yl]-pyrimidin-4-ylamino}-propionate 34 mg (0.207 mmoles) of 5-isocyanato-benzo[1,3]dioxole in solution in 3 ml of tetrahydrofuran is added to 120 mg (0.207 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate in solution in 5 ml of tetrahydrofuran. The reaction mixture is stirred at ambient temperature for 3 hours and 30 minutes. Then, the solvent is evaporated off under reduced pressure (2 kPa) and the residue is chromatographed on silica gel with the following eluent: 100% ethyl acetate, ethyl acetate-dichloromethane/methanol (95/5) 50-50, ethyl acetate-dichloromethane/methanol (90-10) 50-50 and finishing with ethyl acetate/methanol (95-5). 60 mg of expected product is obtained.

TLC: Rf=0.29 (silica gel, eluent: ethyl acetate-methanol 90/10)

1H-NMR (CDCl$_3$); δ 1.18 (t, 3H, CH2-CH3); 1.47 (s, 9H, tBu); 1.8 and 2.05 (2m, 6H, N—CH2-CH2-CH—CH2-CH2, CH2-CH2-CH2-NH); 2.48 (q, 2H, CH2-CH3); 2.67 (m, 3H, N—CH2-CH2-CH—CH2-CH2, CH2-CH2-CH2-NH); 2.95 and 3.63 (2m, 4H, N—CH2-CH2-CH—CH2-CH2); 3.45 (m, 2H, CH2-CH2-CH2-NH); 3.85 (m, 2H, NH—CH2-CH—NH); 4.6 (m, 1H, NH—CH2-CH—NH); 5.32 (t, 1H, NH mobile); 5.97 (s, 2H, O—CH2-O); 6.15 (bd, 1H, mobile NH); 6.42 and 7.2 (2d, 2H, CH=CH naphthyridine); 6.65 and 6.9 (3d, 3H, phenyl); 8.12 (s, 1H, N=CH—N).

MS: 645(MH+), 588(MH-tBu).

Stage b

Synthesis of 2-(3-benzo[1,3]dioxol-5-yl-ureido)-3-{5-ethyl-6-[4-(5,6,7,8-tetrahydro-[1,8]naphthyridin-2-yl)-piperidin-1-yl]-pyrimidin-4-ylamino}-propionic acid, bis(trifluoroacetate)

55 mg (0.085 mmoles) of tert-butyl 2-(3-benzo[1,3]dioxol-5-yl-ureido)-3-{5-ethyl-6-[4-(5,6,7,8-tetrahydro-[1,8]naphthyridin-2-yl)-piperidin-1-yl]-pyrimidin-4-ylamino}-propionate in 5 ml of dichloromethane with 500 µl of trifluoroacetic acid is stirred at ambient temperature for 13 hours.

Then toluene is added and the reaction mixture is evaporated to dryness under reduced pressure (2 kPa). The residue is solubilized in the minimum amount of dichloromethane then poured into ethyl ether. The precipitate is filtered, dried, then purified on silica.

39 mg of expected product is obtained.
TLC: Rf=0.25 (silica gel, eluent: dichloromethane-methanol-water-acetic acid 90-10-1-1.

1H-NMR (MeOD); δ 1.17 (t, 3H, CH2-CH3); 1.85 and 2 (m, 6H, N—CH2-CH2-CH—CH2-CH2, CH2-CH2-CH2-NH); 2.55 (q, 2H, CH2-CH3); 2.8 (m, 2H, N=CH2-CH2-CH—CH2-CH2, CH2-CH2-CH2-NH); 2.95 and 3.5 (2m, 4H, N—CH2-CH2-CH—CH2-CH2); 3.33 (m, 2H, CH2-CH2-CH2-NH); 3.65 and 3.95 (m, 2H, NH—CH2-CH—); 4.47 (m, 1H, NH—CH2-CH—NH); 5.32 (t, 1H, mobile NH); 5.5 (s, 1H, mobile NH); 5.9 (s, 2H, O—CH2-O); 7.5 (d, 1H, CH=CH naphthyridine); 6.6 and 7.02 (m, 3H, phenyl, 1H, mobile NH); 8.05 (s, 1H, N=CH—N).

MS: 589(MH+).

M$_x$: mass of isocyanate introduced
M$_y$: mass of ester obtained.
M$_z$: mass of acid obtained

| Example | Acid obtained | FW (Free base) | FW (Free base + 2 TFA) | Mz (mg) | MS (MH+) |
|---|---|---|---|---|---|
| 55 | (structure shown) 2 TFA | 558.69 | 786.69 | 48 | 559 |

-continued
| Ex-ample | Acid obtained | FW (Free base) | FW (Free base + 2 TFA) | Mz (mg) | MS (MH+) |
|---|---|---|---|---|---|
| 56 | 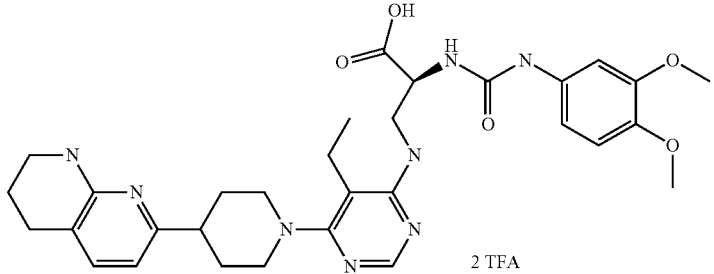 [SMILES: CCc1c(NC[C@H](NC(=O)Nc2ccc(OC)c(OC)c2)C(=O)O)ncnc1N1CCC(c2ccc3c(n2)NCCC3)CC1] 2 TFA | 604.71 | 832.71 | 51 | 605 |
| 57 | 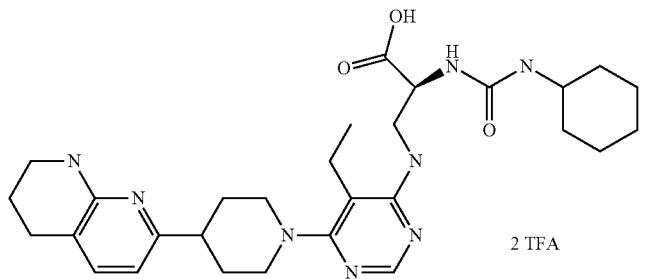 [SMILES: CCc1c(NC[C@H](NC(=O)NC2CCCCC2)C(=O)O)ncnc1N1CCC(c2ccc3c(n2)NCCC3)CC1] 2 TFA | 550.71 | 778.71 | 51 | 551 |
| 58 | 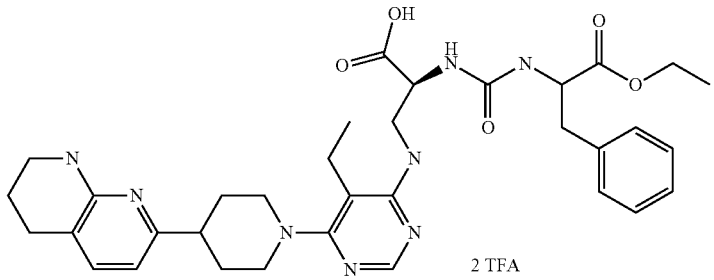 [SMILES: CCOC(=O)C(Cc1ccccc1)NC(=O)N[C@@H](CNc1ncnc(N2CCC(c3ccc4c(n3)NCCC4)CC2)c1CC)C(=O)O] 2 TFA | 644.78 | 872.78 | 49 | 645 |
| 59 | 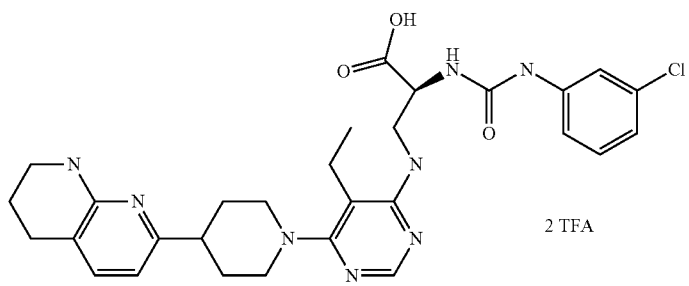 [SMILES: CCc1c(NC[C@H](NC(=O)Nc2cccc(Cl)c2)C(=O)O)ncnc1N1CCC(c2ccc3c(n2)NCCC3)CC1] 2 TFA | 579.11 | 807.11 | 48 | 579 |
| 60 | 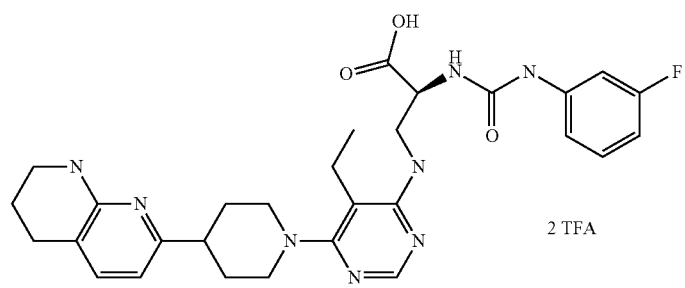 [SMILES: CCc1c(NC[C@H](NC(=O)Nc2cccc(F)c2)C(=O)O)ncnc1N1CCC(c2ccc3c(n2)NCCC3)CC1] 2 TFA | 562.65 | 790.65 | 50 | 563 |

| Example | Acid obtained | FW (Free base) | FW (Free base + 2 TFA) | Mz (mg) | MS (MH+) |
|---|---|---|---|---|---|
| 61 | 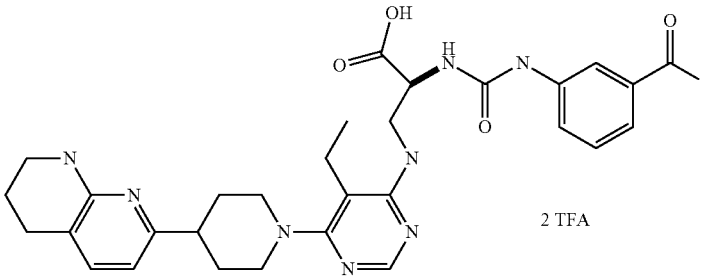 2 TFA | 602.70 | 830.70 | 43 | 603 |
| 62 | 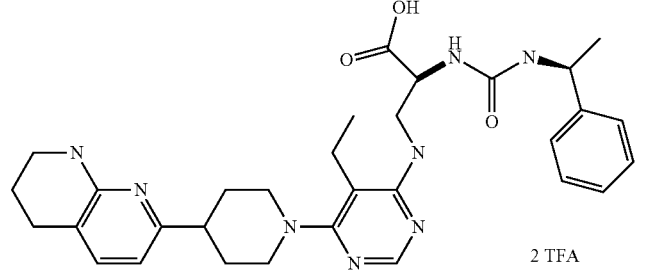 [SMILES: CCc1c(NC[C@H](NC(=O)N[C@@H](C)c2ccccc2)C(=O)O)ncnc1N1CCC(c2ccc3c(n2)NCCC3)CC1] 2 TFA | 572.71 | 800.71 | 29 | 573 |
The products obtained above can be prepared from the following raw materials:
| Example | Isocyanate | Mx (mg) | expected product |
|---|---|---|---|
| 55 | 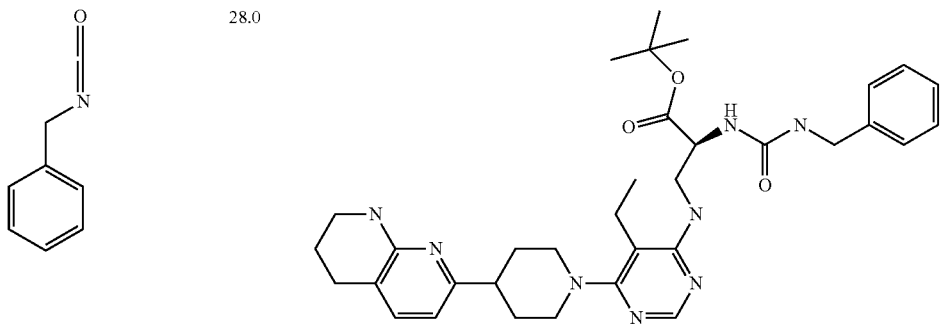 | 28.0 | |
| 56 | 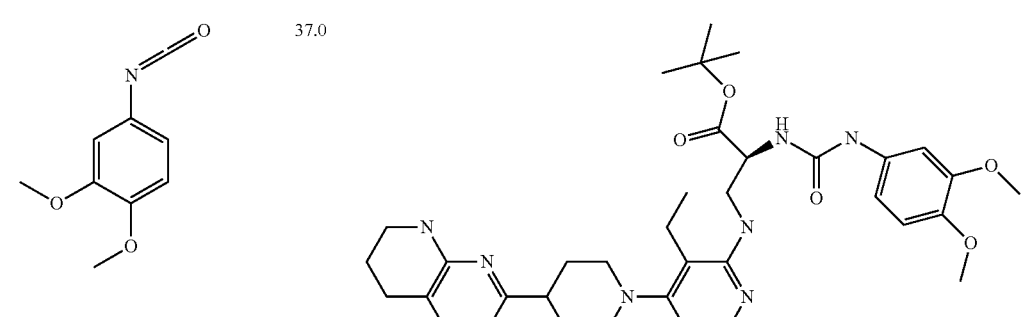 | 37.0 | |

-continued
| 57 | 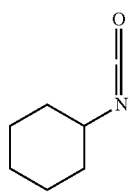 | 26.0 | 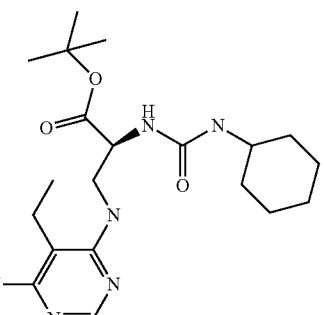 |
| 58 | 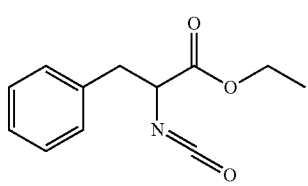 [SMILES: CCOC(=O)C(Cc1ccccc1)N=C=O] | 45.5 | 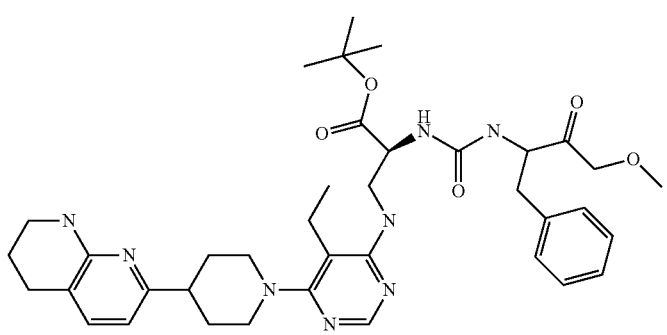 [SMILES: CCc1c(NC[C@H](NC(=O)NC(Cc2ccccc2)C(=O)COC)C(=O)OC(C)(C)C)ncnc1N1CCC(c2ccc3c(n2)NCCC3)CC1] |
| 59 | 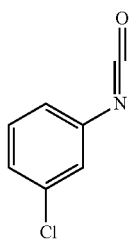 | 31.7 | 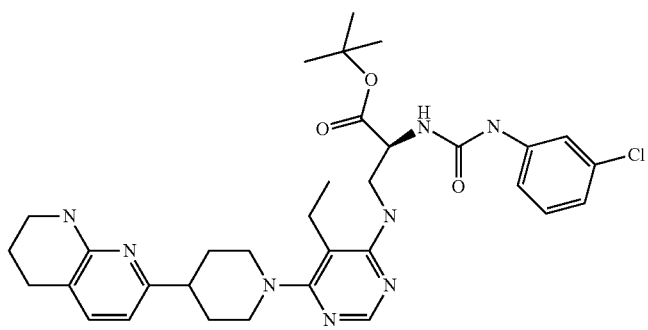 [SMILES: CCc1c(NC[C@H](NC(=O)Nc2cccc(Cl)c2)C(=O)OC(C)(C)C)ncnc1N1CCC(c2ccc3c(n2)NCCC3)CC1] |
| 60 | 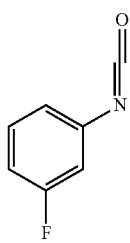 | 29.0 | 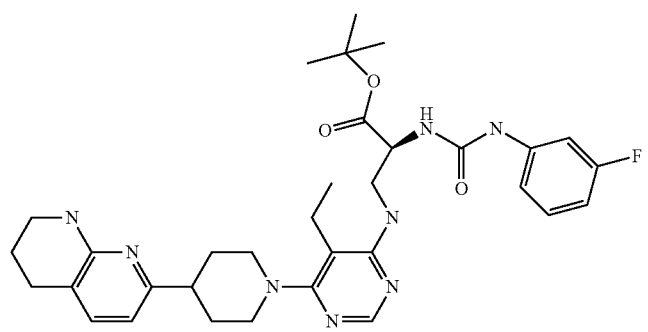 [SMILES: CCc1c(NC[C@H](NC(=O)Nc2cccc(F)c2)C(=O)OC(C)(C)C)ncnc1N1CCC(c2ccc3c(n2)NCCC3)CC1] |
| Example | M_y (mg) | Yield | MS (MH+) |
| --- | --- | --- | --- |
| 55 | 56.5 | 44 | 615 |
| 56 | 51.7 | 38 | 661 |
| 57 | 80 | 63 | 607 |
| 58 | 56 | 38 | 701 |
| 59 | 54.4 | 41 | 635 |
| 60 | 57.6 | 45 | 619 |

Example 63

Synthesis of tert-butyl 2-{N-[(dimethylamino)sulphonylamino]}-3-{5-ethyl-6-[4-(5,6,7,8-tetrahydro-[1,8]naphthyridin-2-yl)-piperidin-1-yl]-pyrimidin-4-ylamino}-propionate 16 ml of triethylamine is added to a solution of 2 g (4.27 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate in 200 ml of anhydrous tetrahydrofuran then a solution of 700 µl (6.4 mmoles) of dimethylaminosulphonyl chloride in 40 ml of anhydrous tetrahydrofuran is added. The addition is carried out dropwise, at ambient temperature, under a current of nitrogen. The reaction mixture is maintained under stirring for 48 hours. Then, the solvent is evaporated off under reduced pressure (2 kPa) and the residue is taken up in a mixture of water, a saturated solution of sodium bicarbonate and ethyl acetate. The organic phase is decanted, dried over magnesium sulphate and the solvent eliminated by evaporation under reduced pressure (2 kPa). The residue is chromatographed on silica gel eluting with 100% ethyl acetate. 1.1 g of expected product is obtained.

TLC: Rf=0.1 (silica gel, eluent: 100% ethyl acetate)

1H-NMR (CDCl$_3$); δ 1.48 (s, 9H, tBu); 1.93 and 2.02 (2m, 6H, N—CH2-CH2-CH—CH2-CH2, CH2-CH2-CH2-NH); 2.01 (s, 3H, CH3); 2.73 (m, 3H, N—CH2-CH2-CH—CH2-CH2, CH2-CH2-CH2-NH); 2.81 (s, 6H, N(CH3)$_2$); 2.95 and 3.70 (2m, 4H, N—CH2-CH2-CH—CH2-CH2); 3.44 (m, 2H, CH2-CH2-CH2-NH); 3.81 and 3.91 and 4.11 (3m, 3H, NH—CH2-CH—NH); 4.87 (t, 1H, mobile NH); 5.86 (bd, 1H, mobile NH); 6.41 and 7.17 (2d, 2H, CH=CH naphthiridine); 8.28 (s, 1H, N=CH—N).

MS: 575(MH+).

Example 64

Synthesis of 2-{N-[(dimethylamino)sulphonylamino]}-3-{5-ethyl-6-[4-(5,6,7,8-tetrahydro-[1,8]naphthyridin-2-yl)-piperidin-1-yl]-pyrimidin-4-ylamino}-propionic acid, bis(trifluoroacetate)

290 mg (0.5 mmoles) of tert-butyl 2-{N-[(dimethylamino)sulphonylamino]}-3-{5-ethyl-6-[4-(5,6,7,8-tetrahydro-[1,8]naphthyridin-2-yl)-piperidin-1-yl]-pyrimidin-4-ylamino}-propionate in 30 ml of dichloromethane with 3 ml of trifluoroacetic acid is stirred at ambient temperature until the starting product disappears according to TLC (silica gel, eluent: CH2Cl2-MeOH—H2O—AcOH 90-10-1-1). Toluene is added and the reaction mixture is evaporated to dryness under reduced pressure (2 kPa). The residue is solubilized in the minimum amount of dichloromethane with a little methanol then poured into ethyl ether. The precipitate is filtered. 197.3 mg of expected product is obtained.

TLC: Rf=0.2 (silica gel, eluent: dichloromethane-methanol-water-acetic acid 90-10-1-1).

1H-NMR (CDCl$_3$); δ 1.94 and 2.04 (2m, 6H, N—CH2-CH2-CH—CH2-CH2, CH2-CH2-CH2-NH); 2.11 (s, 3H, CH3); 2.74 (s, 6H, N(CH3)$_2$); 2.76 (m, 2H, CH2-CH2-CH2-NH); 3.01 (m, 1H, N—CH2-CH2-CH—CH2-CH2); 3.29 and 3.96 (2m, 4H, N—CH2-CH2-CH—CH2-CH2); 3.52 (m, 2H, CH2-NH); 3.80 and 4.04 and 4.21 (3m, 3H, NH—CH2-CH—NH); 6.42 and 7.39 (2d, 2H, CH=CH naphthiridine); 7.12 (m, 1H, mobile NH); 8.33 (s, 1H, N=CH—N).

MS: 519(MH+).

Example 65

Synthesis of tert-butyl 3-[5-methyl-6-[4-(5,6,7,8-tetrahydro-(1,8)naphthyridin-2-yl)-piperidin-1-yl]-pyrimidin-4-ylamino]-N-[(1,1-dimethylthyloxycarbonyl)aminosulphonyl]-propionate 111 mg (1.5 mmoles) of terbutanol in solution in 30 ml of dichloromethane is added dropwise to 0.13 ml (1.5 mmoles) of chlorosulphonyl isocyanate in solution in 30 ml of dichloromethane and the reaction medium is stirred at ambient temperature for 45 minutes. This solution is then introduced dropwise into a mixture of 700 mg (1.5 mmoles) of tert-butyl 2-amino-3-{5-ethyl-6-[4-(5,6,7,8-tetrahydro-[1,8]naphthyridin-2-yl)-piperidin-1-yl]-pyrimidin-4-ylamino}-propionate and 0.35 ml (2 mmoles) of diisopropylethylamine in 400 ml of dichloromethane. The reaction mixture is stirred at ambient temperature for 2 hours. Then, the solvent is evaporated off under reduced pressure (2 kPa). The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). 830 mg of expected product in the form of a yellow oil is obtained.

TLC: Rf=0.12 (silica gel, eluent: dichloromethane-methanol-water-acetic acid 90-10-1-1)

1H-NMR (CDCl$_3$); δ 1.48 and 1.51 ppm (2s, 18H, tBu); 1.85 to 2.15 (m, 6H, CH$_2$—CH—CH$_2$ and CH$_2$—CH$_2$—CH$_2$—NH); 1.98 (s, 3H, CCH$_3$); 2.85 to 3.05 (m, 3H, CH$_2$—CH$_2$—CH$_2$—NH and CH$_2$—CH—CH$_2$); 2.78 and 3.74 (bt and bd, 4H, CH$_2$—CH$_2$—N—CH$_2$—CH$_2$); 3.52 (m, 2H, CH$_2$—CH$_2$—CH$_2$—NH); 3.89 and 3.99 (2dt, 2H, NH—CH$_2$—CH—NH); 4.32 (dt, 1H, NH—CH$_2$—CH—NH); 4.88 (bt, 1H, 1H, NH—CH$_2$—CH—NH); 6.42 and 7.36 (2d, 2H, H naphthyridine); 8.28 ppm (s, 1H, N=CH—N).

MS: 647 (MH+); 645 (MH−).

Synthesis of tert-butyl 3-[5-methyl-6-[4-(5,6,7,8-tetrahydro-(1,8)naphthyridin-2-yl)-piperidin-1-yl]-pyrimidin-4-ylamino]-N—[N,N-(1,1-dimethylethyloxycarbonyl) (phenylmethyl)aminosulphonyl]-propionate 0.047 ml of diethyl azodicarboxylate is added to a mixture of 130 mg (0.2 mmole) of tert-butyl 3-[5-methyl-6-[4-(5,6,7,8-tetrahydro-(1,8)naphthyridin-2-yl)-piperidin-1-yl]-pyrimidin-4-ylamino]-N-[(1,1-dimethylethyloxycarbonyl)aminosulphonyl]-propionate and 60 mg (0.3 mmole) of triphenylphosphine in solution in 10 ml of dichloromethane then 0.041 ml (0.4 mmole) of benzyl alcohol in solution in 5 ml of dichloromethane is added dropwise and the reaction medium is stirred at ambient temperature for 1 hour. Then another 0.047 ml of diethyl azodicarboxylate is added then 0.041 ml (0.4 mmole) of benzyl alcohol in solution in 5 ml of dichloromethane is added dropwise and the reaction medium is stirred at ambient temperature for 1 hour. Then, the solvent is evaporated off under reduced pressure (2 kPa) The residue obtained is taken up in a mixture of water, ethyl acetate and a saturated solution of sodium bicarbonate. The organic phase is separated and the aqueous phase reextracted with ethyl acetate. The collected organic phases are dried over magnesium sulphate then the solvent is evaporated off under reduced pressure (2 kPa). The crude product is purified by chromatography on silica eluting with an elution gradient of methylene chloride-methanol of 100-0 to 90-10. 80 mg of expected product is obtained in the form of a beige solid.

TLC: Rf=0.12 (silica gel, eluent: dichloromethane-methanol-water-acetic acid 90-10-1-1)

1H-NMR (CDCl₃); δ 1.38 and 1.53 ppm (2s, 18H, tBu); 1.85 to 2.15 (m, 6H, CH₂—CH—CH₂ and CH₂—CH₂—CH₂—NH); 1.98 (s, 3H, CCH₃); 2.75 and 3.71 (td and m, 4H, CH₂—CH₂—N—CH₂—CH₂); 2.82 (td, 1H, CH₂—CH—CH₂); 3.05 (m, 3H, CH₂—CH₂—CH₂—NH); 2.96 (dt, 2H, CH₂—CH₂—CH₂—NH); 3.59 and 3.81 (2m, 2H, NH—CH₂—CH—NH); 4.78 (t, 1H, NH—CH₂—CH—NH); 4.72 and 4.96 (2d, 2H, CH₂-Ph); 6.42 and 7.33 (2d, 2H, H naphthyridine); 7.32 (m, 5H, CH₂-Ph) 8.26 (s, 1H, N=CH—N).

MS: 737 (MH+); 735 (MH-).

Synthesis of 3-[5-methyl-6-[4-(5,6,7,8-tetrahydro-(1,8)naphthyridin-2-yl)-piperidin-1-yl]-pyrimidin-4-ylamino]-N—[N,N-(1,1-dimethylethyloxycarbonyl)(phenylmethyl)aminosulphonyl]-propionic acid, bis (trifluoroacetate)

73 mg (0.1 mmole) of tert-butyl 3-[5-methyl-6-[4-(5,6,7,8-tetrahydro-(1,8)naphthyridin-2-yl)-piperidin-1-yl]-pyrimidin-4-ylamino]-N—[N,N-(1.1dimethylethyloxycarbonyl)(phenylmethyl)aminosulphonyl]-propionate in 5 ml of dichloromethane with 1 ml of trifluoroacetic acid is stirred at ambient temperature for 3 hours. Toluene is added and the reaction mixture is evaporated to dryness under reduced pressure (2 kPa). The residue is solubilized in the minimum amount of dichloromethane then poured into diisopropyl ether. The precipitate is filtered. 35 mg of expected product is obtained in the form of a white solid.

MS: 579 (MH-).

Example 66

Synthesis of the hydrochloride of 2-(4-methoxy-benzenesulphonylamino)-3-{2-methoxy-5-methyl-6-[4-(5,6,7,8-tetrahydro-[1,8]naphthyridin-2-yl)-piperidin-1-yl]-pyrimidin-4-ylamino}-propionic acid 2 g (2.99 moles) of the tert-butyl ester of 2-(4-methoxy-benzenesulphonyl-amino)-3-{2-methoxy-5-methyl-6-[4-(5,6,7,8-tetrahydro-[1,8]naphthyridin-2-yl)-piperidin-1-yl]-pyrimidin-4-ylamino}-propionic acid in 20 ml of a solution of 6N hydrochloric acid in water is stirred, the reaction mixture remains heterogeneous, rapid caking of the hydrochloride of the ester formed occurs, then 20 ml of distilled water is added in order to improve the solubility.

Stirring is maintained at ambient temperature for 20 hours before adding two times 5 ml of 6N hydrochloric acid in water.

The reaction mixture is maintained under stirring for a total of 60 hours. Then it is concentrated to dryness under reduced pressure (2 kPa) in the presence successively of toluene and isopropanol.

The residue obtained is solubilized in the minimum amount of dichloromethane and methanol then poured into ethyl ether twice. The precipitate formed is filtered, washed with ether then with pentane and dried under vacuum. 1.62 g of a white powder is obtained.

TLC: Rf=0.41 (silica gel, eluent: dichloromethane-methanol 90-10)

1H-NMR (CDCl₃); δ 0.95 (m, 7H, —CH3, CH2-CH2-CH2-CH2-CH2); 1.05 (m, 2H, CH2-CH2-CH2-CH2-CH2); 1.8 (m, 4H, CH2-CH2-CH—CH2-CH2); 1.92 (m, 1H, CH2-CH2-CH—CH2-CH2); 2.17 and 2.67 (2m, 4H, N—CH2-CH2-CH—CH2-CH2), 2.5 (t, 2H, CH2-CH2-CH2-NH); 2.57 and 2.9 (2m, 2H, NH—CH2-CH—NH); 2.82 (s, 3H, —OCH3); 3.05 (s, 3H, —OCH3); 3.23 (m, 1H, NH—CH2-CH—NH); 5.67 and 6.6 (2d, 2H, CH=CH naphthyridine); 5.95 and 6.7 (2d, 4H, CH=CH benzene)

MS: 612(MH)+; 306(MH) 2+; 610(MH)

Synthesis of 2-(4-methoxy-benzenesulphony-lamino)-3-{2-methoxy-5-methyl-6-[4-(5,6,7,8-tetrahydro-[1,8]naphthyridin-2-yl)-piperidin-1-yl]-pyrimidin-4-ylamino}-propionic acid tert-butyl ester Stage 1

Synthesis of 2-amino-3-{2-methyl, 5-methoxy-6-[4-(5,6,7,8-tetrahydro-[1,8]naphthyridin-2-yl)-piperidin-1-yl]-pyrimidin-4-ylamino}-propionic acid tert-butyl ester:

500 ml of 100% acetic acid and 500 mg of platinum oxide (5-10%) are loaded into a single-necked flask containing 5.4 g (8.5 mmoles) of 2-benzyloxycarbonylamino-3-{2-methyl, 5-methoxy-6-[4-(5,6,7,8-tetrahydro-[1,8]naphthyridin-2-yl)-piperidin-1-yl]-pyrimidin-4-ylamino}-propionic acid tert-butyl ester. This mixture is purged under vacuum and left under stirring at AT and under hydrogen at atmospheric pressure for 20 hours.

The heterogeneous medium obtained is filtered on clarcel. The filtrate is concentrated to dryness in the presence of cyclohexane, then taken up in a mixture of ethyl acetate and a saturated solution of sodium bicarbonate. The organic phase is extracted and dried over magnesium sulphate then the solvent is evaporated off under vacuum. The residue obtained is chromatographed on silica gel with the following eluent: dichloromethane-heptane 50-50 to (dichloromethane-methanol 90-10/ethyl acetate) (50-50). 2.75 g of expected product is obtained in the form of pale yellow crystals (yield=65%).

TLC: Rf=0.32, eluent: (dichloromethane-methanol 90-10/ethyl acetate) (50-50) on silica 1H-NMR (CDCl3); δ 1.47 (s, 9H, tBu); 1.93 (m, 9H, N—CH2-CH2-CH—CH2-CH2, CH2-CH2-CH2-NH, CH3-); 2.7 (m, 3H, N—CH2-CH2-CH—CH2-CH2, CH2-CH2-CH2-NH); 2.92 and 3.72 (2m, 4H, CH2-CH2-N—CH2-CH2-CH); 3.42 (m, 2H, CH2-CH2-CH2-NH); 3.5 (m, 2H, NH—CH2-CH—NH); 3.65 (m, 1H, NH—CH2-CH—NH); 3.9 (s, 3H, —N=N—OCH3); 5.0 and 5.65 (m, 2H, mobile NH); 6.4 and 7.13 (2d, 2H, CH=CH naphthyridine)

MS: 498 (MH)+

Stage 2

915 mg (4.43 mmoles) of 4-methoxy-benzenesulphonyl chloride in solution in 200 ml of tetrahydrofuran is added dropwise to a mixture of 2.2 g (4.43 mmoles) of 2-amino-3-[2-methoxy-5-methyl-6-[4-(5,6,7,8-tetrahydro-[1,8]naphthyridin-2-yl)piperidin-1-yl)-pyrimidin-4-ylamino]-propionic acid tert-butyl ester in solution in 800 ml of tetrahydrofuran and 950 µl of triethylamine. The reaction medium is stirred at ambient temperature overnight. Then, the solvent is evaporated off under reduced pressure (2 kPa) and the residue is chromatographed on alumina with the following eluent: ethyl acetate-dichloromethane 50-50 to ethyl acetate-(dichloromethane/methanol) (90/10) 50-50.

2.02 g (yield=68%) of expected product is obtained.

TLC: Rf=0.19 (silica gel, eluent: 100% ethyl acetate)

1H-NMR (CDCl₃); δ 1.3 (s, 9H, tBu); 1.95 (m, 9H, N—CH2-CH2-CH—CH2-CH2, CH2-CH2-CH2-NH,

—CH3); 2.75 (m, 3H, N—CH2-CH2-CH—CH2-CH2, CH2-CH2-CH2-NH); 2.95 and 3.75 (2m, 4H, N—CH2-CH2-CH—CH2-CH2); 3.47 (m, 2H, CH2-CH2-CH2-NH); 3.6 (m, 1H, NH—CH2-CH—NH); 3.85 (s, 3H, N═C(OCH3)-N); 3.9 (s, 3H, Ph-OCH3); 3.97 (m, 2H, NH—CH2-CH═NH); 4.85 (m, H, NH mobile); 5.8 (bd, 1H, NH mobile); 6.42 and 7.22 (2d, 2H, CH═CH naphthyridine); 6.92 and 7.75 (2d, 4H, CH═CH benzene)

MS: 668(MH)+; 334(MH) 2+

Example 67

Synthesis of the hydrochloride of 2-(4-methoxy-benzenesulphonylamino)-3-{2,5-dimethyl-6-[4-(5,6,7,8-tetrahydro-[1,8]naphthyridin-2-yl)-piperidin-1-yl]-pyrimidin-4-ylamino}-propionic acid 3 g (4.6 moles) of 2-(4-methoxy-benzenesulphonylamino)-3-{(2,5)-dimethyl-6-[4-(5,6,7,8-tetrahydro-[1,8]naphthyridin-2-yl)-piperidin-1-yl]-pyrimidin-4-ylamino}-propionic acid tert-butyl ester in 30 ml of a solution of 6N hydrochloric acid in water is stirred, the reaction mixture remains heterogeneous, rapid caking of the hydrochloride of the ester formed occurs, then 20 ml of 6N hydrochloric acid in water is added, the mixture becomes clear.

Stirring is maintained at ambient temperature for 4 hours, the mixture becomes milky.

Then the latter is concentrated to dryness under reduced pressure (2 kPa) in the presence successively of toluene and isopropanol.

The residue obtained is solubilized in the minimum amount of dichloromethane and methanol then poured into ethyl ether. The precipitate formed is filtered, washed with ether then with pentane and dried under vacuum. 2.86 g of a white powder is obtained.

TLC: Rf=0.23 (silica gel, eluent: dichloromethane-methanol-water-acetic acid 85-15-2-2)

1H-NMR (MeOD); δ 1.05 (m, 9H, —CH3, N—CH2-CH2-CH—CH2-CH2, CH2-CH2-CH2-NH); 1.57 (s, 3H, —CH3); 1.85 (t, 2H, CH2-CH2-CH2-NH); 2.02 (m, 1H, N—CH2-CH2-CH—CH2-CH2); 2.32 and 2.8 (2m, 4H, N—CH2-CH2-CH═CH2-CH2); 2.55 (m, 2H, CH2-CH2-CH2-NH); 2.52 and 2.95 (2m, 2H, NH—CH2-CH—NH); 2.87 (s, 3H, —OCH3); 3.23 (m, 1H, NH—CH2-CH—NH); 5.72 and 6.65 (2d, 2H, CH═CH naphthyridine); 6.02 and 6.75 (2d, 4H, CH═CH benzene)

MS: 596(MH)+; 594(MH)−

Synthesis of 2-(4-methoxy-benzenesulphonylamino)-3-{(2,5)-dimethyl-6-[4-(5,6,7,8-tetrahydro-[1,8]naphthyridin-2-yl)-piperidin-1-yl]-pyrimidin-4-ylamino}-propionic acid tert-butyl ester Stage 1

Synthesis of 2-amino-3-{2,5-dimethyl-6-[4-(5,6,7,8-tetrahydro-[1,8]naphthy-ridin-2-yl)-piperidin-1-yl]-pyrimidin-4-ylamino}-propionic acid tert-butyl ester 1 liter of 100% acetic acid and 1 g of platinum oxide (5-10%) is charged into a single-necked flask containing 13 g (21.1 mmoles) of 2-benzyloxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid ter-butyl ester, prepared according to the International Application (WO2004048375(A1). This mixture is purged under vacuum and left under stirring at AT and under hydrogen at atmospheric pressure for 20 hours.

The heterogeneous medium obtained is filtered on clarcel. The filtrate is concentrated to dryness in the presence of cyclohexane, then taken up in a mixture of ethyl acetate and a saturated solution of sodium bicarbonate. The organic phase is extracted and dried over magnesium sulphate then the solvent is evaporated under vacuum. The residue obtained is chromatographed on silica gel with the following eluent: 100% dichloromethane to dichloromethane-methanol 95-5. 7.6 g of expected product is obtained in the form of pale yellow crystals (yield=74%).

TLC: Rf=0.23 (eluent: dichloromethane-methanol 95-5 on silica)

1H-NMR (CDCl$_3$); δ 1.47 (s, 9H, tBu); 1.92 (m, 6H, CH2-CH2-CH2-NH, CH2-CH2-CH—CH2-CH2); 2.05 (s, 3H, —CH3); 2.42 (s, 3H, N═N—CH3); 2.72 (t, 2H, CH2-CH2-CH2-NH); 2.85 (m, 1H, N—CH2-CH2-CH—CH2-CH2); 2.97 and 3.65 (2m, 4H, CH2-CH2-N—CH2-CH2-CH); 3.47 (m, 2H, CH2-CH2-CH2-NH); 3.5 and 3.7 (2m, 2H, NH—CH2-CH—NH); 3.9 (m, 1H, NH—CH2-CH—NH); 4.97 and 5.55 (m, 2H, NH mobile); 6.37 and 7.25 (2d, 2H, CH═CH naphthyridine)

MS: 482 (MH)+; 426 [MH-tBu]+

Stage 2

A mixture of 750 mg (1.56 mmoles) of 2-Amino-3-[(2.5)-dimethyl-6-[4-(5,6,7,8-tetrahydro-[1,8]naphthyridin-2-yl)-pyrimidin-4-ylamino]-propionic acid tert-butyl ester in solution in 350 ml of tetrahydrofuran and 7 ml of triethylamine, is added dropwise 322 mg (1.56 mmoles) of chloride of 4-methoxy-benzenesulphonyl in solution in 35 ml of tetrahydrofuran. The reaction medium is stirred at ambient temperature overnight. Then, the solvent is evaporated under reduced pressure (2 kPa) and the residue is chromatographed on alumina with the eluent following: ethyl acetate-dichloromethane 50-50 to ethyl acetate-methanol) (98/2).

2.02 g (yield=68%) of expected product is obtained.

TLC: Rf=0.25 (silica gel, eluent: ethyl acetate-methanol (90/10)

1H-NMR (CDCl$_3$); δ 1.32 (s, 9H, tBu); 1.9 (m, 6H, N—CH2-CH2-CH—CH2-CH2, CH2-CH2-CH2-NH); 2.05 (s, 3H, —CH3); 2.45 (s, 3H, —CH3); 2.75 (m, 3H, N—CH2-CH2-CH═CH2-CH2, CH2-CH2-CH2-NH); 2.95 and 3.7 (2m, 4H, N—CH2-CH2-CH—CH2-CH2); 3.47 (m, 2H, CH2-CH2-CH2-NH); 3.8 (m, 2H, NH—CH2-CH—NH); 3.85 (s, 3H, Ph-OCH3); 3.95 (m, 1H, NH—CH2-CH—NH); 4.65 and 7.1 (2m, 2H, NH mobile); 6.42 and 7.25 (2d, 2H, CH═CH naphthyridine); 6.92 and 7.75 (2d, 4H, CH═CH benzene)

MS: 652 (MH)+; 650 (MH)−

Examples 68 to 80

Stage a

Activation of the Alcohol 1.5 equivalents of di(N-succinimidyl)carbonate is solubilized in 4 ml of methylene chloride. One equivalent of alcohol solubilized in methylene chloride, as well as 2 equivalents of triethylamine are added at ambient temperature. The reaction mixture is left under stirring for 6 hours.

Then, if the activated alcohol formed is stable, it can be isolated by extraction with ethyl acetate and washing with sodium bicarbonate before addition of the amine.

Stage b

Addition of the Amine 0.8 equivalent of ter-butyl ester of 2-amino-3-{2,5-dimethyl-6-[4-(5,6,7,8-tetrahydro-[1.8]naphthyridin-2-yl)-piperidin-1-yl]-pyrimidin-4-ylamino}-propionic acid, as well as one equivalent of triethylamine are added to the activated alcohol.

The mixture is left under stirring overnight at ambient temperature.

The reaction mixture is then extracted with ethyl acetate after washing with a saturated solution of sodium bicarbonate. The organic phase obtained is dried over magnesium sulphate before being concentrated to dryness under reduced pressure (2 kPa). The residue is then chromatographed on alumina with the following eluent: ethyl acetate/isopropyl ether to 100% ethyl acetate. The expected ester is obtained with a yield of 38 to 90%.

Stage c

Hydrolysis of the Ester

A mass $m_C$ of (1,1-dimethylethyl) 3-[[2,5-dimethyl-6-[4-(1,2,3,4-tetrahydro-1,8-naphthyridin-7-yl)-1-piperidinyl]-4-pyrimidinyl]amino]-N-(alkyl)alaninate in 5 ml of dichloromethane and 500 µl of trifluoroacetic acid is stirred at ambient temperature until the starting product disappears according to TLC (silica gel, eluent: CH2Cl2-MeOH—H2O—AcOH 90-10-1-1). Then toluene is added to the reaction mixture for evaporation to dryness under reduced pressure (2 kPa). The residue obtained is solubilized in a minimum amount of dichloromethane then poured into diisopropyl ether. The precipitate is filtered, washed with pentane then dried. A mass $m_D$ of expected acid is obtained in the form of powder.

| Example | alcohol used | Expected product | FW | Yield | MS [M/Z + H] |
|---|---|---|---|---|---|
| 68 | | | 631.8 | 38 | 632 |
| 69 | | | 673.91 | 51 | 674 |

| | | | | |
|---|---|---|---|---|
| 70 | 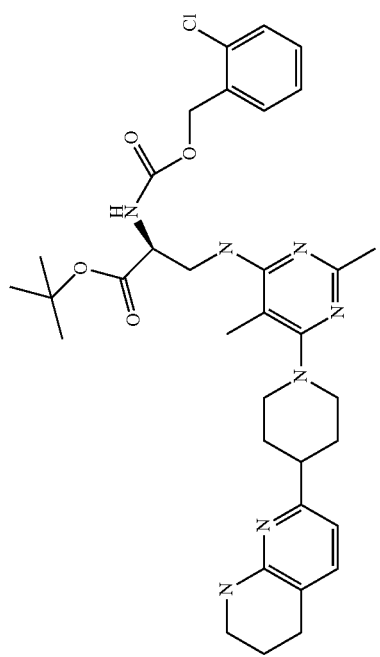<br>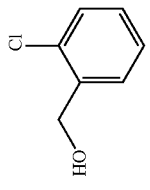 | 650.23 | 49 | 650 |
| 71 | 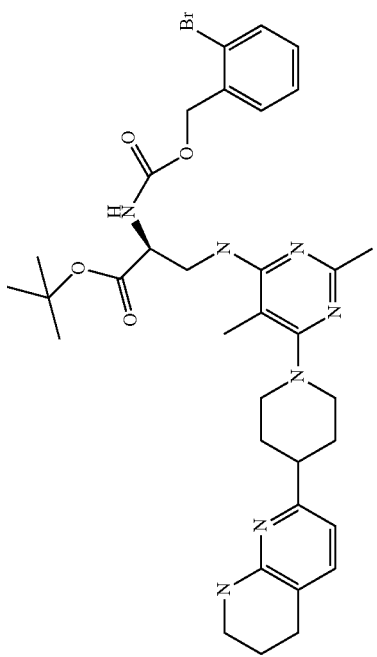 | 694.68 | 59 | 694 |

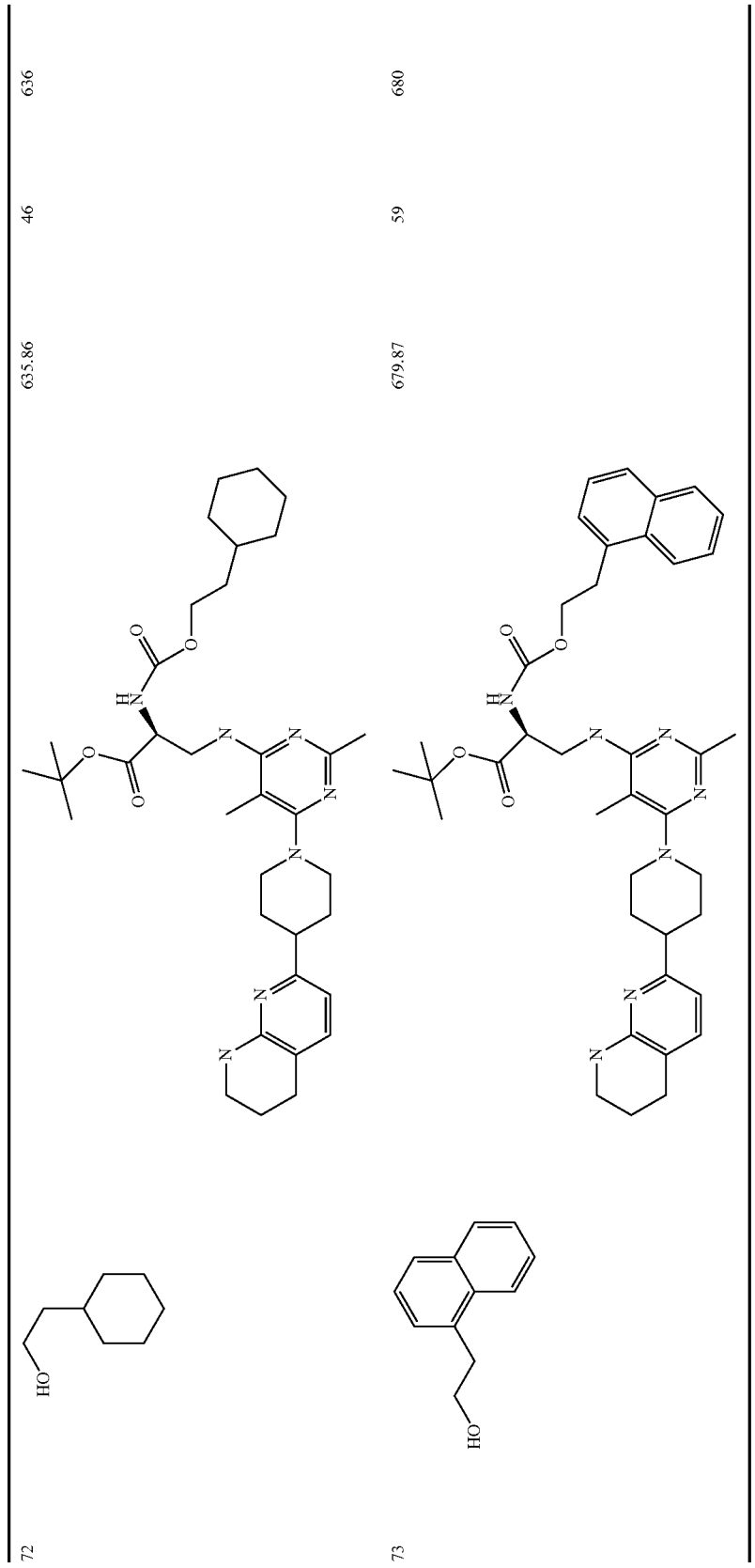

| examples | Alcohol used | Expected product | FW | Yield | MS [M/Z + H] |
|---|---|---|---|---|---|
| 74 |  | 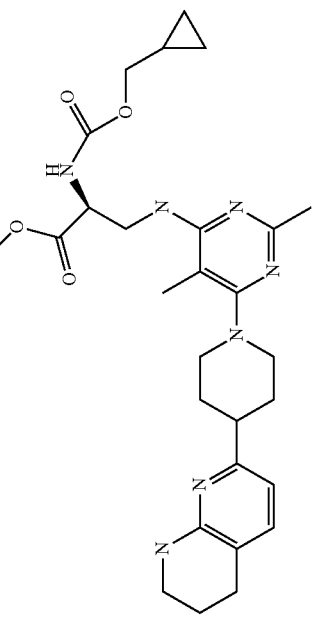 | 579.75 | 64 | 580 |
| 75 | 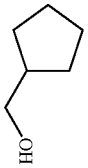 | 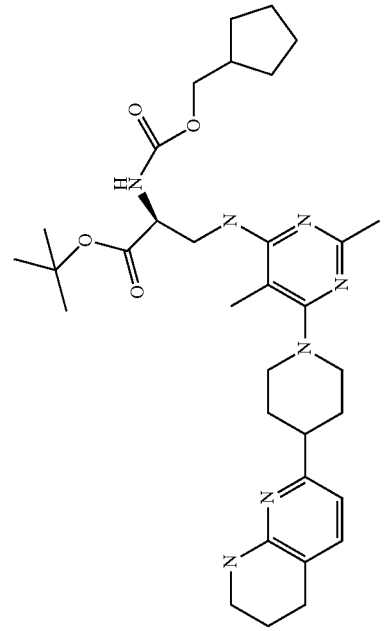 | 607.8 | 66 | 608 |

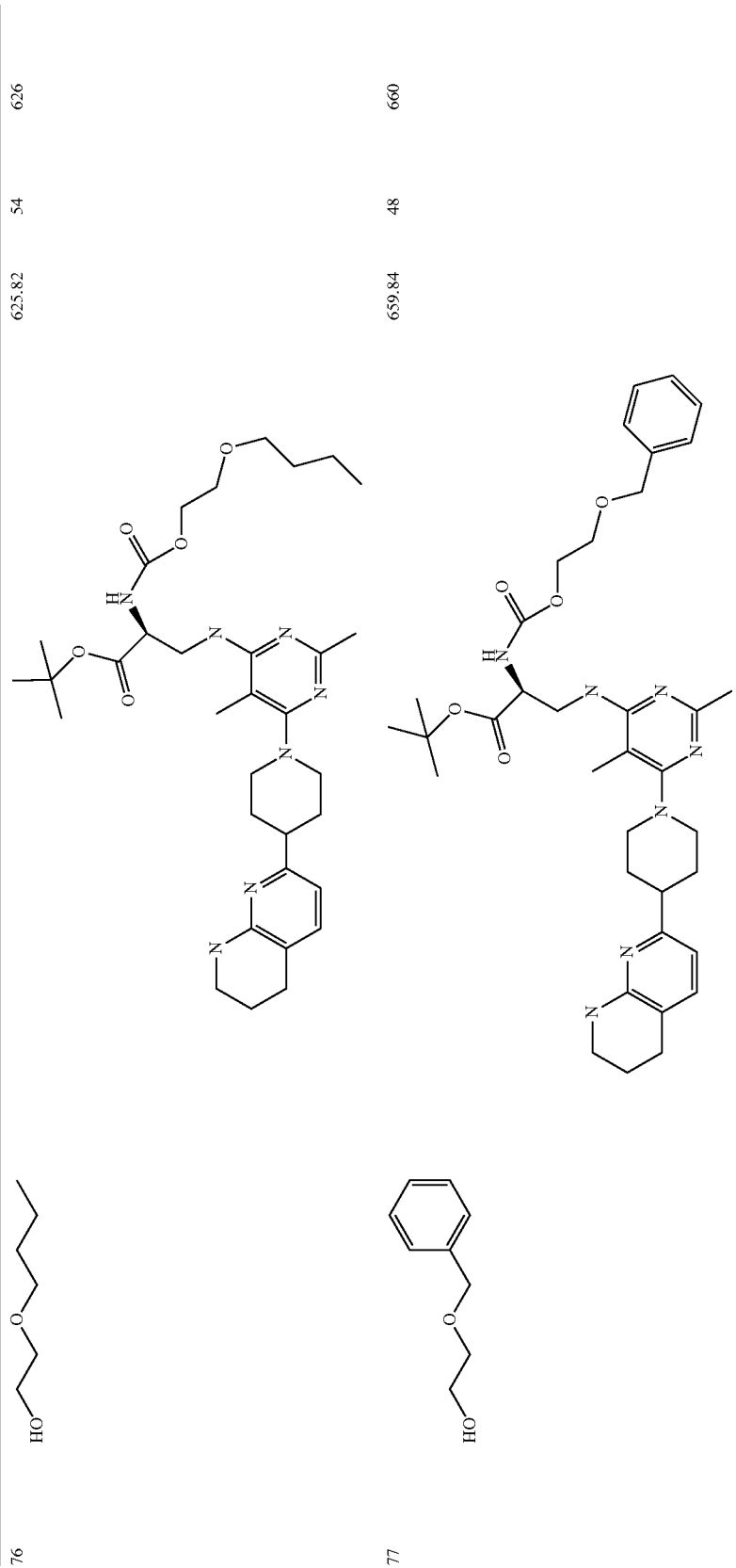

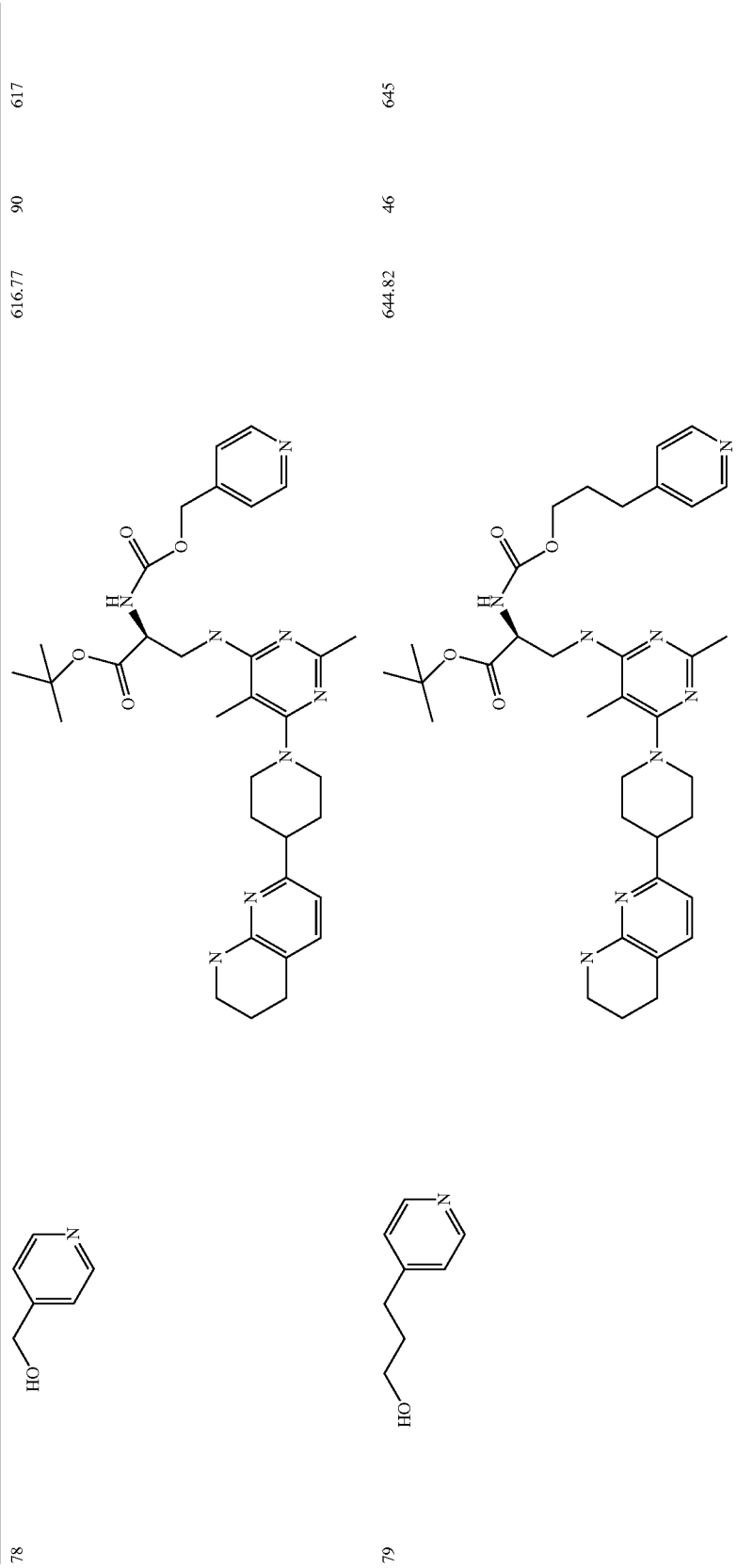

| Example | Starting ester | m_C (mg) | Expected acid | m_D (mg) | FW free base | MS [M/Z + H]+ |
|---|---|---|---|---|---|---|
| 68 | [structure] | 250 | [structure] nCF₃COOH | 210 | 575.69 | 576 |

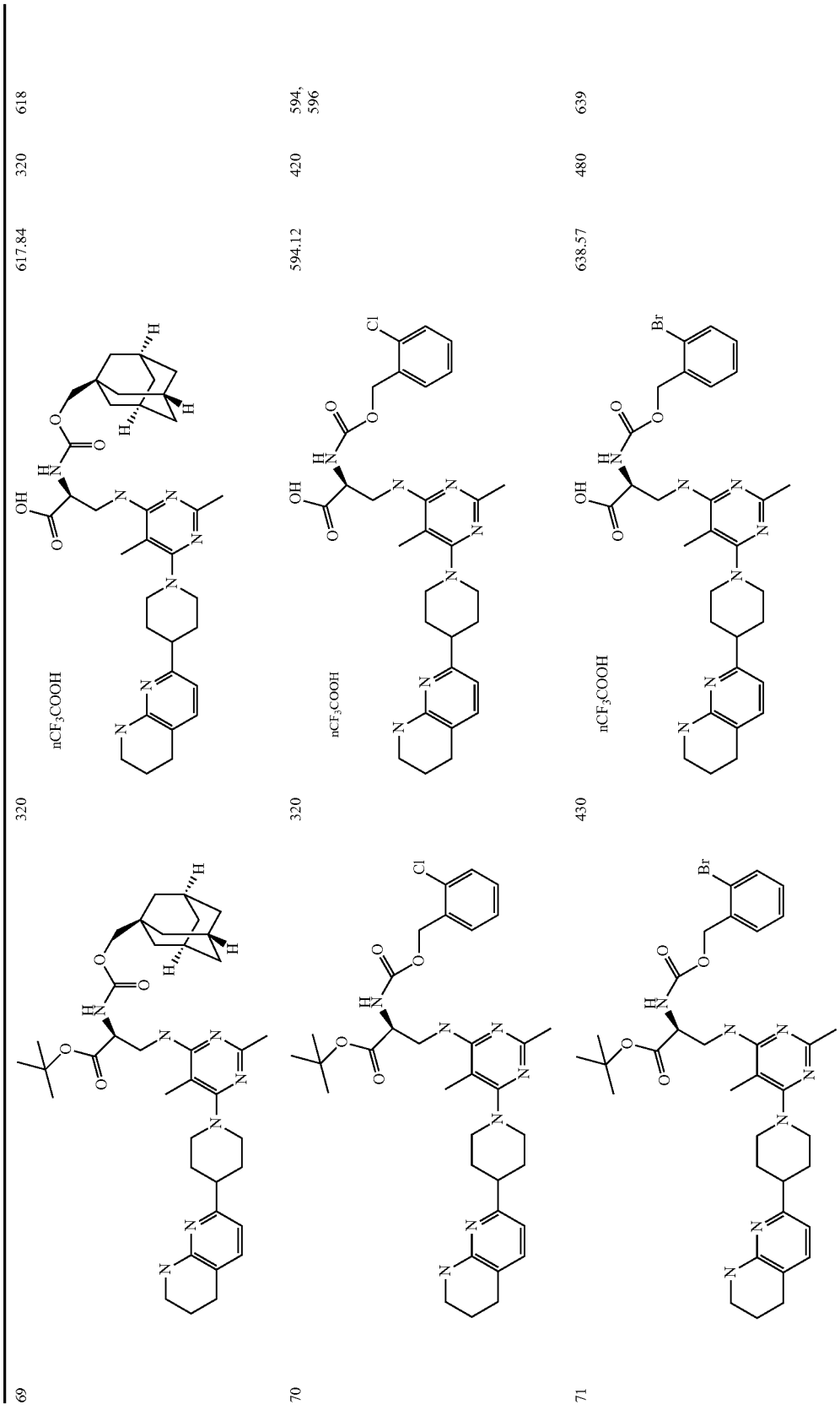

| Example | Starting ester | m_C (mg) | | m_D (mg) | FW (free base) | MS [M/Z+H]+ |
|---|---|---|---|---|---|---|
| 72 | [cyclohexyl-ethyl carbamate tert-butyl ester with pyrimidine-piperidine-tetrahydronaphthyridine], nCF₃COOH | 330 | [corresponding free acid], nCF₃COOH | 579.75 | 450 | 580 |
| 73 | [naphthyl-ethyl carbamate tert-butyl ester with pyrimidine-piperidine-tetrahydronaphthyridine], nCF₃COOH | 410 | [corresponding free acid], nCF₃COOH | 623.76 | 510 | 624 |
| 74 | [cyclopropylmethyl carbamate tert-butyl ester with pyrimidine-piperidine-tetrahydronaphthyridine], nCF₃COOH | 390 | Expected acid, nCF₃COOH | 523.64 | 610 | 524 |

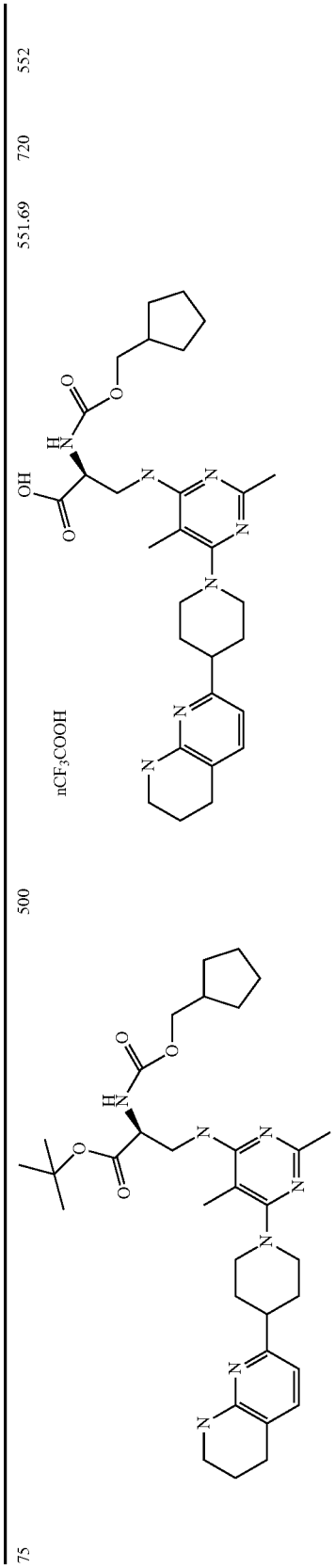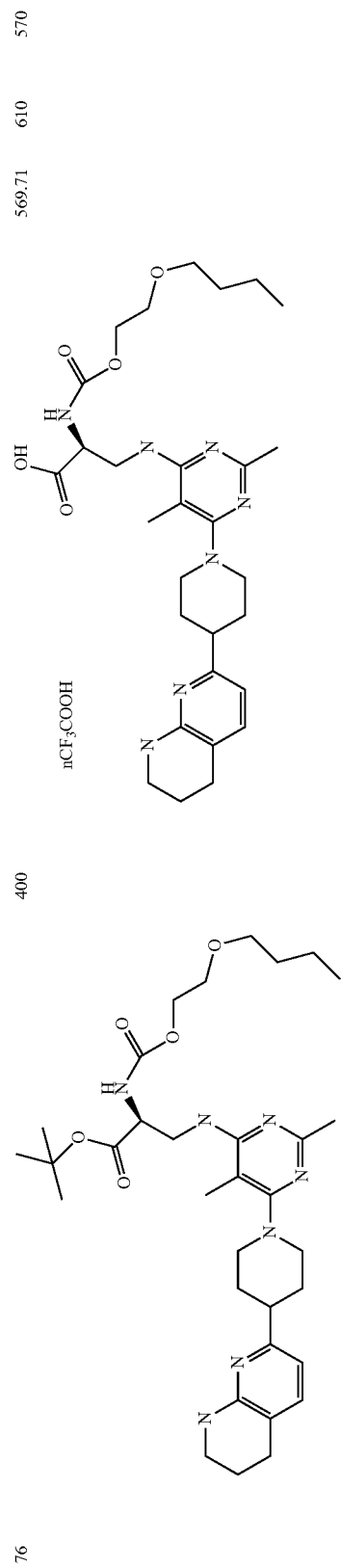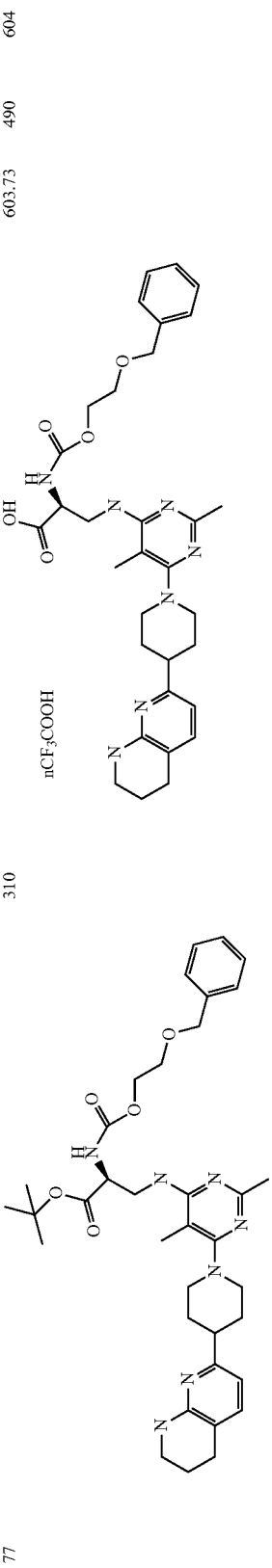

| | | | | | |
|---|---|---|---|---|---|
| 78 | 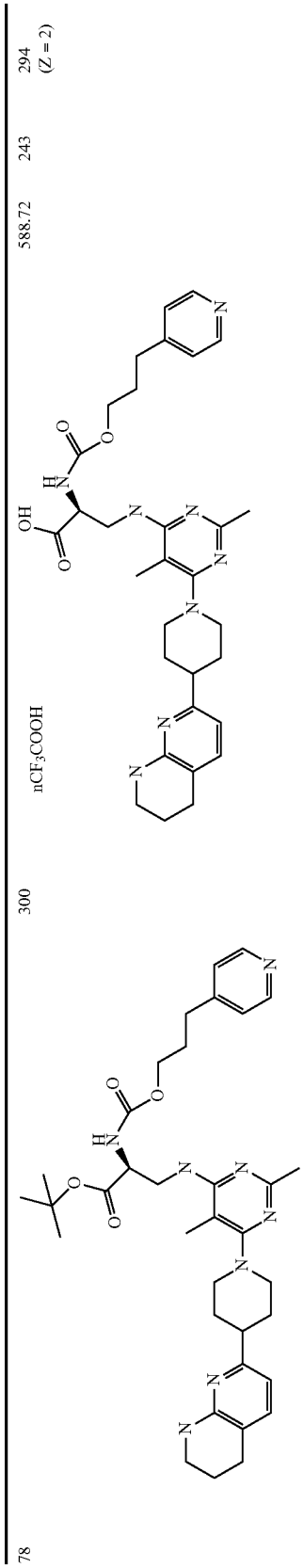 | 300 | 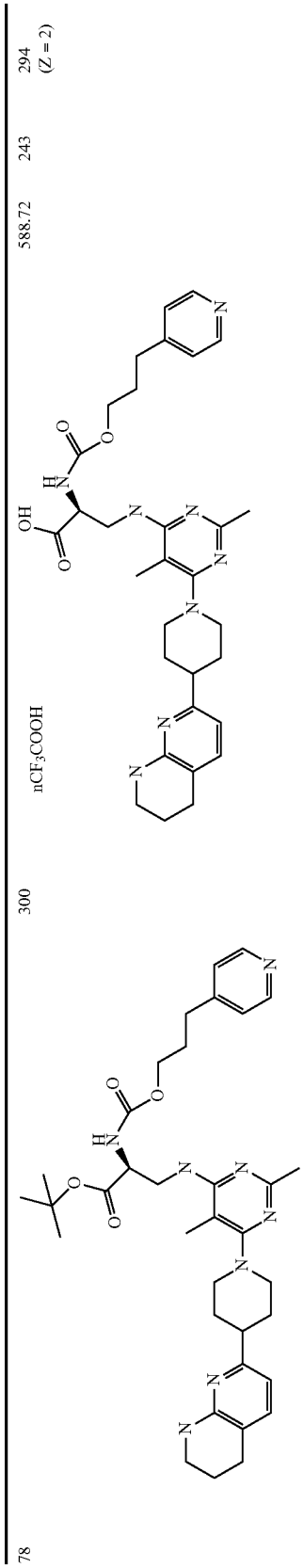 | 588.72 243 | 294 (Z = 2) |
| 79 | 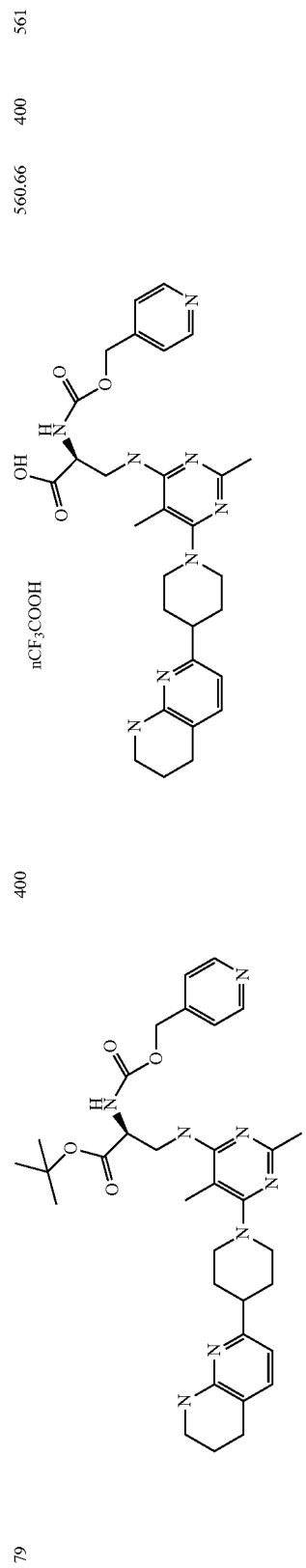 | 400 | 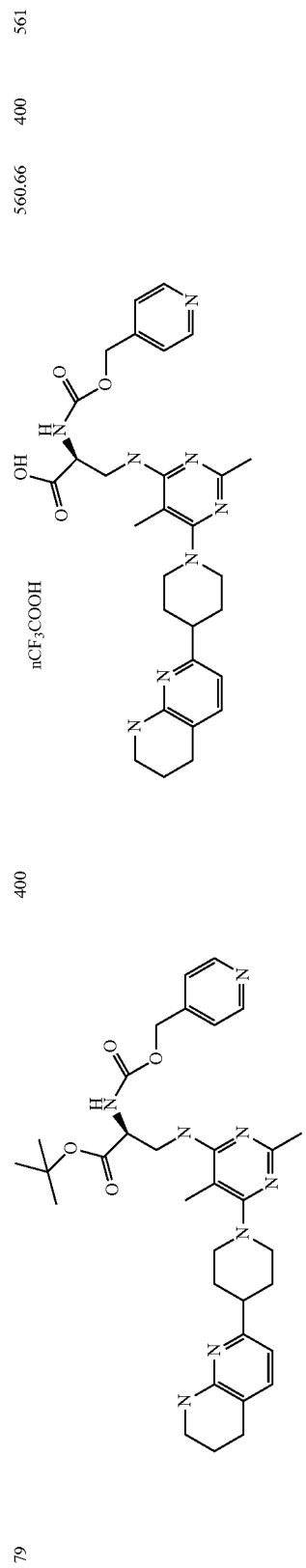 | 560.66 400 | 561 |
| 80 | 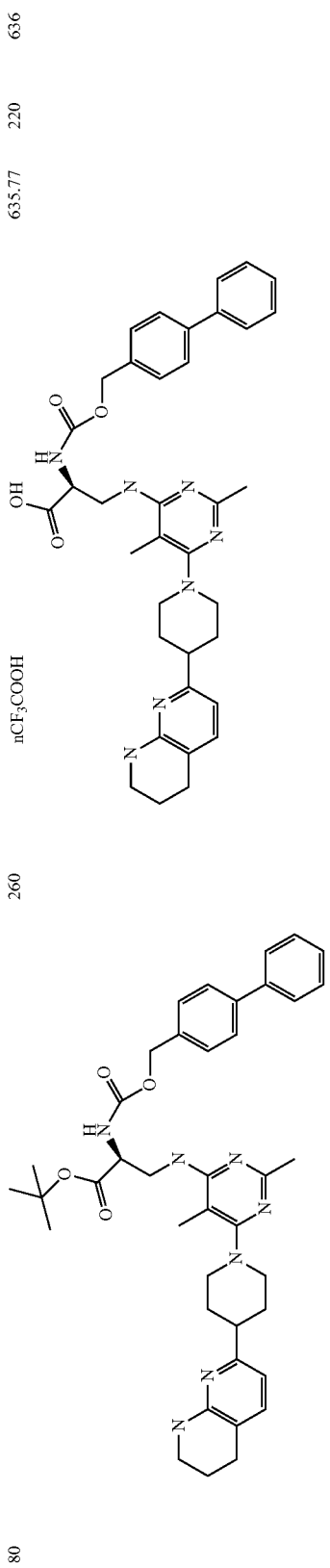 | 260 | 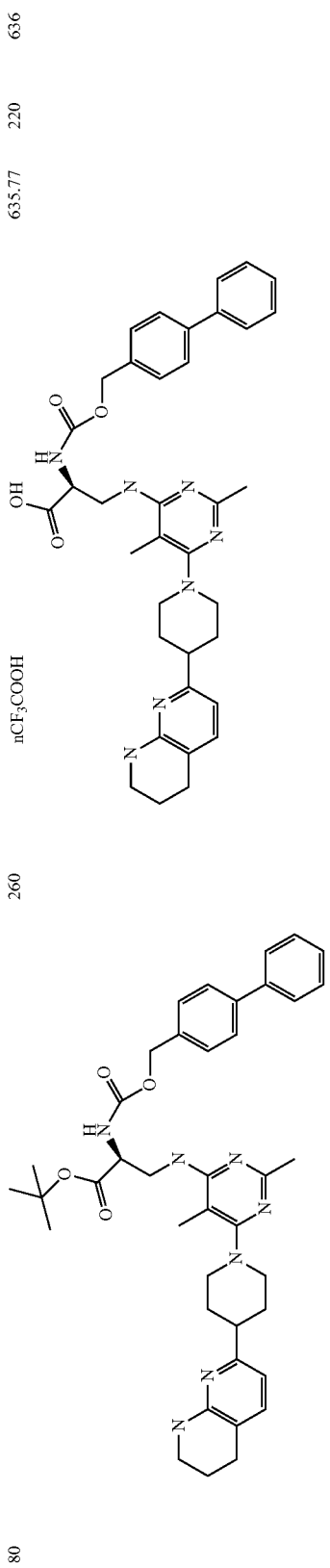 | 635.77 220 | 636 |

Example 81

Synthesis of the tert-butyl ester of 2-cyclohexyl-methoxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid

Stage a

Synthesis of the activated alcohol N-succinimidyl carbonic acid cyclohexylmethyl ester 5.38 g (10.5 mmoles) of di(N-succinimidyl)carbonate is solubilized in 60 ml of methylene chloride. 2.16 ml (17.55 mmoles) of cyclohexylmethanol solubilized in 10 ml of methylene chloride and 4.92 ml (35.1 mmoles) of triethylamine are added at ambient temperature. The reaction mixture is left under stirring overnight.

Then, the reaction mixture is concentrated to dryness before extraction with ethyl acetate and washing with a saturated solution of sodium bicarbonate. The organic phase obtained is dried over magnesium sulphate before being concentrated to dryness under reduced pressure (2 kPa). 4.4 g of activated alcohol is obtained which is used as it is in the following stage. (quantitative yield)

TLC: Rf=0.84 (silica gel, eluent: ethyl acetate-triethylamine (90-10).

1H-NMR (CDCl3): δ 1.02 (m, 2H, CH2-CH2-CH2-CH2-CH2); 1.25 (m, 4H, CH2-CH2-CH2-CH2-CH2); 1.75 (m, 5H, CH2-CH2-CH—CH2-CH2 and CH2-CH2-CH—CH2-CH2); 2.85 (s, 4H, CO—CH2-CH2-CO); 4.15 (d, 2H, OCOO—CH2-cyclohexyl)

Stage b 8.8 g (17 mmoles) of 2-amino-3-{2,5-dimethyl-6-[4-(5,6,7,8-tetrahydro-[1,8]naphthy-ridin-2-yl)-piperidin-1-yl]-pyrimidin-4-ylamino}-propionic acid ter-butyl ester, as well as 2.47 ml (17 mmoles) of triethylamine are added to 4.35 g (17 mmoles) of activated alcohol in solution in 250 ml of methylene chloride.

The mixture is left under stirring overnight at ambient temperature.

The reaction mixture is then extracted with ethyl acetate after washing with a saturated solution of sodium bicarbonate. The organic phase obtained is dried over magnesium sulphate before being concentrated to dryness under reduced pressure (2 kPa). The residue obtained is then chromatographed on silica gel with the following eluent: ethyl acetate/heptane to 100% ethyl acetate. 6.9 g of expected product is obtained. (yield=65%)

TLC: (eluent: ethyl acetate-dichloromethane 50-50 on alumina, and ethyl acetate-heptane 80-20 on silica)

TLC: Rf=0.23 (eluent: ethyl acetate-heptane (60/40)

1H-NMR (MeOD): δ 0.23 (m, 2H, CH2-CH2-CH2-CH2-CH2); 0.5 (m, 4H, CH2-CH2-CH2-CH2-CH2); 0.65 (s, 9H, tBu); 0.82 (m, 1H, CH2-CH2-CH—CH2-CH2); 0.95 (m, 4H, CH2-CH2-CH—CH2-CH2); 1.1 (m, 6H, N—CH2-CH2-CH—CH2-CH2, CH2-CH2-CH2-NH); 1.2 (s, 3H, CH3-); 1.62 (s, 3H, N=C(CH3)-N); 1.82 (m, 1H, N—CH2-CH2-CH—CH2-CH2); 1.95 (t, 2H, CH2-CH2-CH2-NH); 2.65 (m, 2H, CH2-CH2-CH2-NH); 2.12 and 2.85 (2m, 4H, N—CH2-CH2-CH—CH2-CH2); 3.05 (m, 2H, NH—CH2-CH=NH, 2H, NH—CO—CH2-cyclohexyl); 3.5 (m, 1H, NH—CH2-CH—NH); 5.65 and 6.4 (2d, 2H, CH=CH naphthyridine)

MS: 622 (MH)+, 283 (MH-tBu)2+, 426 (MH-tBu-COO-cyclohexyl)+

Example 82

Synthesis of the hydrochloride of 2-cyclohexyl-methoxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid 28 g (0.045 moles) of 2-cyclohexylmethoxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid tert-butyl ester in 76 ml of a 6N solution of hydrochloric acid in water is stirred at ambient temperature for 20 hours.

The reaction mixture is concentrated to dryness under reduced pressure (2 kPa) in the presence of toluene and isopropanol successively.

The residue obtained is solubilized in the minimum amount of dichloromethane then poured into ethyl ether. The precipitate formed is filtered, washed with ether then with pentane and dried under vacuum. 29 g of a white powder is obtained.

TLC: Rf=0.24 (silica gel, eluent: dichloromethane-methanol-water-acetic acid 90-10-1-1).

1H-NMR (CDCl3): δ 0.93 (m, 2H, CH2-CH2-CH2-CH2-CH2); 1.25 (m, 4H, CH2-CH2-CH2-CH2-CH2); 1.6 (m, 1H, CH2-CH2-CH—CH2-CH2); 1.7 (m, 4H, CH2-CH2-CH—CH2-CH2); 1.1 (m, 9H, N—CH2-CH2-CH—CH2-CH2, CH2-CH2-CH2-NH, CH3-); 2.55 (s, 3H, N=C(CH3)-N); 2.77 (m, 1H, N—CH2-CH2-CH—CH2-CH2); 2.97 (t, 2H, CH2-CH2-CH2-NH); 2.52 and 3.97 (2m, 4H, N—CH2-CH2-CH—CH2-CH2); 3.5 (m, 2H, CH2-CH2-CH2-NH); 3.7 and 3.97 (2m, 2H, NH—CH2-CH—NH); 3.87 (m, 2H, NH—CO—CH2-cyclohexyl); 4.35 (m, 1H, NH—CH2-CH—NH); 6.3 (m, 1H, mobile NH); 6.4 and 7.37 (2d, 2H, CH=CH naphthyridine); 10.15 (m, 1H, mobile COOH).

MS: 566(MH)+; 283(MH)2+; 564(MH)−; 426(MH-COO-cyclohexyl)+

Example 83

Synthesis of the hydrochloride of 2-cyclohexyl-methoxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid tert-butyl ester 27.2 g (43.8 mmoles) of 2-cyclohexylmethoxycarbonylamino-3-{2,5-dimethyl-6-[4-(5,6,7,8-tetrahydro-[1,8]naphthyridin-2-yl)-piperidin-1-yl]-pyrimidin-4-ylamino}-propionic acid tert-butyl ester in 240 ml of a 50/50 mixture of dichloromethane and ethyl ether is stirred, then a mixture comprising 21.9 ml of 2N hydrochloric acid in ether and 20 ml of ethyl ether is slowly added.

The reaction mixture must remain clear during the addition.

The solvent is then partially evaporated off under reduced pressure (2 kPa), the solution containing a minimum amount of solvent is poured into 1 liter of isopropyl ether then into 500 ml of pentane, the precipitate formed is filtered then dried under vacuum.

28.5 g of a white powder is obtained.

1H-NMR (CDCl$_3$): δ 0.95 (m, 2H, CH2-CH2-CH2-CH2-CH2); 1.23 (m, 4H, CH2-CH2-CH2-CH2-CH2); 1.47 (s, 9H, tBu); 1.67 (m, 5H, CH2-CH2-CH—CH2-CH2,

CH2-CH2-CH—CH2-CH2); 2.02 (m, 9H, N—CH2-CH2-CH—CH2-CH2, CH2-CH2-CH2-NH, CH3-); 2.65 and 3.75 (2m, 4H, N—CH2-CH2-CH—CH2-CH2); 2.77 (t, 2H, CH2-CH2-CH2-NH); 2.95 (m, 1H, N—CH2-CH2-CH—CH2-CH2); 3.52 (m, 2H, CH2-CH2-CH2-NH); 3.8 (m, 2H, NH—CH2-CH—NH, 2H, NH—CO—CH2-cyclohexyl); 4.4 (m, 1H, NH—CH2-CH—NH); 6.47 and 7.37 (2d, 2H, CH=CH naphthyridine); 8.8 (m, 1H, mobile NH)

MS: 622(MH)+, 283(MH-tBu)2+>>

Pharmacological test: Kistrin/Vitronectin Receptor ($\alpha_v\beta_3$) ELISA test Protocol:

96-well MaxiSorp plates are coated overnight at 40° C. with 100 μl of Kistrin at 1 μg/ml (dilution in coating buffer: 0.05 M carbonate/NaOH pH 9.6). The next day, the wells are emptied and the ligands (kistrin) are then fixed (fixation buffers: PBS containing 0.5% BSA (pH=7.4)) for 1 hour at ambient temperature under gentle stirring at 125 rpm. The wells are washed six times (washing buffer: PBS containing 0.05% Tween 20 (pH 7.7) then the following are added per well and in this order:

40 μl of incubation buffer

10 μl of the dilution of the product to be tested (the products are diluted in a 50:50 DMSO/water mixture)

50 μl of human $\alpha_v\beta_3$ receptor (cf Pytella et al. Methods Enzymol. (1987) 144 (Dilution in incubation buffer, adapted according to the batch of receptor and according to the ligand). The ligand, the $\alpha_v\beta_3$ receptor and the products to be studied are co-incubated for 3 hours at ambient temperature with gentle stirring at 125 rpm.

The wells are again washed six times, then incubated for 2 hours at ambient temperature with gentle stirring at 125 rpm, in the presence of 100 μl of anti-receptor antibody coupled to a peroxidase (The 4B12-HRP antibody is diluted in incubation buffer (50 mM TRIS pH 7.4; 0.5% BSA; 0.05% Tween 20; 1 mM $MnCl_2$; 50 μM $CaCl_2$; 50 μM $MgCl_2$; 100 mM NaCl). The dilution is to be adapted according to the batch of receptor.

The wells are then washed six times before measurement of the ligand-receptor bond is carried out using a peroxidase developer kit (TBM Microwell Peroxidase Substrate System Kirkegaard; Ref cat 50-76-00).

This kit contains a flask A of substrate (3,3',5,5'-tetramethylebenzidine at 0.4 g/l) and a flask B (0.02% $H_2O_2$ in Citrate/Citric acid). Extemporaneously, one volume of A is mixed with one volume of B, then the reaction mixture is distributed at a rate of 100 μl/well.

The enzymatic reaction develops between 6 to 10 minutes for Kistrin/$\alpha_v\beta_3$ then its development is stopped by the addition of 100 μl of 1M phosphoric acid. The optical density is determined at 450 nm.

Expression of the Results

The following curve is plotted: the bond percentage as a function of the logarithm of each concentration of the tested product.

For each product the IC50 is determined according to the following formula:

IC50=($B$0+$B$min)/2

B0=Maximum bond in the absence of any product

Bmin=Minimum bond in the presence of the highest concentration of the product.

| EXAMPLE | K/VnR IC$_{50}$ (nM) |
|---------|----------------------|
| 1 to 65 | 2 to 10000 |

Activity In Vivo

Hypercalcemia induced by the parathyroid hormone (PTH) in a thyroparathyroidectomized (TPXT) rat model Stimulation of bone resorption is induced in TPXT rats by perfusion of PTH and the variations of bone resorption are monitored by the concentration of calcium in the serum.

Male Sprague Dawley rats weighing 150-200 g are thyroparathyroidectomized. The rats are subjected to a standard diet containing 7 g Ca/kg (UAR) and Volvic water. The effectiveness of the thyroparathyroidectomy is tested by measuring the concentrations of Ca in the serum 8 days after the operation in animals which have been starved since the previous day. The rats are considered as thyroparathyroidectomized when the Ca levels in the serum are less than 80 mg/l. The PTH (1-34) of the rat (Bachem) is dissolved in 0.15M of NaCl Cys.HCl 2% and delivered by osmotic minipumps (ALZET 2001D) at a dose of 200 pmol/kg/h. The minipumps are introduced into the intraperitoneal cavities under anaesthesia (ketamine—75 mg/kg and acepromazine—2.5 mg/kg) of the TPXT rats which have been starved since the previous day. The control TPXT rats receive the minipumps filled with the PTH vehicle.

Either the product to be tested or the vehicle (controls and rats treated with the PTH) are administered twice by subcutaneous route (2 ml/kg of body weight) at time 0 and 3 hours after the start of the infusion of PTH. The test is continued for the next 6 hours. At the end of the treatment, all the blood is collected after decapitation. The blood samples are centrifuged at 3000 rpm for 15 minutes (CR422 Jouan) in order to obtain the serum.

The total concentrations of Ca in the serum are measured by colorimetry (Ciba-Corning) using an IEMS Labsystems microplate reading system, at 540 nm.

The difference between the average calcemia values of the treated rats and the control groups is analyzed by variance and by Dunnett's test.

The activity of a product is calculated by the following formula:

$$\% \text{ effect} = \frac{\text{Calcemia (product)} - \text{calcemia }(PTH)}{\text{Calcemia }(PTH) - \text{calcemia (control)}} \times 100$$

The products according to the invention tested by the method described were shown to be active at doses ranging from twice 1 mg/kg to twice 10 mg/kg by subcutaneous route and at doses ranging from twice 3 mg/kg to twice 30 mg/kg by oral route in the rat.

What is claimed:

1. A method for the treatment of osteoporosis, said method comprising administering to a subject in need thereof, an effective amount of a pyrimidine compound of general formula (I):

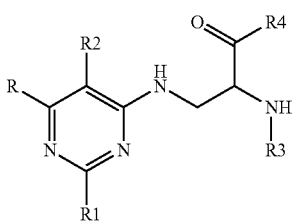

(I)

stereoisomeric forms thereof in the pure state and mixtures of these stereoisomers, and if appropriate, the pure E isomers, the pure Z isomers and the E/Z mixtures, as well as physiologically acceptable addition salts thereof, solvates thereof and prodrugs thereof, wherein I)
— R represents:
an —X-alk-Het radical, wherein X is an oxygen or sulphur atom or an —NR'— radical, wherein R' is a hydrogen atom or a linear or branched alkyl radical containing 1 to 4 carbon atoms, alk represents a linear or branched alkyl radical containing 1 to 4 carbon atoms and Het represents a monocyclic or polycyclic system, each ring being constituted by 4 to 10 aromatic or non-aromatic members, and being able to contain 1 to 4 heteroatoms selected from nitrogen, oxygen or sulphur and being able to be itself substituted by one or more $R^o$ groups defined hereafter, or a radical:

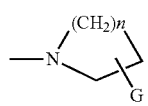

(Ia)

wherein G represents an aromatic or non-aromatic, monocyclic or polycyclic heterocyclyl radical comprising 5 to 10 members, and wherein at least one of the rings contains 1 to 4 nitrogen atoms, said heterocyclyl radical being able to be itself optionally substituted by a ($C_1$-$C_8$) alkylamino radical the alkyl part of which in linear or branched chain can be substituted by a phenyl or heterocyclyl radical with 5 or 6 members containing 1 to 4 heteroatoms selected from nitrogen, oxygen or sulphur, and n represents 1 or 2, or
a radical:

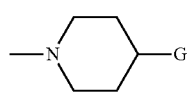

(Ib)

wherein G represents an aromatic monocyclic heterocyclyl radical with 5 or 6 members containing 1 to 4 nitrogen atoms and substituted by an alkyl($C_1$-$C_6$) amino radical the alkyl radical of which can itself be substituted by a phenyl or aromatic monocyclic hetero-cyclyl radical with 5 or 6 members, containing a heteroatom selected from nitrogen, oxygen or sulphur;
— $R^1$ represents a hydrogen atom; a ($C_5$-$C_{14}$)-aryl; ($C_5$-$C_{14}$)-aryl-($C_1$-$C_4$)-alkyl- group; an amino radical non-substituted, monosubstituted or disubstituted by an alkyl radical and/or an acyl radical containing 1 to 4 carbon atoms;
— $R^2$ represents a hydrogen atom; a halogen atom; a nitro group; an alkyl radical containing 1 to 4 carbon atoms; an amino radical non-substituted or monosubstituted or disubstituted by an alkyl radical and/or an acyl radical containing 1 to 4 carbon atoms; a —$(CH_2)_{0-2}$—$CO_2R^5$ group; or a —$(CH_2)_{0-2}$—$OR^5$ group;
— $R^3$ represents:
a hydrogen atom,
a —$CO_2R^5$ radical,
an —$SO_2R^5$ radical, or
a monocyclic or polycyclic system, each ring being constituted by 4 to 10 aromatic or non-aromatic members, the ring or at least one of the rings containing 1 to 4 heteroatoms selected from N, O or S, substituted or non-substituted by one or more $R^o$ radicals,
— $R^4$ represents OH; ($C_1$-$C_8$)-alkoxy-; ($C_5$-$C_{14}$)-aryl-($C_1$-$C_4$)-alkyloxy-; ($C_5$-$C_{14}$)-aryloxy-; ($C_3$-$C_{12}$)-cycloalkyloxy; ($C_3$-$C_{12}$)-cycloalkyl-($C_1$-$C_4$)-alkyloxy-; ($C_1$-$C_8$)-alkylcarbonyloxy-($C_1$-$C_4$)-alkyloxy-; ($C_5$-$C_{14}$)-aryl-($C_1$-$C_4$)-alkylcarbonyloxy-($C_1$-$C_4$) alkyloxy-; ($C_1$-$C_8$) dialkylaminocarbonylmethyloxy-; ($C_5$-$C_{14}$)-aryl-($C_1$-$C_4$)-dialkylaminocarbonylmethyloxy-; an amino radical non-substituted or monosubstituted or disubstituted by a ($C_1$-$C_4$)-alkyl and/or ($C_5$-$C_{14}$)-aryl and/or ($C_5$-$C_{14}$)-aryl-($C_1$-$C_4$)-alkyl- radical and/or a ($C_1$-$C_5$)-acyl radical; or the remainder of a D or L amino acid;
— $R^5$ represents ($C_1$-$C_8$)-alkyl; ($C_5$-$C_{14}$)-aryl; ($C_5$-$C_{14}$)-aryl-($C_1$-$C_4$)-alkyl-; ($C_3$-$C_{12}$)-cycloalkyl or ($C_3$-$C_{12}$)-cycloalkyl-($C_1$-$C_4$)-alkyl-, bicycloalkyl-($C_1$-$C_4$)-alkyl-, tricycloalkyl-($C_1$-$C_4$)-alkyl-, said aryl, alkyl, cycloalkyl, bicycloalkyl and tricycloalkyl radicals being non-substituted or substituted by one or more $R^o$ groups; and
$R^o$ represents halogen; amino; nitro; hydroxyl, ($C_1$-$C_4$)-alkyloxy-; ($C_1$-$C_4$)-alkylthio-; ($C_1$-$C_4$)-alkylsulphonyl-; carboxy; ($C_1$-$C_4$)-alkyloxycarbonyl-; ($C_1$-$C_8$)-alkyl non-substituted or substituted by one or more halogen atoms, ($C_5$-$C_{14}$)-aryl, ($C_5$-$C_{14}$)-aryl-($C_1$-$C_4$)-alkyl-; ($C_5$-$C_{14}$)-aryl-($C_1$-$C_4$)-alkyloxy- or ($C_5$-$C_{14}$)-heterocyclyl, or II)
— R represents a radical:

(Ib)

wherein G is selected from the following radicals:
Het-NH—CO—,
Het-NH—$CH_2$—, or
Het-,
wherein Het represents a monocylcic or polycyclic system, each ring being constituted by 4 to 10 aromatic or non-aromatic members, the ring or at least one of the rings containing 1 to 4 nitrogen atom, and being able to itself be substituted or non-substituted by one or more $R^o$ groups;
— $R^1$ represents an alkyl radical containing 1 to 4 carbon atoms in linear or branched chain; a cycloalkyl radical containing 3 to 6 carbon atoms; or an alkyloxy or alkylthio radical the alkyl part of which contains 1 to 4 carbon atoms in linear or branched chain;

—$R^2$, —$R^3$, —$R^4$, and —$R^5$ are defined as previously in I);
—$R^o$ is defined as previously in I); or III)
- —R is defined as previously in II);
- —$R^1$, —$R^3$, —$R^4$, and —$R^5$ are defined as previously in I);
- —$R^2$ represents a hydroxymethyl radical, a formyl radical or a disubstituted amino radical the substituents of which form together with the nitrogen atom to which they are attached, a saturated or unsaturated heterocycle containing 4 to 6 members; and
- —$R^o$ is defined as previously in I); or IV)
- —R is defined as previously in II);
- —$R^1$, —$R^2$, and —$R^4$ are defined as previously in I);
- —$R^3$ represents:
    - a linear or branched ($C_1$-$C_4$) alkyl or ($C_2$-$C_4$) alkenyl radical, optionally substituted by an aryl or mono or polycyclic heterocyclyl radical with 4 to 10 members, themselves being able to be substituted by one or more radicals chosen from hydroxy, ($C_1$-$C_4$) alkyloxy, amino, ($C_1$-$C_4$) alkylamino, ($C_1$-$C_4$)-dialkylamino, phenyl, cyanophenyl or monocyclic heterocyclyl containing 1 to 4 heteroatoms selected from nitrogen, oxygen or sulphur;
    - a —$CO_2R^5$ radical,
        - wherein $R^5$ is substituted and represents ($C_1$-$C_8$)-alkyl; ($C_5$-$C_{14}$)-aryl; ($C_5$-$C_{14}$)-aryl-($C_1$-$C_4$)-alkyl-; ($C_3$-$C_{12}$)-cyclo-alkyl or ($C_3$-$C_{14}$)-cycloalkyl-($C_1$-$C_4$)-alkyl-, bicycloalkyl-($C_1$-$C_4$)-alkyl-, tricycloalkyl-($C_1$-$C_4$)-alkyl-, the said aryl, alkyl, cycloalkyl, bicycloalkyl and tricycloalkyl radicals being substituted by one or more groups chosen from ($C_1$-$C_4$)-alkylsulphonyl-; ($C_5$-$C_{14}$)-aryl-($C_1$-$C_4$)-alkyloxy- or ($C_5$-$C_{14}$)-heterocyclyl, or
    - a —$COR'^5$ radical,
    - an —$SO_2R''^5$ radical, wherein
        - —$R'^5$ represents:
            - ($C_1$-$C_8$)-alkyl substituted by a radical as defined for $R^5$ or by a ($C_5$-$C_{14}$) aryloxy radical, the aryl or cycloalkyl radicals themselves being able to be substituted by one or more $R^o$ radicals; or
            - a cycloalkyl, aryl or mono or polycyclic heterocyclyl radical optionally substituted by trifluoromethylalkyloxy or ($C_1$-$C_{10}$)-aryl radicals; or
            - ($C_1$-$C_4$) alkylamino; ($C_3$-$C_8$) cycloalkylamino; arylamino or hetero-cyclylamino the aryl or heterocyclyl part of which are mono or polycyclic, these $R'^5$ radicals being able themselves to be substituted by a halogen atom, a nitro, amino, ($C_1$-$C_4$) alkyloxy, ($C_1$-$C_4$) alkyloxycarbonyl, aryl or arylalkyl radical the alkyl part of which contains 1 to 4 carbon atoms in linear or branched chain; and
        - —$R''^5$ represents a ($C_1$-$C_4$) alkylamino or di($C_1$-$C_4$) alkylamino radical the alkyl parts of which can together form a heterocycle with 5 to 7 members, with the nitrogen atom to which they are linked, an arylamino, aralkyl($C_1$-$C_4$) amino or heteroaralkyl ($C_1$-$C_4$) amino radical the aryl or heteroaryl radical of which is mono or polycyclic and comprises 5 to 10 members, the heteroaryl radical being able to contain 1 to 4 heteroatoms chosen from nitrogen, oxygen or sulphur; and
- —$R^o$ is defined as previously in I); or V)
- —R, —$R^2$, —$R^3$ and —$R^4$ are defined as previously in I);
- —$R^1$ is defined as previously in II); or VI)
- —R, —$R^1$, —$R^3$ and —$R^4$ are defined as previously in II);
- —$R^2$ is defined as previously in III); or VII)
- —R, —$R^1$ and —$R^2$ are defined as previously in I);
- —$R^4$ is defined as previously in I); and
- —$R^3$ is defined as previously in IV); or VIII)
- —R, —$R^1$ and —$R^2$ are defined as previously in II);
- —$R^4$ is defined as previously in I); and
- —$R^3$ is defined as previously in IV); or IX)
- —R and —$R^3$ are defined as previously in I);
- —$R^4$ is defined as previously in I);
- —$R^1$ is defined as previously in II); and
- —$R^2$ is defined as previously in III); or X)
- —R and —$R^2$ are defined as previously in I);
- —$R^4$ is defined as previously in I);
- —$R^1$ is defined as previously in II); and
- —$R^3$ is defined as previously in IV); or XI)
- —R and —$R^1$ are defined as previously in II);
- —$R^4$ is defined as previously in I);
- —$R^2$ is defined as previously in III); and
- —$R^3$ is defined as previously in IV); or XII)
- —R and —$R^4$ are defined as previously in I);
- —$R^1$ is defined as previously in II);
- —$R^2$ is defined as previously in III);
- —$R^3$ is defined as previously in IV);

with the proviso that the above radicals cannot simultaneously have the meaning:
- —R represents a radical (Ib) in which G is 1,2,3,4-tetrahydro-1,8-naphthyridin-7-yl,
- —$R^1$ represents methyl,
- —$R^2$ represents methyl,
- —$R^3$ represents benzyloxycarbonyl, and
- —$R^4$ represents OH or t-butoxy.

2. A method for the treatment of, restenosis, arteriosclerosis, nephropathies or retinopathies, said method comprising administering to a subject in need thereof, an effective amount of a pyrimidine compound of general formula (I):

(I)

stereoisomeric forms thereof in the pure state and mixtures of these stereoisomers, and if appropriate, the pure E isomers, the pure Z isomers and the E/Z mixtures, as well as physiologically acceptable addition salts thereof, solvates thereof and prodrugs thereof, wherein I)
- —R represents:
    - an —X-alk-Het radical, wherein X is an oxygen or sulphur atom or an —NR'— radical, wherein R' is a hydrogen atom or a linear or branched alkyl radical containing 1 to 4 carbon atoms, alk represents a linear or branched alkyl radical containing 1 to 4 carbon atoms and Het represents a monocyclic or polycyclic system, each ring being constituted by 4 to 10 aromatic or non-aromatic members, and being able to contain 1 to 4 heteroatoms selected from nitrogen, oxygen or sulphur and being able to be itself substituted by one or more $R^o$ groups defined hereafter, or a radical:

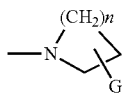
(Ia)

wherein G represents an aromatic or non-aromatic, monocyclic or polycyclic heterocyclyl radical comprising 5 to 10 members, and wherein at least one of the rings contains 1 to 4 nitrogen atoms, said heterocyclyl radical being able to be itself optionally substituted by a $(C_1-C_8)$ alkylamino radical the alkyl part of which in linear or branched chain can be substituted by a phenyl or heterocyclyl radical with 5 or 6 members containing 1 to 4 heteroatoms selected from nitrogen, oxygen or sulphur, and n represents 1 or 2, or
a radical:

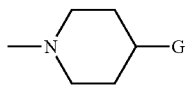
(Ib)

wherein G represents an aromatic monocyclic heterocyclyl radical with 5 or 6 members containing 1 to 4 nitrogen atoms and substituted by an alkyl$(C_1-C_6)$ amino radical the alkyl radical of which can itself be substituted by a phenyl or aromatic monocyclic hetero-cyclyl radical with 5 or 6 members, containing a heteroatom selected from nitrogen, oxygen or sulphur;
—$R^1$ represents a hydrogen atom; a $(C_5-C_{14})$-aryl; $(C_5-C_{14})$-aryl-$(C_1-C_4)$-alkyl- group; an amino radical non-substituted, monosubstituted or disubstituted by an alkyl radical and/or an acyl radical containing 1 to 4 carbon atoms;
—$R^2$ represents a hydrogen atom; a halogen atom; a nitro group; an alkyl radical containing 1 to 4 carbon atoms; an amino radical non-substituted or monosubstituted or disubstituted by an alkyl radical and/or an acyl radical containing 1 to 4 carbon atoms; a —$(CH_2)_{0-2}$—$CO_2R^5$ group; or a —$(CH_2)_{0-2}$—$OR^5$ group;
—$R^3$ represents:
a hydrogen atom,
a —$CO_2R^5$ radical,
an —$SO_2R^5$ radical, or
a monocyclic or polycyclic system, each ring being constituted by 4 to 10 aromatic or non-aromatic members, the ring or at least one of the rings containing 1 to 4 heteroatoms selected from N, O or S, substituted or non-substituted by one or more $R^o$ radicals,
—$R^4$ represents OH; $(C_1-C_8)$-alkoxy-; $(C_5-C_{14})$-aryl-$(C_1-C_4)$-alkyloxy-; $(C_5-C_{14})$-aryloxy-; $(C_3-C_{12})$-cycloalkyloxy; $(C_3-C_{12})$-cycloalkyl-$(C_1-C_4)$-alkyloxy-; $(C_1-C_8)$-alkylcarbonyloxy-$(C_1-C_4)$-alkyloxy-; $(C_5-C_{14})$-aryl-$(C_1-C_4)$-alkylcarbonyloxy-$(C_1-C_4)$ alkyloxy-; $(C_1-C_8)$ dialkylaminocarbonylmethyloxy-; $(C_5-C_{14})$-aryl-$(C_1-C_4)$-dialkylaminocarbonylmethyloxy-; an amino radical non-substituted or monosubstituted or disubstituted by a $(C_1-C_4)$-alkyl and/or $(C_5-C_{14})$-aryl and/or $(C_5-C_{14})$-aryl-$(C_1-C_4)$-alkyl- radical and/or a $(C_1-C_5)$-acyl radical; or the remainder of a D or L amino acid;
—$R^5$ represents $(C_1-C_8)$-alkyl; $(C_5-C_{14})$-aryl; $(C_5-C_{14})$-aryl-$(C_1-C_4)$-alkyl-; $(C_3-C_{12})$-cycloalkyl or $(C_3-C_{12})$-cycloalkyl-$(C_1-C_4)$-alkyl-, bicycloalkyl-$(C_1-C_4)$-alkyl-, tricycloalkyl-$(C_1-C_4)$-alkyl-, said aryl, alkyl, cycloalkyl, bicycloalkyl and tricycloalkyl radicals being non-substituted or substituted by one or more $R^o$ groups; and
$R^o$ represents halogen; amino; nitro; hydroxyl, $(C_1-C_4)$-alkyloxy-; $(C_1-C_4)$-alkylthio-; $(C_1-C_4)$-alkylsulphonyl-; carboxy; $(C_1-C_4)$-alkyloxycarbonyl-; $(C_1-C_8)$-alkyl non-substituted or substituted by one or more halogen atoms, $(C_5-C_{14})$-aryl, $(C_5-C_{14})$-aryl-$(C_1-C_4)$-alkyl-; $(C_5-C_{14})$-aryl-$(C_1-C_4)$-alkyloxy- or $(C_5-C_{14})$-heterocyclyl, or II)
—R represents a radical:

(Ib)

wherein G is selected from the following radicals:
Het-NH—CO—,
Het-NH—CH₂—, or
Het-,
wherein Het represents a monocylcic or polycyclic system, each ring being constituted by 4 to 10 aromatic or non-aromatic members, the ring or at least one of the rings containing 1 to 4 nitrogen atom, and being able to itself be substituted or non-substituted by one or more $R^o$ groups;
—$R^1$ represents an alkyl radical containing 1 to 4 carbon atoms in linear or branched chain; a cycloalkyl radical containing 3 to 6 carbon atoms; or an alkyloxy or alkylthio radical the alkyl part of which contains 1 to 4 carbon atoms in linear or branched chain;
—$R^2$, —$R^3$, —$R^4$, and —$R^5$ are defined as previously in I);
—$R^o$ is defined as previously in I); or III)
—R is defined as previously in II);
—$R^1$, —$R^3$, —$R^4$, and —$R^5$ are defined as previously in I);
—$R^2$ represents a hydroxymethyl radical, a formyl radical or a disubstituted amino radical the substituents of which form together with the nitrogen atom to which they are attached, a saturated or unsaturated heterocycle containing 4 to 6 members; and
—$R^o$ is defined as previously in I); or IV)
—R is defined as previously in II);
—$R^1$, —$R^2$, and —$R^4$ are defined as previously in I);
—$R^3$ represents:
a linear or branched $(C_1-C_4)$ alkyl or $(C_2-C_4)$ alkenyl radical, optionally substituted by an aryl or mono or polycyclic heterocyclyl radical with 4 to 10 members, themselves being able to be substituted by one or more radicals chosen from hydroxy, $(C_1-C_4)$ alkyloxy, amino, $(C_1-C_4)$ alkylamino, $(C_1-C_4)$-dialkylamino, phenyl, cyanophenyl or monocyclic heterocyclyl containing 1 to 4 heteroatoms selected from nitrogen, oxygen or sulphur;
a —$CO_2R^5$ radical,
wherein $R^5$ is substituted and represents $(C_1-C_8)$-alkyl; $(C_5-C_{14})$-aryl; $(C_5-C_{14})$-aryl-$(C_1-C_4)$-alkyl-; $(C_3-C_{12})$-cyclo-alkyl or $(C_3-C_{14})$-cycloalkyl-$(C_1-C_4)$-alkyl-, bicycloalkyl-$(C_1-C_4)$-alkyl-, tricycloalkyl-($C_1$-$C_4$)-alkyl-, the said aryl, alkyl, cycloalkyl, bicycloalkyl and tricycloalkyl radicals being substituted by one or more groups chosen from ($C_1$-$C_4$)-alkylsulphonyl-; ($C_5$-$C_{14}$)-aryl-($C_1$-$C_4$)-alkyloxy- or ($C_5$-$C_{14}$)-heterocyclyl, or a —$COR'^5$ radical, an —$SO_2R'''^5$ radical, wherein —$R'^5$ represents:

($C_1$-$C_8$)-alkyl substituted by a radical as defined for $R^5$ or by a ($C_5$-$C_{14}$) aryloxy radical, the aryl or cycloalkyl radicals themselves being able to be substituted by one or more $R°$ radicals; or a cycloalkyl, aryl or mono or polycyclic heterocyclyl radical optionally substituted by trifluoromethylalkyloxy or ($C_1$-$C_{10}$)-aryl radicals; or ($C_1$-$C_4$) alkylamino; ($C_3$-$C_8$) cycloalkylamino; arylamino or hetero-cyclylamino the aryl or heterocyclyl part of which are mono or polycyclic, these $R'^5$ radicals being able themselves to be substituted by a halogen atom, a nitro, amino, ($C_1$-$C_4$) alkyloxy, ($C_1$-$C_4$) alkyloxycarbonyl, aryl or arylalkyl radical the alkyl part of which contains 1 to 4 carbon atoms in linear or branched chain; and $R'''^5$ represents a ($C_1$-$C_4$) alkylamino or di($C_1$-$C_4$) alkylamino radical the alkyl parts of which can together form a heterocycle with 5 to 7 members, with the nitrogen atom to which they are linked, an arylamino, aralkyl($C_1$-$C_4$) amino or heteroaralkyl ($C_1$-$C_4$) amino radical the aryl or heteroaryl radical of which is mono or polycyclic and comprises 5 to 10 members, the heteroaryl radical being able to contain 1 to 4 heteroatoms chosen from nitrogen, oxygen or sulphur; and —$R°$ is defined as previously in I); or V)
—R, —$R^2$, —$R^3$ and —$R^4$ are defined as previously in I);
—$R^1$ is defined as previously in II); or VI)
—R, —$R^1$, —$R^3$ and —$R^4$ are defined as previously in II);
—$R^2$ is defined as previously in III); or VII)
—R, —$R^1$ and —$R^2$ are defined as previously in I);
—$R^4$ is defined as previously in I); and
—$R^3$ is defined as previously in IV); or VIII)
—R, —$R^1$ and —$R^2$ are defined as previously in II);
—$R^4$ is defined as previously in I); and
—$R^3$ is defined as previously in IV); or IX)
—R and —$R^3$ are defined as previously in I);
—$R^4$ is defined as previously in I);
—$R^1$ is defined as previously in II); and
—$R^2$ is defined as previously in III); or X)
—R and —$R^2$ are defined as previously in I);
—$R^4$ is defined as previously in I);
—$R^1$ is defined as previously in II); and
—$R^3$ is defined as previously in IV); or XI)
—R and —$R^1$ are defined as previously in II);
—$R^4$ is defined as previously in I);
—$R^2$ is defined as previously in III); and
—$R^3$ is defined as previously in IV); or XII)
—R and —$R^4$ are defined as previously in I);
—$R^1$ is defined as previously in II);
—$R^2$ is defined as previously in III);
—$R^3$ is defined as previously in IV);

with the proviso that the above radicals cannot simultaneously have the meaning:
—R represents a radical (Ib) in which G is 1,2,3,4-tetrahydro-1,8-naphthyridin-7-yl,
—$R^1$ represents methyl,
—$R^2$ represents methyl,
—$R^3$ represents benzyloxycarbonyl, and
—$R^4$ represents OH or t-butoxy.

\* \* \* \* \*